US012758508B2

(12) United States Patent
Karve et al.

(10) Patent No.: US 12,758,508 B2
(45) Date of Patent: Oct. 13, 2026

(54) PROCESS OF PREPARING MRNA-LOADED LIPID NANOPARTICLES

(71) Applicant: Translate Bio, Inc., Cambridge, MA (US)

(72) Inventors: Shrirang Karve, Cambridge, MA (US); Frank DeRosa, Cambridge, MA (US); Zarna Bhavsar, Cambridge, MA (US); Michael Heartlein, Cambridge, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 0 days.

(21) Appl. No.: 18/328,206

(22) Filed: Jun. 2, 2023

(65) Prior Publication Data

US 2024/0041789 A1 Feb. 8, 2024

Related U.S. Application Data

(63) Continuation of application No. 15/809,680, filed on Nov. 10, 2017, now abandoned.

(60) Provisional application No. 62/580,155, filed on Nov. 1, 2017, provisional application No. 62/420,413, filed on Nov. 10, 2016.

(51) Int. Cl.

| | |
|---|---|
| ***A61K 9/51*** | (2006.01) |
| ***A61K 9/1272*** | (2025.01) |
| ***A61K 38/17*** | (2006.01) |
| ***A61K 38/18*** | (2006.01) |
| ***A61K 38/44*** | (2006.01) |
| ***A61K 38/45*** | (2006.01) |
| ***A61K 38/53*** | (2006.01) |
| ***A61K 47/22*** | (2006.01) |
| ***A61K 47/28*** | (2006.01) |
| ***C12N 15/88*** | (2006.01) |

(52) U.S. Cl.

CPC .......... *A61K 9/5192* (2013.01); *A61K 9/1272* (2013.01); *A61K 9/5123* (2013.01); *A61K 38/177* (2013.01); *A61K 38/1816* (2013.01); *A61K 38/44* (2013.01); *A61K 38/45* (2013.01); *A61K 38/53* (2013.01); *A61K 47/22* (2013.01); *A61K 47/28* (2013.01); *C12N 15/88* (2013.01); *C12Y 114/16001* (2013.01); *C12Y 201/03003* (2013.01); *C12Y 603/04005* (2013.01)

(58) Field of Classification Search

None

See application file for complete search history.

(56) References Cited

U.S. PATENT DOCUMENTS

| | | | | |
|---|---|---|---|---|
| 4,857,319 A | | 8/1989 | Crowe et al. | |
| 5,049,392 A | | 9/1991 | Weiner et al. | |
| 5,376,380 A | * | 12/1994 | Kikuchi | A61K 9/1277 264/4.1 |
| 6,897,200 B1 | * | 5/2005 | Burke | A61K 47/6901 536/23.1 |
| 7,094,423 B1 | | 8/2006 | Maurer et al. | |
| 2001/0006643 A1 | * | 7/2001 | Hope | A61K 9/1278 424/400 |
| 2003/0124033 A1 | * | 7/2003 | Baker | B01F 23/4105 425/5 |
| 2013/0315987 A1 | * | 11/2013 | Lu | A61P 31/00 514/777 |
| 2014/0206753 A1 | | 7/2014 | Guild et al. | |
| 2015/0086612 A1 | * | 3/2015 | Sahin | A61P 35/04 424/490 |
| 2015/0110857 A1 | | 4/2015 | Derosa et al. | |
| 2016/0038612 A1 | | 2/2016 | Hoge et al. | |
| 2018/0237849 A1 | * | 8/2018 | Thompson | C12Q 1/6872 |
| 2020/0085745 A1 | | 3/2020 | Karve et al. | |
| 2022/0395459 A1 | | 12/2022 | Karve et al. | |

FOREIGN PATENT DOCUMENTS

| | | | | |
|---|---|---|---|---|
| EP | 3020701 A1 | | 5/2016 | |
| JP | 2014-523870 A | | 9/2014 | |
| WO | 9303709 A1 | | 3/1993 | |
| WO | 0105375 A1 | | 1/2001 | |
| WO | WO-0105373 A1 | * | 1/2001 | A61K 31/7088 |
| WO | WO-2008031230 A1 | * | 3/2008 | G01N 33/5091 |
| WO | WO 2012/170889 A1 | | 12/2012 | |
| WO | 2013086526 A1 | | 6/2013 | |
| WO | 2015128030 A1 | | 9/2015 | |
| WO | 2016004318 A1 | | 1/2016 | |
| WO | 2021127641 A1 | | 6/2021 | |

OTHER PUBLICATIONS

Abraham et al. Journal of Controlled Release 96 (2004) 449-461 (Year: 2004).*

Jung et al. Colloids and Surfaces B: Biointerfaces 2010 76:434-440 (Year: 2010).*

Stuart et al. "Encapsulation Processes by Bilayer Vesicles", Molecular Encapsulation: Organic Reactions in Constrained Systems, Brinker et al. (Eds.), John Wiley and Sons Ltd., 2010, p. 421-454 (Year: 2010).*

Midoux et al. Expert Review of Vaccines 2015 14(2) 221-234; ePub Dec. 2014 (Year: 2015).*

Hochmeister "Parameters influencing transfection efficiency of mRNA lipoplexes" Diploma thesis for Master of Pharmacy (Year: 2014).*

Yu et al. Anticancer Research 2011 31:771-776 (Year: 2011).*

Wu et al. (Journal of Controlled Release 2011 155:418-426 (Year: 2011).*

(Continued)

*Primary Examiner* — Melissa S Mercier

*Assistant Examiner* — Caralynne E Helm

(74) *Attorney, Agent, or Firm* — LATHROP GPM LLP; James H. Velema, Esq.

(57) ABSTRACT

The present invention provides an improved process for lipid nanoparticle formulation and mRNA encapsulation. In some embodiments, the present invention provides a process of encapsulating messenger RNA (mRNA) in lipid nanoparticles comprising a step of mixing a solution of pre-formed lipid nanoparticles and mRNA.

20 Claims, 32 Drawing Sheets

Specification includes a Sequence Listing.

(56) References Cited

OTHER PUBLICATIONS

Current Protocols in Cell Biology 1998 John Wiley & Sons, Inc. A.2A.1-A.2A.10 (Year: 1998).*
Torchilin et al. (Biochimica et Biophysica Acta 2001 1511:397-411 (Year: 2001).*
Thierry et al. Biochimica et Biophysica Acta 2009 1790:385-394 (Year: 2009).*
Weisman et al. Biophysical Journal vol. 2004 87:609-614 (Year: 2004).*
Koynova Analysis of Lipoplex Structure and Lipid Phase Changes. V. Weissig (ed.), Liposomes: Methods and Protocols, vol. 2: Biological Membrane Models, Humana Totowa:Humana Press 2010 p. 399-423 (Year: 2010).*
International Search Report and Written Opinion for PCT/US2017/061113 dated Mar. 2, 2018 (20 pages).
"Opti-MEM I Reduced Serum Medium", GIBCO Corporation, Jun. 2001, Form No. 2017, Product Information (1 page).
Avnir et al., "Amphipathic weak acid glucocorticoid prodrugs remote-loaded into sterically stabilized nanoliposomes evaluated in arthritic rats and in a Beagle dog: A novel approach to treating autoimmune arthritis", Arthritis & Rheumatology, vol. 58,No. 1, Jan. 2008, pp. 119-129, DOI: 10.1002/art.23230 (11 pages).
Belliveau et al., "Microfluidic Synthesis of Highly Potent Limit-size Lipid Nanoparticles for In Vitro Delivery of siRNA", Molecular Therapy—Nucleic Acids, vol. 1, No. e37, 2012, DOI: 10.1038/mtna.2012.28 (9 pages).
Buyens et al., "Liposome based systems for systemic siRNA delivery: Stability in blood sets the requirements for optimal carrier design", Journal of Controlled Release, vol. 158, No. 3, Mar. 28, 2012, pp. 362-370,DOI: 10.1016/j.jconrel.2011.10.009, (9 pages).
Fenske et al., "Liposomal nanomedicines", Expert Opinion on Drug Delivery, vol. 5, No. 1, 2008, pp. 25-44 (20 pages), 2008.
Fritze et al., "Remote loading of doxorubicin into liposomes driven by a transmembrane phosphate gradient", Biochimica et Biophysica Acta (BBA)—Biomembranes, vol. 1758, No. 10, Oct. 2006, pp. 1633-1640,DOI: 10.1016/j.bbamem.2006.05.028, (8 pages).
Gjetting et al., "A simple protocol for preparation of a liposomal vesicle with encapsulated plasmid DNA that mediate high accumulation and reporter gene activity in tumor tissue", Results in Pharma Sciences, vol. 1, No. 1, May 2011, pp. 49-56Citation Cont'd: DOI: 10.1016/j.rinphs.2011.08.001 (8 pages).
Hayes et al., "Genospheres: self-assembling nucleic acid-lipid nanoparticles suitable for targeted gene delivery", Gene Therapy, vol. 13, 2006, pp. 646-651, (6 pages).
Hood et al., "Microfluidic remote loading for rapid single-step liposomal drug preparation", Lab on a Chip, vol. 14, 2014, pp. 3359-3367, DOI: 10.1039/c4lc00390j, (9 pages).
Jeffs et al., "A Scalable, Extrusion-Free Method for Efficient Liposomal Encapsulation of Plasmid DNA", Pharmaceutical Research, vol. 22, No. 3, Mar. 2005, DOI: 10.1007/s11095-004-1873-z, pp. 362-372 (11 pages).
Kauffman et al., "Optimization of Lipid Nanoparticle Formulations for mRNA Delivery in Vivo with Fractional Factorial and Definitive Screening Designs", Nano Letters, vol. 15, No. 11, 2015, pp. 7300-7306, DOI: 10.1021/acs.nanolett.5b02497 (7 pages.
Kubota et al., "Effect of the nanoformulation of siRNA-lipid assemblies on their cellular uptake and immune stimulation", International Journal of Nanomedicine, vol. 12, 2017, pp. 5121-5133, Doi: 10.2147/IJN.S136426, (22 pages).
Leung et al., "Lipid Nanoparticles Containing siRNA Synthesized by Microfluidic Mixing Exhibit an Electron-Dense Nanostructured Core", The Journal of Physical Chemistry, vol. 116, No. 34, Jul. 18, 2012, pp. 18440-18450, DOI: 10.1021/jp303267y (11 pages).
Martinon et al., "Induction of virus-specific cytotoxic T lymphocytes in vivo by liposome-entrapped mRNA", European Journal of Immunology, vol. 23, 1993, pp. 1719-1722 (4 pages).
Maurer et al., "Spontaneous Entrapment of Polynucleotides upon Electrostatic Interaction with Ethanol-Destabilized Cationic Liposomes", Biophysical Journal, vol. 80, No. 5, May 2001, pp. 2310-2326, DOI: 10.1016/S0006-3495(01)76202-9 (17 pages).
Mukerjee et al., "Formulation, Characterization and Evaluation of Curcumin-loaded PLGA Nanospheres for Cancer Therapy", Anticancer Research, vol. 29, 2009, pp. 3867-3876 (9 pages).
Muppidi et al., "Development and Stability Studies of Novel Liposomal Vancomycin Formulations", International Scholarly Research Network, vol. 2012, Article ID 636743, 2012, pp. 1-8, DOI: 10.5402/2012/636743 (8 pages).
Piacentini, E., "Encapsulation Efficiency", Encyclopedia of Membranes, 2016, pp. 706-707, DOI: 10.1007/978-3-662-44324-8 (4 pages).
Rejman et al., "mRNA transfection of cervical carcinoma and mesenchymal stem cells mediated by cationic carriers", Journal of Controlled Release, vol. 147, No. 3, Nov. 1, 2010, pp. 385-391,DOI: 10.1016/j.jconrel.2010.07.124, (7 pages).
Wan et al., "Lipid nanoparticle delivery systems for siRNA-based therapeutics", Drug Delivery and Translational Research, vol. 4, 2014, pp. 74-83, DOI: 10.1007/s13346-013-0161-z, (10 pages), 74-83.
Wang et al., "Encapsulating Protein into Preformed Liposomes by Ethanol-Destabilized Method", Artificial Cells, Blood Substitutes, and Biotechnology, vol. 31, No. 3, 2003, pp. 303-312, DOI: 10.1081/BIO-120023160 (11 pages).
Wang et al., "Systemic Delivery of Modified mRNA Encoding Herpes Simplex Virus 1 Thymidine Kinase for Targeted Cancer Gene Therapy", Molecular Therapy, vol. 21, No. 2, Feb. 2013, pp. 358-367, DOI: 10.1038/mt.2012.250, (10 pages).
Zang et al., "Anti-EphA10 antibody-conjugated pH-sensitive liposomes for specific intracellular delivery of siRNA", International Journal of Nanomedicine, vol. 11, 2016, pp. 3951-3967, DOI: 10.2147/IJN.S107952 (17 pages).
Felgner et al., "Lipofection: a highly efficient, lipid-mediated DNA-transfection procedure", PNAS USA, Nov. 1987, 84(21): 7413-7417.
MacLachlan et al., "Liposomal Formulations for Nucleic Acid Delivery", Antisense Drug Technology—Principles, Strategies and Applications, 2006, Second Edition, Chapter 9, pp. 237-270.
Son et al., "Cationic liposome and plasmid DNA complexes formed in serum-free medium under optimum transfection condition are negatively charged", Biochimica et Biophysica Acta (BBA)—Biomembranes, Jun. 1, 2000, 1466(1-2): 11-15.

* cited by examiner cKK-E12

Saline

PROCESS OF PREPARING MRNA-LOADED LIPID NANOPARTICLES

RELATED APPLICATIONS

This application claims priority to U.S. application Ser. No. 15/809,680, filed Nov. 10, 2017, which claims priority to U.S. Provisional Application Ser. No. 62/420,413, filed Nov. 10, 2016 and U.S. Provisional Application Ser. No. 62/580,155, filed Nov. 1, 2017, the disclosures of which are hereby incorporated by reference.

SEQUENCE LISTING

The present specification makes reference to a Sequence Listing (submitted electronically as an xml file named "20230524 MRT-1246US2 SL" on Jun. 2, 2023). The xml file was generated on May 24, 2023 and is 19300 bytes in size. The entire contents of the Sequence Listing are herein incorporated by reference.

BACKGROUND

Messenger RNA therapy (MRT) is becoming an increasingly important approach for the treatment of a variety of diseases. MRT involves administration of messenger RNA (mRNA) to a patient in need of the therapy for production of the protein encoded by the mRNA within the patient's body. Lipid nanoparticles are commonly used to encapsulate mRNA for efficient in vivo delivery of mRNA.

To improve lipid nanoparticle delivery, much effort has focused on identifying novel lipids or particular lipid compositions that can affect intracellular delivery and/or expression of mRNA, e.g., in various types of mammalian tissue, organs and/or cells (e.g., mammalian liver cells). However, these existing approaches are costly, time consuming and unpredictable.

SUMMARY OF INVENTION

The present invention provides, among other things, an improved process for preparing mRNA-loaded lipid nanoparticles. In particular, the present invention is based on the surprising discovery that encapsulating mRNA by combining pre-formed lipid nanoparticles with mRNA results in formulated particles that exhibit unexpectedly efficient in vivo delivery of the mRNA and surprisingly potent expression of protein(s) and/or peptide(s) that the mRNA encodes.

As compared to conventional processes, the inventive process described herein provides higher potency and better efficacy of lipid nanoparticle delivered mRNA, thereby shifting the therapeutic index in a positive direction and providing additional advantages, such as lower cost, better patient compliance, and more patient friendly dosing regimens. mRNA-loaded lipid nanoparticle formulations provided by the present invention may be successfully delivered in vivo for more potent and efficacious protein expression via different routes of administration such as intravenous, intramuscular, intra-articular, intrathecal, inhalation (respiratory), subcutaneous, intravitreal, and ophthalmic.

This inventive process can be performed using a pump system and is therefore scalable, allowing for improved particle formation/formulation in amounts sufficient for, e.g., performance of clinical trials and/or commercial sale. Various pump systems may be used to practice the present invention including, but not limited to, pulse-less flow pumps, gear pumps, peristaltic pumps, and centrifugal pumps.

This inventive process also results in superior encapsulation efficiency, mRNA recovery rate, and homogeneous particle sizes.

Thus, in one aspect, the present invention provides a process of encapsulating messenger RNA (mRNA) in lipid nanoparticles comprising a step of mixing a solution comprising pre-formed lipid nanoparticles and a solution comprising mRNA such that lipid nanoparticles encapsulating mRNA are formed. As used herein, pre-formed lipid nanoparticles are substantially free of mRNA. In some embodiments, preformed lipid nanoparticles are referred to as empty lipid nanoparticles.

In some embodiments, the process according to the present invention includes a step of heating one or more of the solutions (i.e., applying heat from a heat source to the solution) to a temperature (or to maintain at a temperature) greater than ambient temperature, the one more solutions being the solution comprising the pre-formed lipid nanoparticles, the solution comprising the mRNA and the mixed solution comprising the lipid nanoparticle encapsulated mRNA. In some embodiments, the process includes the step of heating one or both of the mRNA solution and the pre-formed lipid nanoparticle solution, prior to the mixing step. In some embodiments, the process includes heating one or more one or more of the solution comprising the pre-formed lipid nanoparticles, the solution comprising the mRNA and the solution comprising the lipid nanoparticle encapsulated mRNA, during the mixing step. In some embodiments, the process includes the step of heating the lipid nanoparticle encapsulated mRNA, after the mixing step. In some embodiments, the temperature to which one or more of the solutions is heated (or at which one or more of the solutions is maintained) is or is greater than about 30° C., 37° C., 40° C., 45° C., 50° C., 55° C., 60° C., 65° C., or 70° C. In some embodiments, the temperature to which one or more of the solutions is heated ranges from about 25-70° C., about 30-70° C., about 35-70° C., about 40-70° C., about 45-70° C., about 50-70° C., or about 60-70° C. In some embodiments, the temperature greater than ambient temperature to which one or more of the solutions is heated is about 65° C.

In some embodiments, the process according to the present invention includes maintaining at ambient temperature (i.e., not applying heat from a heat source to the solution) one or more of the solution comprising the pre-formed lipid nanoparticles, the solution comprising the mRNA and the mixed solution comprising the lipid nanoparticle encapsulated mRNA. In some embodiments, the process includes the step of maintaining at ambient temperature one or both of the mRNA solution and the pre-formed lipid nanoparticle solution, prior to the mixing step. In some embodiments, the process includes maintaining at ambient temperature one or more one or more of the solution comprising the pre-formed lipid nanoparticles, the solution comprising the mRNA and the solution comprising the lipid nanoparticle encapsulated mRNA, during the mixing step. In some embodiments, the process includes the step of maintaining at ambient temperature the lipid nanoparticle encapsulated mRNA, after the mixing step. In some embodiments, the ambient temperature at which one or more of the solutions is maintained is or is less than about 35° C., 30° C., 25° C., 20° C., or 16° C. In some embodiments, the ambient temperature at which one or more of the solutions is maintained ranges from about 15-35° C., about 15-30° C., about 15-25° C., about 15-20°

C., about 20-35° C., about 25-35° C., about 30-35° C., about 20-30° C., about 25-30° C. or about 20-25° C. In some embodiments, the ambient temperature at which one or more of the solutions is maintained is 20-25° C.

In some embodiments, the process according to the present invention includes performing at ambient temperature the step of mixing the solution comprising pre-formed lipid nanoparticles and the solution comprising mRNA to form lipid nanoparticles encapsulating mRNA.

In some embodiments, the pre-formed lipid nanoparticles are formed by mixing lipids dissolved in ethanol with an aqueous solution. In some embodiments, the lipids contain one or more cationic lipids, one or more helper lipids, and one or more PEG lipids. In some embodiments, the lipids also contain one or more cholesterol lipids. The pre-formed lipid nanoparticles are formed by the mixing of those lipids. Accordingly, in some embodiments, the pre-formed lipid nanoparticles comprise one or more cationic lipids, one or more helper lipids, and one or more PEG lipids. In some embodiments, the pre-formed lipid nanoparticles also contain one or more cholesterol lipids.

In some embodiments, the one or more cationic lipids are selected from the group consisting of cKK-E12, OF-02, C12-200, MC3, DLinDMA, DLinkC2DMA, ICE (Imidazol-based), HGT5000, HGT5001, HGT4003, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, 3-(4-(bis(2-hydroxydodecyl)amino)butyl)-6-(4-((2-hydroxydodecyl)(2-hydroxyundecyl)amino)butyl)-1,4-dioxane-2,5-dione (Target 23), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione (Target 24), N1GL, N2GL, V1GL and combinations thereof.

In some embodiments, the one or more cationic lipids are amino lipids. Amino lipids suitable for use in the invention include those described in WO2017180917, which is hereby incorporated by reference. Exemplary aminolipids in WO2017180917 include those described at paragraph [0744] such as DLin-MC3-DMA (MC3), (13Z,16Z)-N,N-dimethyl-3-nonyldocosa-13,16-dien-1-amine (L608), and Compound 18. Other amino lipids include Compound 2, Compound 23, Compound 27, Compound 10, and Compound 20. Further amino lipids suitable for use in the invention include those described in WO2017112865, which is hereby incorporated by reference. Exemplary amino lipids in WO2017112865 include a compound according to one of formulae (I), (Ia1)-(Ia6), (lb), (II), (IIa), (III), (IIia), (IV), (17-1), (19-1), (19-11), and (20-1), and compounds of paragraphs [00185], [00201], [0276]. In some embodiments, cationic lipids suitable for use in the invention include those described in WO2016118725, which is hereby incorporated by reference. Exemplary cationic lipids in WO2016118725 include those such as KL22 and KL25. In some embodiments, cationic lipids suitable for use in the invention include those described in WO2016118724, which is hereby incorporated by reference. Exemplary cationic lipids in WO2016118725 include those such as KL10, 1,2-dilinoleyloxy-N,N-dimethylaminopropane (DLin-DMA), and KL25.

In some embodiments, the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)).

In some embodiments, the one or more PEG-modified lipids comprise a poly(ethylene) glycol chain of up to 5 kDa in length covalently attached to a lipid with alkyl chain(s) of $C_6$-$C_{20}$ length.

In some embodiments, the pre-formed lipid nanoparticles are purified by a Tangential Flow Filtration (TFF) process. In some embodiments, greater than about 50%, 55%, 60%, 65%, 70%, 75%, 80%, 85%, 90%, 95%, 96%, 97%, 98%, or 99% of the purified nanoparticles have a size less than about 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, or about 50 nm). In some embodiments, substantially all of the purified nanoparticles have a size less than 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, or about 50 nm). In some embodiments, greater than about 70%, 75%, 80%, 85%, 90%, 95%, 96%, 97%, 98%, 99% of the purified nanoparticles have a size ranging from 50-150 nm. In some embodiments, substantially all of the purified nanoparticles have a size ranging from 50-150 nm. In some embodiments, greater than about 70%, 75%, 80%, 85%, 90%, 95%, 96%, 97%, 98%, 99% of the purified nanoparticles have a size ranging from 80-150 nm. In some embodiments, substantially all of the purified nanoparticles have a size ranging from 80-150 nm.

In some embodiments, a process according to the present invention results in an encapsulation rate of greater than about 90%, 95%, 96%, 97%, 98%, or 99%. In some embodiments, a process according to the present invention results in greater than about 60%, 65%, 70%, 75%, 80%, 85%, 90%, 95%, 96%, 97%, 98%, or 99% recovery of mRNA.

In some embodiments, the pre-formed lipid nanoparticles and mRNA are mixed using a pump system. In some embodiments, the pump system comprises a pulse-less flow pump. In some embodiments, the pump system is a gear pump. In some embodiments, a suitable pump is a peristaltic pump. In some embodiments, a suitable pump is a centrifugal pump. In some embodiments, the process using a pump system is performed at large scale. For example, in some embodiments, the process includes using pumps as described herein to mix a solution of at least about 1 mg, 5 mg, 10 mg, 50 mg, 100 mg, 500 mg, or 1000 mg of mRNA with a solution of pre-formed lipid nanoparticles, to produce mRNA encapsulated in lipid nanoparticles. In some embodiments, the process of mixing mRNA with pre-formed lipid nanoparticles provides a composition according to the present invention that contains at least about 1 mg, 5 mg, 10 mg, 50 mg, 100 mg, 500 mg, or 1000 mg of encapsulated mRNA.

In some embodiments, the solution comprising pre-formed lipid nanoparticles is mixed at a flow rate ranging from about 25-75 ml/minute, about 75-200 ml/minute, about 200-350 ml/minute, about 350-500 ml/minute, about 500-650 ml/minute, about 650-850 ml/minute, or about 850-1000 ml/minute. In some embodiments, the solution comprising pre-formed lipid nanoparticles is mixed at a flow rate of about 50 ml/minute, about 100 ml/minute, about 150 ml/minute, about 200 ml/minute, about 250 ml/minute, about 300 ml/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

In some embodiments, the mRNA is mixed in a solution at a flow rate ranging from about 25-75 ml/minute, about 75-200 ml/minute, about 200-350 ml/minute, about 350-500 ml/minute, about 500-650 ml/minute, about 650-850 ml/minute, or about 850-1000 ml/minute. In some embodiments, the mRNA is mixed in a solution at a flow rate of about 50 ml/minute, about 100 ml/minute, about 150 ml/minute, about 200 ml/minute, about 250 ml/minute, about 300 ml/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

In some embodiments, a process according to the present invention includes a step of first generating pre-formed lipid nanoparticle solution by mixing a citrate buffer with lipids dissolved in ethanol.

In some embodiments, a process according to the present invention includes a step of first generating an mRNA solution by mixing a citrate buffer with an mRNA stock solution. In certain embodiments, a suitable citrate buffer contains about 10 mM citrate, about 150 mM NaCl, pH of about 4.5. In some embodiments, a suitable mRNA stock solution contains the mRNA at a concentration at or greater than about 1 mg/ml, about 10 mg/ml, about 50 mg/ml, or about 100 mg/ml.

In some embodiments, the citrate buffer is mixed at a flow rate ranging between about 100-300 ml/minute, 300-600 ml/minute, 600-1200 ml/minute, 1200-2400 ml/minute, 2400-3600 ml/minute, 3600-4800 ml/minute, or 4800-6000 ml/minute. In some embodiments, the citrate buffer is mixed at a flow rate of about 220 ml/minute, about 600 ml/minute, about 1200 ml/minute, about 2400 ml/minute, about 3600 ml/minute, about 4800 ml/minute, or about 6000 ml/minute.

In some embodiments, the mRNA stock solution is mixed at a flow rate ranging between about 10-30 ml/minute, about 30-60 ml/minute, about 60-120 ml/minute, about 120-240 ml/minute, about 240-360 ml/minute, about 360-480 ml/minute, or about 480-600 ml/minute. In some embodiments, the mRNA stock solution is mixed at a flow rate of about 20 ml/minute, about 40 ml/minute, about 60 ml/minute, about 80 ml/minute, about 100 ml/minute, about 200 ml/minute, about 300 ml/minute, about 400 ml/minute, about 500 ml/minute, or about 600 ml/minute.

In some embodiments, the lipid nanoparticles encapsulating mRNA are prepared with the pre-formed lipid nanoparticles by mixing an aqueous solution containing the mRNA with an aqueous solution containing the pre-formed lipid nanoparticles. In some embodiments, the aqueous solution containing the mRNA and/or the aqueous solution containing the pre-formed lipid nanoparticles is an aqueous solution comprising pharmaceutically acceptable excipients, including, but not limited to, one or more of trehalose, sucrose, lactose, and mannitol.

In some embodiments, one or both of a non-aqueous solvent, such as ethanol, and citrate are absent (i.e., below detectable levels) from one or both of the solution containing the mRNA and the solution containing the pre-formed lipid nanoparticles during the mixing addition of the mRNA to the pre-formed lipid nanoparticles. In some embodiments, one or both of the solution containing the mRNA and the solution containing the pre-formed lipid nanoparticles are buffer exchanged to remove one or both of non-aqueous solvents, such as ethanol, and citrate prior to the mixing addition of the mRNA to the pre-formed lipid nanoparticles. In some embodiments, one or both of the solution containing the mRNA and the solution containing the pre-formed lipid nanoparticles include only residual citrate during the mixing addition of mRNA to the pre-formed lipid nanoparticles. In some embodiments, one or both of the solution containing the mRNA and the solution containing the pre-formed lipid nanoparticles include only residual non-aqueous solvent, such as ethanol. In some embodiments, one or both of the solution containing the mRNA and the solution containing the pre-formed lipid nanoparticles contains less than about 10 mM (e.g., less than about 9 mM, about 8 mM, about 7 mM, about 6 mM, about 5 mM, about 4 mM, about 3 mM, about 2 mM, or about 1 mM) of citrate present during the addition of mRNA to the pre-formed lipid nanoparticles. In some embodiments, one or both of the solution containing the mRNA and the solution containing the pre-formed lipid nanoparticles contains less than about 25% (e.g., less than about 20%, about 15%, about 10%, about 5%, about 4%, about 3%, about 2%, or about 1%) of non-aqueous solvents, such as ethanol, present during the addition of mRNA to the pre-formed lipid nanoparticles. In some embodiments, the solution comprising the lipid nanoparticles encapsulating mRNA does not require any further downstream processing (e.g., buffer exchange and/or further purification steps) after the pre-formed lipid nanoparticles and mRNA are mixed to form that solution.

In another aspect, the present invention provides a composition of lipid nanoparticles encapsulating mRNA generated by a process described herein. In some embodiments, a substantial amount of the lipid nanoparticles are pre-formed. In some embodiments, at least 85% (e.g., at least 86%, 87%, 88%, 89%, 90%, 91%, 92%, 93%, 94%, 95%, 96%, 97%, 98%, or 99%) of the lipid nanoparticles are pre-formed. In some embodiments, the present invention provides a composition comprising purified lipid nanoparticles, wherein greater than about 90% of the purified lipid nanoparticles have an individual particle size of less than about 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, or about 50 nm) and greater than about 70% of the purified lipid nanoparticles encapsulate an mRNA within each individual particle. In some embodiments, greater than about 95%, 96%, 97%, 98%, or 99% of the purified lipid nanoparticles have an individual particle size of less than about 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about nm, or about 50 nm). In some embodiments, substantially all of the purified lipid nanoparticles have an individual particle size of less than about 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, or about 50 nm). In some embodiments, greater than about 70%, 75%, 80%, 85%, 90%, 95%, 96%, 97%, 98%, 99% of the purified nanoparticles have a size ranging from 50-150 nm. In some embodiments, substantially all of the purified nanoparticles have a size ranging from 50-150 nm. In some embodiments, greater than about 70%, 75%, 80%, 85%, 90%, 95%, 96%, 97%, 98%, 99% of the purified nanoparticles have a size ranging from 80-150 nm. In some embodiments, substantially all of the purified nanoparticles have a size ranging from 80-150 nm.

In some embodiments, greater than about 90%, 95%, 96%, 97%, 98%, or 99% of the purified lipid nanoparticles encapsulate an mRNA within each individual particle. In some embodiments, substantially all of the purified lipid nanoparticles encapsulate an mRNA within each individual particle. In some embodiments, a composition according to the present invention contains at least about 1 mg, 5 mg, 10 mg, 100 mg, 500 mg, or 1000 mg of encapsulated mRNA.

In some embodiments, a pre-formed lipid nanoparticle comprises one or more cationic lipids, one or more helper lipids and one or more PEG lipids. In some embodiments, each individual lipid nanoparticle also comprises one or more cholesterol based lipids. In some embodiments, the one or more cationic lipids are selected from the group consisting of cKK-E12, OF-02, C12-200, MC3, DLinDMA, DLinkC2DMA, ICE (Imidazol-based), HGT5000, HGT5001, HGT4003, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, 3-(4-(bis(2-hydroxydodecyl)amino)butyl)-6-(4-((2-hydroxydodecyl)(2-hydroxyundecyl)amino)butyl)-1,4-dioxane-2,5-dione (Target 23), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione (Target 24), N1GL, N2GL, V1GL and combinations thereof.

In some embodiments, the one or more cationic lipids are amino lipids. Amino lipids suitable for use in the invention include those described in WO2017180917, which is hereby incorporated by reference. Exemplary aminolipids in WO2017180917 include those described at paragraph [0744] such as DLin-MC3-DMA (MC3), (13Z,16Z)-N,N-dimethyl-3-nonyldocosa-13,16-dien-1-amine (L608), and Compound 18. Other amino lipids include Compound 2, Compound 23, Compound 27, Compound 10, and Compound 20.

Further amino lipids suitable for use in the invention include those described in WO2017112865,1 which is hereby incorporated by reference. Exemplary amino lipids in WO2017112865 include a compound according to one of formulae (I), (Ia1)-(Ia6), (lb), (II), (IIa), (III), (IIia), (IV), (17-1), (19-1), (19-11), and (20-1), and compounds of paragraphs [00185], [00201], [0276]. In some embodiments, cationic lipids suitable for use in the invention include those described in WO2016118725, which is hereby incorporated by reference. Exemplary cationic lipids in WO2016118725 include those such as KL22 and KL25. In some embodiments, cationic lipids suitable for use in the invention include those described in WO2016118724, which is hereby incorporated by reference. Exemplary cationic lipids in WO2016118725 include those such as KL10, 1,2-dilinoleyloxy-N,N-dimethylaminopropane (DLin-DMA), and KL25.

In some embodiments, the one or more non-cationic lipids are selected from DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DOPC (1,2-dioleyl-sn-glycero-3-phosphotidylcholine) DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)).

In some embodiments, the one or more cholesterol-based lipids is cholesterol or PEGylated cholesterol. In some embodiments, the one or more PEG-modified lipids contain a poly(ethylene) glycol chain of up to 5 kDa in length covalently attached to a lipid with alkyl chain(s) of $C_6$-$C_{20}$ length.

In some embodiments, the present invention is used to encapsulate mRNA containing one or more modified nucleotides. In some embodiments, one or more nucleotides is modified to a pseudouridine. In some embodiments, one or more nucleotides is modified to a 5-methylcytidine. In some embodiments, the present invention is used to encapsulate mRNA that is unmodified.

In yet another aspect, the present invention provides a method of delivering mRNA for in vivo protein production comprising administering into a subject a composition of lipid nanoparticles encapsulating mRNA generated by the process described herein, wherein the mRNA encodes one or more protein(s) or peptide(s) of interest.

In another aspect, the present invention provides a method for encapsulating messenger RNA (mRNA) in lipid nanoparticles wherein the method is performed without use of ethanol. In some embodiments, the method comprises a step of mixing a solution comprising one or more cationic lipids, one or more non-cationic lipids and one or more PEG-modified lipids with a solution comprising mRNA. In some embodiments, in the solution comprising the one or more cationic lipids, one or more non-cationic lipids and one or more PEG-modified lipids, at least a portion of the one or more cationic lipids, one or more non-cationic lipids and one or more PEG-modified lipids are present as pre-formed lipid nanoparticles. In some embodiments, the method is performed also without the use of citrate.

In certain embodiments, the method is performed without the use of any non-aqueous solvent. In some embodiments, there is no detectable ethanol and/or no detectable non-aqueous solvent. In some embodiments, there is no detectable citrate. In some embodiments, there is only a residual amount of ethanol and/or non-aqueous solvent that is present at less than about 25% (e.g., less than about 20%, about 15%, about 10%, about 5%, about 4%, about 3%, about 2%, or about 1%) of the solution. In some embodiments, there is only a residual amount of citrate that is less than 10 mM (e.g., less than about 9 mM, about 8 mM, about 7 mM, about 6 mM, about 5 mM, about 4 mM, about 3 mM, about 2 mM, or about 1 mM).

In this application, the use of "or" means "and/or" unless stated otherwise. As used in this disclosure, the term "comprise" and variations of the term, such as "comprising" and "comprises," are not intended to exclude other additives, components, integers or steps. As used in this application, the terms "about" and "approximately" are used as equivalents. Both terms are meant to cover any normal fluctuations appreciated by one of ordinary skill in the relevant art.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWINGS

The drawings are for illustration purposes only and not for limitation.

FIG. 27(*a*)-(*b*) depicts results from mRNA lipid nanoparticles produced by Process B. FIG. 27(*c*)-(*d*) depicts results from mRNA lipid nanoparticles produced by Process A.

DEFINITIONS

Figure 1:
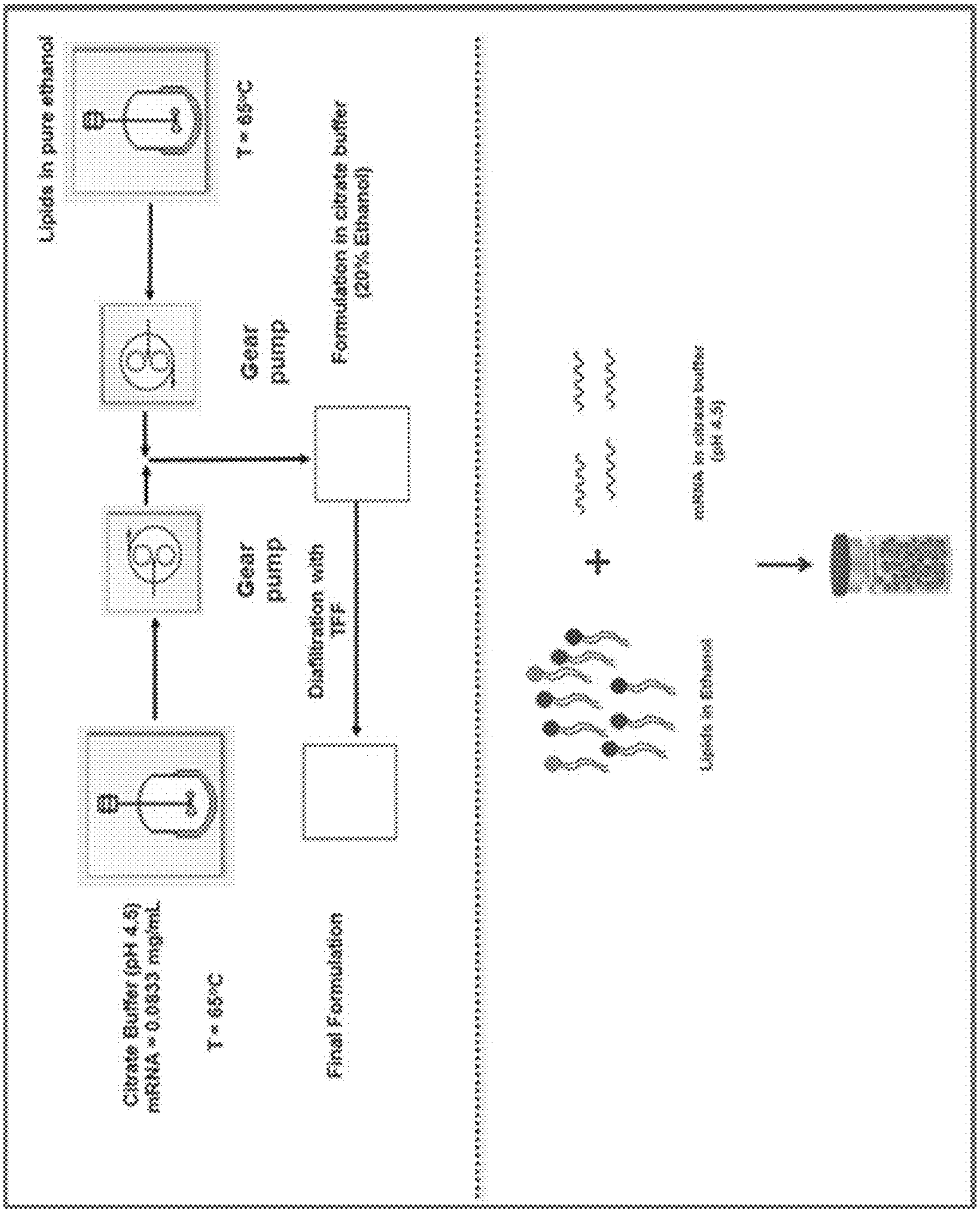
FIG. 1 shows a schematic of an exemplary lipid nanoparticle mRNA encapsulation process (Process A) that involves mixing lipids dissolved in ethanol with mRNA dissolved in an aqueous buffer, using a pump system.

In order for the present invention to be more readily understood, certain terms are first defined below. Additional definitions for the following terms and other terms are set forth throughout the specification.

Alkyl: As used herein, "alkyl" refers to a radical of a straight-chain or branched saturated hydrocarbon group having from 1 to 20 carbon atoms ("$C_{1-20}$ alkyl"). In some embodiments, an alkyl group has 1 to 3 carbon atoms ("$C_{1-3}$ alkyl"). Examples of $C_{1-3}$ alkyl groups include methyl ($C_1$), ethyl ($C_2$), n-propyl ($C_3$), and isopropyl ($C_3$). In some embodiments, an alkyl group has 8 to 12 carbon atoms ("$C_{8-12}$ alkyl"). Examples of $C_{8-12}$ alkyl groups include, without limitation, n-octyl ($C_8$), n-nonyl ($C_9$), n-decyl ($C_{10}$), n-undecyl ($C_{11}$), n-dodecyl ($C_{12}$) and the like. The prefix "n-" (normal) refers to unbranched alkyl groups. For example, n-$C_8$ alkyl refers to $-(CH_2)_7CH_3$, n-$C_{10}$ alkyl refers to $-(CH_2)_9CH_3$, etc.

Amino acid: As used herein, term "amino acid," in its broadest sense, refers to any compound and/or substance that can be incorporated into a polypeptide chain. In some embodiments, an amino acid has the general structure $H_2N-C(H)(R)-COOH$. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term "delivery" encompasses both local and systemic delivery. For example, delivery of mRNA encompasses situations in which an mRNA is delivered to a target tissue and the encoded protein or peptide is expressed and retained within the target tissue (also referred to as "local distribution" or "local delivery"), and situations in which an mRNA is delivered to a target tissue and the encoded protein or peptide is expressed and secreted into patient's circulation system (e.g., serum) and systematically distributed and taken up by other tissues (also referred to as "systemic distribution" or "systemic delivery).

Efficacy: As used herein, the term "efficacy," or grammatical equivalents, refers to an improvement of a biologically relevant endpoint, as related to delivery of mRNA that encodes a relevant protein or peptide. In some embodiments, the biological endpoint is protecting against an ammonium chloride challenge at certain timepoints after administration.

Encapsulation: As used herein, the term "encapsulation," or grammatical equivalent, refers to the process of confining an individual mRNA molecule within a nanoparticle.

Expression: As used herein, "expression" of a mRNA refers to translation of an mRNA into a peptide (e.g., an antigen), polypeptide, or protein (e.g., an enzyme) and also can include, as indicated by context, the post-translational modification of the peptide, polypeptide or fully assembled protein (e.g., enzyme). In this application, the terms "expression" and "production," and grammatical equivalent, are used inter-changeably.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control sample or subject (or multiple control samples or subjects) in the absence of the treatment described herein. A "control sample" is a sample subjected to the same conditions as a test sample, except for the test article. A "control subject" is a subject afflicted with the same form of disease as the subject being treated, who is about the same age as the subject being treated.

Impurities: As used herein, the term "impurities" refers to substances inside a confined amount of liquid, gas, or solid, which differ from the chemical composition of the target material or compound. Impurities are also referred to as contaminants.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Local distribution or delivery: As used herein, the terms "local distribution," "local delivery," or grammatical equivalent, refer to tissue specific delivery or distribution. Typically, local distribution or delivery requires a peptide or protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polynucleotide that encodes at least one peptide, polypeptide or protein. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, pseudouridine, and 5-methylcytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or rnalonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium. quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Potency: As used herein, the term "potency," or grammatical equivalents, refers to expression of protein(s) or peptide(s) that the mRNA encodes and/or the resulting biological effect.

Salt: As used herein the term "salt" refers to an ionic compound that does or may result from a neutralization reaction between an acid and a base.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Yield: As used herein, the term "yield" refers to the percentage of mRNA recovered after encapsulation as compared to the total mRNA as starting material. In some embodiments, the term "recovery" is used interchangeably with the term "yield".

DETAILED DESCRIPTION

The present invention provides an improved process for lipid nanoparticle formulation and mRNA encapsulation. In some embodiments, the present invention provides a process of encapsulating messenger RNA (mRNA) in lipid nanoparticles comprising the steps of forming lipids into pre-formed lipid nanoparticles (i.e., formed in the absence of mRNA) and then combining the pre-formed lipid nanoparticles with mRNA. In some embodiments, the novel formulation process results in an mRNA formulation with higher potency (peptide or protein expression) and higher efficacy (improvement of a biologically relevant endpoint) both in vitro and in vivo with potentially better tolerability as compared to the same mRNA formulation prepared without the step of preforming the lipid nanoparticles (e.g., combining the lipids directly with the mRNA). The higher potency and/or efficacy of such a formulation can provide for lower and/or less frequent dosing of the drug product. In some embodiments, the invention features an improved lipid formulation comprising a cationic lipid, a helper lipid and a PEG or PEG-modified lipid.

In some embodiments, the resultant encapsulation efficiencies for the present lipid nanoparticle formulation and preparation method are around 90%. For the delivery of nucleic acids, achieving high encapsulation efficiencies is critical to attain protection of the drug substance and reduce loss of activity in vivo. In addition, a surprising result for the lipid nanoparticle formulation prepared by the novel method in the current invention is the significantly higher transfection efficiency observed in vitro.

Various aspects of the invention are described in detail in the following sections. The use of sections is not meant to limit the invention. Each section can apply to any aspect of the invention.

Messenger RNA (mRNA)

The present invention may be used to encapsulate any mRNA. mRNA is typically thought of as the type of RNA that carries information from DNA to the ribosome. Typically, in eukaryotic organisms, mRNA processing comprises the addition of a "cap" on the 5' end, and a "tail" on the 3' end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The additional of a tail is typically a polyadenylation event whereby a polyadenylyl moiety is added to the 3' end of the mRNA molecule. The presence of this "tail" serves to protect the mRNA from exonuclease degradation. Messenger RNA is translated by the ribosomes into a series of amino acids that make up a protein.

mRNAs may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

In some embodiments, in vitro synthesized mRNA may be purified before formulation and encapsulation to remove undesirable impurities including various enzymes and other reagents used during mRNA synthesis.

The present invention may be used to formulate and encapsulate mRNAs of a variety of lengths. In some embodiments, the present invention may be used to formulate and encapsulate in vitro synthesized mRNA of or greater than about 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, or 20 kb in length. In some embodiments, the present invention may be used to formulate and encapsulate in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length.

The present invention may be used to formulate and encapsulate mRNA that is unmodified or mRNA containing one or more modifications that typically enhance stability. In some embodiments, modifications are selected from modified nucleotides, modified sugar phosphate backbones, and 5' and/or 3' untranslated region.

In some embodiments, modifications of mRNA may include modifications of the nucleotides of the RNA. A modified mRNA according to the invention can include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5'-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine, pseudouridine, 5-methylcytidine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

Typically, mRNA synthesis includes the addition of a "cap" on the 5' end, and a "tail" on the 3' end. The presence of the cap is important in providing resistance to nucleases found in most eukaryotic cells. The presence of a "tail" serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. 2'-O-methylation may also occur at the first base and/or second base following the 7-methyl guanosine triphosphate residues. Examples of cap structures include, but are not limited to, m7GpppNp-RNA, m7GpppNmp-RNA and m7GpppNmpNmp-RNA (where m indicates 2'-Omethyl residues).

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

While mRNA provided from in vitro transcription reactions may be desirable in some embodiments, other sources of mRNA are contemplated as within the scope of the invention including mRNA produced from bacteria, fungi, plants, and/or animals.

The present invention may be used to formulate and encapsulate mRNAs encoding a variety of proteins. Non-limiting examples of mRNAs suitable for the present invention include mRNAs encoding spinal motor neuron 1 (SMN), alpha-galactosidase (GLA), argininosuccinate synthetase (ASS1), ornithine transcarbamylase (OTC), Factor IX (FIX), phenylalanine hydroxylase (PAH), erythropoietin (EPO), cystic fibrosis transmembrane conductance receptor (CFTR) and firefly luciferase (FFL). Exemplary mRNA sequences as disclosed herein are listed below:

Codon-Optimized Human OTC Coding Sequence
(SEQ ID NO: 1)
AUGCUGUUCAACCUUCGGAUCUUGCUGAACAACGCUGCGU
UCCGGAAUGGUCACAACUUCAUGGUCCGGAACUUCAGAUG
CGGCCAGCCGCUCCAGAACAAGGUGCAGCUCAAGGGGAGG
GACCUCCUCACCCUGAAAAACUUCACCGGAGAAGAGAUCA
AGUACAUGCUGUGGCUGUCAGCCGACCUCAAAUUCCGGAU
CAAGCAGAAGGGCGAAUACCUUCCUUUGCUGCAGGGAAAG
UCCCUGGGGAUGAUCUUCGAGAAGCGCAGCACUCGCACUA
GACUGUCAACUGAAACCGGCUUCGCGCUGCUGGGAGGACA
CCCCUGCUUCCUGACCACCCAAGAUAUCCAUCUGGGUGUG
AACGAAUCCCUCACCGACACAGCGCGGGUGCUGUCGUCCA
UGGCAGACGCGGUCCUCGCCCGCGUGUACAAGCAGUCUGA
UCUGGACACUCUGGCCAAGGAAGCCUCCAUUCCUAUCAUU
AAUGGAUUGUCCGACCUCUACCAUCCCAUCCAGAUUCUGG
CCGAUUAUCUGACUCUGCAAGAACAUUACAGCUCCCUGAA
GGGGCUUACCCUUUCGUGGAUCGGCGACGGCAACAACAUU
CUGCACAGCAUUAUGAUGAGCGCUGCCAAGUUUGGAAUGC
ACCUCCAAGCAGCGACCCCGAAGGGAUACGAGCCAGACGC
CUCCGUGACGAAGCUGGCUGAGCAGUACGCCAAGGAGAAC
GGCACUAAGCUGCUGCUCACCAACGACCCUCUCGAAGCCG
CCCACGGUGGCAACGUGCUGAUCACCGAUACCUGGAUCUC
CAUGGGACAGGAGGAGGAAAAGAAGAAGCGCCUGCAAGCA
UUUCAGGGGUACCAGGUGACUAUGAAAACCGCCAAGGUCG
CCGCCUCGGACUGGACCUUCUUGCACUGUCUGCCCAGAAA
GCCCGAAGAGGUGGACGACGAGGUGUUCUACAGCCCGCGG
UCGCUGGUCUUUCCGGAGGCCGAAAACAGGAAGUGGACUA
UCAUGGCCGUGAUGGUGUCCCUGCUGACCGAUUACUCCCC
GCAGCUGCAGAAACCAAAGUUCUGA Codon-Optimized Human ASSI Coding Sequence
(SEQ ID NO: 2)
AUGAGCAGCAAGGGCAGCGUGGUGCUGGCCUACAGCGGCG
GCCUGGACACCAGCUGCAUCCUGGUGUGGCUGAAGGAGCA -continued GGGCUACGACGUGAUCGCCUACCUGGCCAACAUCGGCCAG
AAGGAGGACUUCGAGGAGGCCCGCAAGAAGGCCCUGAAGC
UGGGCGCCAAGAAGGUGUUCAUCGAGGACGUGAGCCGCGA
GUUCGUGGAGGAGUUCAUCUGGCCCGCCAUCCAGAGCAGC
GCCCUGUACGAGGACCGCUACCUGCUGGGCACCAGCCUGG
CCCGCCCCUGCAUCGCCCGCAAGCAGGUGGAGAUCGCCCA
GCGCGAGGGCGCCAAGUACGUGAGCCACGGCGCCACCGGC
AAGGGCAACGACCAGGUGCGCUUCGAGCUGAGCUGCUACA
GCCUGGCCCCCCAGAUCAAGGUGAUCGCCCCCUGGCGCAU
GCCCGAGUUCUACAACCGCUUCAAGGGCCGCAACGACCUG
AUGGAGUACGCCAAGCAGCACGGCAUCCCCAUCCCCGUGA
CCCCCAAGAACCCCUGGAGCAUGGACGAGAACCUGAUGCA
CAUCAGCUACGAGGCCGGCAUCCUGGAGAACCCCAAGAAC
CAGGCCCCCCCCGGCCUGUACACCAAGACCCAGGACCCCG
CCAAGGCCCCCAACACCCCCGACAUCCUGGAGAUCGAGUU
CAAGAAGGGCGUGCCCGUGAAGGUGACCAACGUGAAGGAC
GGCACCACCCACCAGACCAGCCUGGAGCUGUUCAUGUACC
UGAACGAGGUGGCCGGCAAGCACGGCGUGGGCCGCAUCGA
CAUCGUGGAGAACCGCUUCAUCGGCAUGAAGAGCCGCGGC
AUCUACGAGACCCCCGCCGGCACCAUCCUGUACCACGCCC
ACCUGGACAUCGAGGCCUUCACCAUGGACCGCGAGGUGCG
CAAGAUCAAGCAGGGCCUGGGCCUGAAGUUCGCCGAGCUG
GUGUACACCGGCUUCUGGCACAGCCCCGAGUGCGAGUUCG
UGCGCCACUGCAUCGCCAAGAGCCAGGAGCGCGUGGAGGG
CAAGGUGCAGGUGAGCGUGCUGAAGGGCCAGGUGUACAUC
CUGGGCCGCGAGAGCCCCCUGAGCCUGUACAACGAGGAGC
UGGUGAGCAUGAACGUGCAGGGCGACUACGAGCCCACCGA
CGCCACCGGCUUCAUCAACAUCAACAGCCUGCGCCUGAAG
GAGUACCACCGCCUGCAGAGCAAGGUGACCGCCAAGUGA Codon-Optimized Human CFTR Coding Sequence
(SEQ ID NO: 3)
AUGCAACGCUCUCCUCUUGAAAAGGCCUCGGUGGUGUCCA
AGCUCUUCUUCUCGUGGACUAGACCCAUCCUGAGAAAGGG
GUACAGACAGCGCUUGGAGCUGUCCGAUAUCUAUCAAAUC
CCUUCCGUGGACUCCGCGGACAACCUGUCCGAGAAGCUCG
AGAGAGAAUGGGACAGAGAACUCGCCUCAAAGAAGAACCC
GAAGCUGAUUAAUGCGCUUAGGCGGUGCUUUUUCUGGCGG
UUCAUGUUCUACGGCAUCUUCCUCUACCUGGGAGAGGUCA
CCAAGGCCGUGCAGCCCCUGUUGCUGGGACGGAUUAUUGC
CUCCUACGACCCCGACAACAAGGAAGAAAGAAGCAUCGCU
AUCUACUUGGGCAUCGGUCUGUGCCUGCUUUUCAUCGUCC -continued

GGACCCUCUUGUUGCAUCCUGCUAUUUUCGGCCUGCAUCA

CAUUGGCAUGCAGAUGAGAAUUGCCAUGUUUUCCCUGAUC

UACAAGAAAACUCUGAAGCUCUCGAGCCGCGUGCUUGACA

AGAUUUCCAUCGGCCAGCUCGUGUCCCUGCUCUCCAACAA

UCUGAACAAGUUCGACGAGGGCCUCGCCCUGGCCCACUUC

GUGUGGAUCGCCCCUCUGCAAGUGGCGCUUCUGAUGGGCC

UGAUCUGGGAGCUGCUGCAAGCCUCGGCAUUCUGUGGGCU

UGGAUUCCUGAUCGUGCUGGCACUGUUCCAGGCCGGACUG

GGGCGGAUGAUGAUGAAGUACAGGGACCAGAGAGCCGGAA

AGAUUUCCGAACGGCUGGUGAUCACUUCGGAAAUGAUCGA

AAACAUCCAGUCAGUGAAGGCCUACUGCUGGGAAGAGGCC

AUGGAAAAGAUGAUUGAAAACCUCCGGCAAACCGAGCUGA

AGCUGACCCGCAAGGCCGCUUACGUGCGCUAUUUCAACUC

GUCCGCUUUCUUCUUCUCCGGGUUCUUCGUGGUGUUUCUC

UCCGUGCUCCCCUACGCCCUGAUUAAGGGAAUCAUCCUCA

GGAAGAUCUUCACCACCAUUUCCUUCUGUAUCGUGCUCCG

CAUGGCCGUGACCCGGCAGUUCCCAUGGGCCGUGCAGACU

UGGUACGACUCCCUGGGAGCCAUUAACAAGAUCCAGGACU

UCCUUCAAAAGCAGGAGUACAAGACCCUCGAGUACAACCU

GACUACUACCGAGGUCGUGAUGGAAAACGUCACCGCCUUU

UGGGAGGAGGGAUUUGGCGAACUGUUCGAGAAGGCCAAGC

AGAACAACAACAACCGCAAGACCUCGAACGGUGACGACUC

CCUCUUCUUUUCAAACUUCAGCCUGCUCGGGACGCCCGUG

CUGAAGGACAUUAACUUCAAGAUCGAAAGAGGACAGCUCC

UGGCGGUGGCCGGAUCGACCGGAGCCGGAAAGACUUCCCU

GCUGAUGGUGAUCAUGGGAGAGCUUGAACCUAGCGAGGGA

AAGAUCAAGCACUCCGGCCGCAUCAGCUUCUGUAGCCAGU

UUUCCUGGAUCAUGCCCGGAACCAUUAAGGAAAACAUCAU

CUUCGGCGUGUCCUACGAUGAAUACCGCUACCGGUCCGUG

AUCAAAGCCUGCCAGCUGGAAGAGGAUAUUUCAAAGUUCG

CGGAGAAAGAUAACAUCGUGCUGGGCGAAGGGGGUAUUAC

CUUGUCGGGGGGCCAGCGGGCUAGAAUCUCGCUGGCCAGA

GCCGUGUAUAAGGACGCCGACCUGUAUCUCCUGGACUCCC

CCUUCGGAUACCUGGACGUCCUGACCGAAAAGGAGAUCUU

CGAAUCGUGCGUGUGCAAGCUGAUGGCUAACAAGACUCGC

AUCCUCGUGACCUCCAAAAUGGAGCACCUGAAGAAGGCAG

ACAAGAUUCUGAUUCUGCAUGAGGGGUCCUCCUACUUUUA

CGGCACCUUCUCGGAGUUGCAGAACUUGCAGCCCGACUUC

UCAUCGAAGCUGAUGGGUUGCGACAGCUUCGACCAGUUCU

CCGCCGAAAGAAGGAACUCGAUCCUGACGGAAACCUUGCA

CCGCUUCUCUUUGGAAGGCGACGCCCCUGUGUCAUGGACC

-continued

GAGACUAAGAAGCAGAGCUUCAAGCAGACCGGGGAAUUCG

GCGAAAAGAGGAAGAACAGCAUCUUGAACCCCAUUAACUC

CAUCCGCAAGUUCUCAAUCGUGCAAAAGACGCCACUGCAG

AUGAACGGCAUUGAGGAGGACUCCGACGAACCCCUUGAGA

GGCGCCUGUCCCUGGUGCCGGACAGCGAGCAGGGAGAAGC

CAUCCUGCCUCGGAUUUCCGUGAUCUCCACUGGUCCGACG

CUCCAAGCCCGGCGGCGGCAGUCCGUGCUGAACCUGAUGA

CCCACAGCGUGAACCAGGGCCAAAACAUUCACCGCAAGAC

UACCGCAUCCACCCGGAAAGUGUCCCUGGCACCUCAAGCG

AAUCUUACCGAGCUCGACAUCUACUCCCGGAGACUGUCGC

AGGAAACCGGGCUCGAAAUUUCCGAAGAAAUCAACGAGGA

GGAUCUGAAAGAGUGCUUCUUCGACGAUAUGGAGUCGAUA

CCCGCCGUGACGACUUGGAACACUUAUCUGCGGUACAUCA

CUGUGCACAAGUCAUUGAUCUUCGUGCUGAUUUGGUGCCU

GGUGAUUUUCCUGGCCGAGGUCGCGGCCUCACUGGUGGUG

CUCUGGCUGUUGGGAAACACGCCUCUGCAAGACAAGGGAA

ACUCCACGCACUCGAGAAACAACAGCUAUGCCGUGAUUAU

CACUUCCACCUCCUCUUAUUACGUGUUCUACAUCUACGUC

GGAGUGGCGGAUACCCUGCUCGCGAUGGGUUUCUUCAGAG

GACUGCCGCUGGUCCACACCUUGAUCACCGUCAGCAAGAU

UCUUCACCACAAGAUGUUGCAUAGCGUGCUGCAGGCCCCC

AUGUCCACCCUCAACACUCUGAAGGCCGGAGGCAUUCUGA

ACAGAUUCUCCAAGGACAUCGCUAUCCUGGACGAUCUCCU

GCCGCUUACCAUCUUUGACUUCAUCCAGCUGCUGCUGAUC

GUGAUUGGAGCAAUCGCAGUGGUGGCGGUGCUGCAGCCUU

ACAUUUUCGUGGCCACUGUGCCGGUCAUUGUGGCGUUCAU

CAUGCUGCGGGCCUACUUCCUCCAAACCAGCCAGCAGCUG

AAGCAACUGGAAUCCGAGGGACGAUCCCCCAUCUUCACUC

ACCUUGUGACGUCGUUGAAGGGACUGUGGACCCUCCGGGC

UUUCGGACGGCAGCCCUACUUCGAAACCCUCUUCCACAAG

GCCCUGAACCUCCACACCGCCAAUUGGUUCCUGUACCUGU

CCACCCUGCGGUGGUUCCAGAUGCGCAUCGAGAUGAUUUU

CGUCAUCUUCUUCAUCGCGGUCACAUUCAUCAGCAUCCUG

ACUACCGGAGAGGGAGAGGGACGGGUCGGAAUAAUCCUGA

CCCUCGCCAUGAACAUUAUGAGCACCCUGCAGUGGGCAGU

GAACAGCUCGAUCGACGUGGACAGCCUGAUGCGAAGCGUC

AGCCGCGUGUUCAAGUUCAUCGACAUGCCUACUGAGGGAA

AACCCACUAAGUCCACUAAGCCCUACAAAAAUGGCCAGCU

GAGCAAGGUCAUGAUCAUCGAAAACUCCCACGUGAAGAAG

GACGAUAUUUGGCCCUCCGGAGGUCAAAUGACCGUGAAGG

-continued

ACCUGACCGCAAAGUACACCGAGGGAGGAAACGCCAUUCU

CGAAAACAUCAGCUUCUCCAUUUCGCCGGGACAGCGGGUC

GGCCUUCUCGGGCGGACCGGUUCCGGGAAGUCAACUCUGC

UGUCGGCUUUCCUCCGGCUGCUGAAUACCGAGGGGGAAAU

CCAAAUUGACGGCGUGUCUUGGGAUUCCAUUACUCUGCAG

CAGUGGCGGAAGGCCUUCGGCGUGAUCCCCCAGAAGGUGU

UCAUCUUCUCGGGUACCUUCCGGAAGAACCUGGAUCCUUA

CGAGCAGUGGAGCGACCAAGAAAUCUGGAAGGUCGCCGAC

GAGGUCGGCCUGCGCUCCGUGAUUGAACAAUUUCCUGGAA

AGCUGGACUUCGUGCUCGUCGACGGGGGAUGUGUCCUGUC

GCACGGACAUAAGCAGCUCAUGUGCCUCGCACGGUCCGUG

CUCUCCAAGGCCAAGAUUCUGCUGCUGGACGAACCUUCGG

CCCACCUGGAUCCGGUCACCUACCAGAUCAUCAGGAGGAC

CCUGAAGCAGGCCUUUGCCGAUUGCACCGUGAUUCUCUGC

GAGCACCGCAUCGAGGCCAUGCUGGAGUGCCAGCAGUUCC

UGGUCAUCGAGGAGAACAAGGUCCGCCAAUACGACUCCAU

UCAAAAGCUCCUCAACGAGCGGUCGCUGUUCAGACAAGCU

AUUUCACCGUCCGAUAGAGUGAAGCUCUUCCCGCAUCGGA

ACAGCUCAAAGUGCAAAUCGAAGCCGCAGAUCGCAGCCUU

GAAGGAAGAGACUGAGGAAGAGGUGCAGGACACCCGGCUU

UAA

Comparison Codon-Optimized Human CFTR mRNA Coding Sequence (SEQ ID NO: 4)

AUGCAGCGGUCCCCGCUCGAAAAGGCCAGUGUCGUGUCCA

AACUCUUCUUCUCAUGGACUCGGCCUAUCCUUAGAAAGGG

GUAUCGGCAGAGGCUUGAGUUGUCUGACAUCUACCAGAUC

CCCUCGGUAGAUUCGGCGGAUAACCUCUCGGAGAAGCUCG

AACGGGAAUGGGACCGCGAACUCGCGUCUAAGAAAAACCC

GAAGCUCAUCAACGCACUGAGAAGGUGCUUCUUCUGGCGG

UUCAUGUUCUACGGUAUCUUCUUGUAUCUCGGGGAGGUCA

CAAAAGCAGUCCAACCCCUGUUGUUGGGUCGCAUUAUCGC

CUCGUACGACCCCGAUAACAAAGAAGAACGGAGCAUCGCG

AUCUACCUCGGGAUCGGACUGUGUUUGCUUUUCAUCGUCA

GAACACUUUUGUUGCAUCCAGCAAUCUUCGGCCUCCAUCA

CAUCGGUAUGCAGAUGCGAAUCGCUAUGUUUAGCUUGAUC

UACAAAAAGACACUGAAACUCUCGUCGCGGGUGUUGGAUA

AGAUUUCCAUCGGUCAGUUGGUGUCCCUGCUUAGUAAUAA

CCUCAACAAAUUCGAUGAGGGACUGGCGCUGGCACAUUUC

GUGUGGAUUGCCCCGUUGCAAGUCGCCCUUUUGAUGGGCC

UUAUUUGGGAGCUGUUGCAGGCAUCUGCCUUUUGUGGCCU

GGGAUUUCUGAUUGUGUUGGCAUUGUUUCAGGCUGGGCUU

-continued

GGGCGGAUGAUGAUGAAGUAUCGCGACCAGAGAGCGGGUA

AAAUCUCGGAAAGACUCGUCAUCACUUCGGAAAUGAUCGA

AAACAUCCAGUCGGUCAAAGCCUAUUGCUGGGAAGAAGCU

AUGGAGAAGAUGAUUGAAAACCUCCGCCAAACUGAGCUGA

AACUGACCCGCAAGGCGGCGUAUGUCCGGUAUUUCAAUUC

GUCAGCGUUCUUCUUUUCCGGGUUCUUCGUUGUCUUUCUC

UCGGUUUUGCCUUAUGCCUUGAUUAAGGGGAUUAUCCUCC

GCAAGAUUUUCACCACGAUUUCGUUCUGCAUUGUAUUGCG

CAUGGCAGUGACACGGCAAUUUCCGUGGGCCGUGCAGACA

UGGUAUGACUCGCUUGGAGCGAUCAACAAAAUCCAAGACU

UCUUGCAAAAGCAAGAGUACAAGACCCUGGAGUACAAUCU

UACUACUACGGAGGUAGUAAUGGAGAAUGUGACGGCUUUU

UGGGAAGAGGGUUUUGGAGAACUGUUUGAGAAAGCAAAGC

AGAAUAACAACAACCGCAAGACCUCAAAUGGGGACGAUUC

CCUGUUUUUCUCGAACUUCUCCCUGCUCGGAACACCCGUG

UUGAAGGACAUCAAUUUCAAGAUUGAGAGGGGACAGCUUC

UCGCGGUAGCGGGAAGCACUGGUGCGGGAAAAACUAGCCU

CUUGAUGGUGAUUAUGGGGGAGCUUGAGCCCAGCGAGGGG

AAGAUUAAACACUCCGGGCGUAUCUCAUUCUGUAGCCAGU

UUUCAUGGAUCAUGCCCGGAACCAUUAAAGAGAACAUCAU

UUUCGGAGUAUCCUAUGAUGAGUACCGAUACAGAUCGGUC

AUUAAGGCGUGCCAGUUGGAAGAGGACAUUUCUAAGUUCG

CCGAGAAGGAUAACAUCGUCUUGGGAGAAGGGGGUAUUAC

AUUGUCGGGAGGGCAGCGAGCGCGGAUCAGCCUCGCGAGA

GCGGUAUACAAAGAUGCAGAUUUGUAUCUGCUUGAUUCAC

CGUUUGGAUACCUCGACGUAUUGACAGAAAAAGAAAUCUU

CGAGUCGUGCGUGUGUAAACUUAUGGCUAAUAAGACGAGA

AUCCUGGUGACAUCAAAAAUGGAACACCUUAAGAAGGCGG

ACAAGAUCCUGAUCCUCCACGAAGGAUCGUCCUACUUUUA

CGGCACUUUCUCAGAGUUGCAAAACUUGCAGCCGGACUUC

UCAAGCAAACUCAUGGGGUGUGACUCAUUCGACCAGUUCA

GCGCGGAACGGCGGAACUCGAUCUUGACGGAAACGCUGCA

CCGAUUCUCGCUUGAGGGUGAUGCCCCGGUAUCGUGGACC

GAGACAAAGAAGCAGUCGUUUAAGCAGACAGGAGAAUUUG

GUGAGAAAAGAAAGAACAGUAUCUUGAAUCCUAUUAACUC

AAUUCGCAAGUUCUCAAUCGUCCAGAAAACUCCACUGCAG

AUGAAUGGAAUUGAAGAGGAUUCGGACGAACCCCUGGAGC

GCAGGCUUAGCCUCGUGCCGGAUUCAGAGCAAGGGGAGGC

CAUUCUUCCCCGGAUUUCGGUGAUUUCAACCGGACCUACA

CUUCAGGCGAGGCGAAGGCAAUCCGUGCUCAACCUCAUGA

CGCAUUCGGUAAACCAGGGGCAAAACAUUCACCGCAAAAC

-continued

GACGGCCUCAACGAGAAAAGUGUCACUUGCACCCCAGGCG

AAUUUGACUGAACUCGACAUCUACAGCCGUAGGCUUUCGC

AAGAAACCGGACUUGAGAUCAGCGAAGAAAUCAAUGAAGA

AGAUUUGAAAGAGUGUUUCUUUGAUGACAUGGAAUCAAUC

CCAGCGGUGACAACGUGGAACACAUACUUGCGUUACAUCA

CGGUGCACAAGUCCUUGAUUUUCGUCCUCAUCUGGUGUCU

CGUGAUCUUUCUCGCUGAGGUCGCAGCGUCACUUGUGGUC

CUCUGGCUGCUUGGUAAUACGCCCUUGCAAGACAAAGGCA

AUUCUACACACUCAAGAAACAAUUCCUAUGCCGUGAUUAU

CACUUCUACAAGCUCGUAUUACGUGUUUUACAUCUACGUA

GGAGUGGCCGACACUCUGCUCGCGAUGGGUUUCUUCCGAG

GACUCCCACUCGUUCACACGCUUAUCACUGUCUCCAAGAU

UCUCCACCAUAAGAUGCUUCAUAGCGUACUGCAGGCUCCC

AUGUCCACCUUGAAUACGCUCAAGGCGGGAGGUAUUUUGA

AUCGCUUCUCAAAAGAUAUUGCAAUUUUGGAUGACCUUCU

GCCCCUGACGAUCUUCGACUUCAUCCAGUUGUUGCUGAUC

GUGAUUGGGGCUAUUGCAGUAGUCGCUGUCCUCCAGCCUU

ACAUUUUUGUCGCGACCGUUCCGGUGAUCGUGGCGUUUAU

CAUGCUGCGGGCCUAUUUCUUGCAGACGUCACAGCAGCUU

AAGCAACUGGAGUCUGAAGGGAGGUCGCCUAUCUUUACGC

AUCUUGUGACCAGUUUGAAGGGAUUGUGGACGUUGCGCGC

CUUUGGCAGGCAGCCCUACUUUGAAACACUGUUCCACAAA

GCGCUGAAUCUCCAUACGGCAAAUUGGUUUUUGUAUUUGA

GUACCCUCCGAUGGUUUCAGAUGCGCAUUGAGAUGAUUUU

UGUGAUCUUCUUUAUCGCGGUGACUUUUAUCUCCAUCUUG

ACCACGGGAGAGGGCGAGGGACGGGUCGGUAUUAUCCUGA

CACUCGCCAUGAACAUUAUGAGCACUUUGCAGUGGGCAGU

GAACAGCUCGAUUGAUGUGGAUAGCCUGAUGAGGUCCGUU

UCGAGGGUCUUUAAGUUCAUCGACAUGCCGACGGAGGGAA

AGCCCACAAAAAGUACGAAACCCUAUAAGAAUGGGCAAUU

GAGUAAGGUAAUGAUCAUCGAGAACAGUCACGUGAAGAAG

GAUGACAUCUGGCCUAGCGGGGGUCAGAUGACCGUGAAGG

ACCUGACGGCAAAAUACACCGAGGGAGGGAACGCAAUCCU

UGAAAACAUCUCGUUCAGCAUUAGCCCCGGUCAGCGUGUG

GGGUUGCUCGGGAGGACCGGGUCAGGAAAAUCGACGUUGC

UGUCGGCCUUCUUGAGACUUCUGAAUACAGAGGGUGAGAU

CCAGAUCGACGGCGUUUCGUGGGAUAGCAUCACCUUGCAG

CAGUGGCGGAAAGCGUUUGGAGUAAUCCCCCAAAAGGUCU

UUAUCUUUAGCGGAACCUUCCGAAAGAAUCUCGAUCCUUA

UGAACAGUGGUCAGAUCAAGAGAUUUGGAAAGUCGCGGAC

-continued

GAGGUUGGCCUUCGGAGUGUAAUCGAGCAGUUUCCGGGAA

AACUCGACUUUGUCCUUGUAGAUGGGGGAUGCGUCCUGUC

GCAUGGGCACAAGCAGCUCAUGUGCCUGGCGCGAUCCGUC

CUCUCUAAAGCGAAAAUUCUUCUCUUGGAUGAACCUUCGG

CCCAUCUGGACCCGGUAACGUAUCAGAUCAUCAGAAGGAC

ACUUAAGCAGGCGUUUGCCGACUGCACGGUGAUUCUCUGU

GAGCAUCGUAUCGAGGCCAUGCUCGAAUGCCAGCAAUUUC

UUGUCAUCGAAGAGAAUAAGGUCCGCCAGUACGACUCCAU

CCAGAAGCUGCUUAAUGAGAGAUCAUUGUUCCGGCAGGCG

AUUUCACCAUCCGAUAGGGUGAAACUUUUUCCACACAGAA

AUUCGUCGAAGUGCAAGUCCAAACCGCAGAUCGCGGCCUU

GAAAGAAGAGACUGAAGAAGAAGUUCAAGACACGCGUCUU

UAA

Codon-Optimized Human PAH Coding Sequence (SEQ ID NO: 5)

AUGAGCACCGCCGUGCUGGAGAACCCCGGCCUGGGCCGCA

AGCUGAGCGACUUCGGCCAGGAGACCAGCUACAUCGAGGA

CAACUGCAACCAGAACGGCGCCAUCAGCCUGAUCUUCAGC

CUGAAGGAGGAGGUGGGCGCCCUGGCCAAGGUGCUGCGCC

UGUUCGAGGAGAACGACGUGAACCUGACCCACAUCGAGAG

CCGCCCCAGCCGCCUGAAGAAGGACGAGUACGAGUUCUUC

ACCCACCUGGACAAGCGCAGCCUGCCCGCCCUGACCAACA

UCAUCAAGAUCCUGCGCCACGACAUCGGCGCCACCGUGCA

CGAGCUGAGCCGCGACAAGAAGAAGGACACCGUGCCCUGG

UUCCCCCGCACCAUCCAGGAGCUGGACCGCUUCGCCAACC

AGAUCCUGAGCUACGGCGCCGAGCUGGACGCCGACCACCC

CGGCUUCAAGGACCCCGUGUACCGCGCCCGCCGCAAGCAG

UUCGCCGACAUCGCCUACAACUACCGCCACGGCCAGCCCA

UCCCCCGCGUGGAGUACAUGGAGGAGGAGAAGAAGACCUG

GGGCACCGUGUUCAAGACCCUGAAGAGCCUGUACAAGACC

CACGCCUGCUACGAGUACAACCACAUCUUCCCCCUGCUGG

AGAAGUACUGCGGCUUCCACGAGGACAACAUCCCCCAGCU

GGAGGACGUGAGCCAGUUCCUGCAGACCUGCACCGGCUUC

CGCCUGCGCCCCGUGGCCGGCCUGCUGAGCAGCCGCGACU

UCCUGGGCGGCCUGGCCUUCCGCGUGUUCCACUGCACCCA

GUACAUCCGCCACGGCAGCAAGCCCAUGUACACCCCCGAG

CCCGACAUCUGCCACGAGCUGCUGGGCCACGUGCCCCUGU

UCAGCGACCGCAGCUUCGCCCAGUUCAGCCAGGAGAUCGG

CCUGGCCAGCCUGGGCGCCCCCGACGAGUACAUCGAGAAG

CUGGCCACCAUCUACUGGUUCACCGUGGAGUUCGGCCUGU

GCAAGCAGGGCGACAGCAUCAAGGCCUACGGCGCCGGCCU

GCUGAGCAGCUUCGGCGAGCUGCAGUACUGCCUGAGCGAG

-continued

AAGCCCAAGCUGCUGCCCCUGGAGCUGGAGAAGACCGCCA

UCCAGAACUACACCGUGACCGAGUUCCAGCCCCUGUACUA

CGUGGCCGAGAGCUUCAACGACGCCAAGGAGAAGGUGCGC

AACUUCGCCGCCACCAUCCCCCGCCCCUUCAGCGUGCGCU

ACGACCCCUACACCCAGCGCAUCGAGGUGCUGGACAACAC

CCAGCAGCUGAAGAUCCUGGCCGACAGCAUCAACAGCGAG

AUCGGCAUCCUGUGCAGCGCCCUGCAGAAGAUCAAGUAA

In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical SEQ ID NO: 1, SEQ ID NO: 2, SEQ ID NO:3 or SEQ ID NO: 4. In some embodiments, an mRNA suitable for the present invention comprises a nucleotide sequence identical to SEQ ID NO: 1, SEQ ID NO: 2, SEQ ID NO:3 or SEQ ID NO: 4.

mRNA Solution mRNA may be provided in a solution to be mixed with a lipid solution such that the mRNA may be encapsulated in lipid nanoparticles. A suitable mRNA solution may be any aqueous solution containing mRNA to be encapsulated at various concentrations. For example, a suitable mRNA solution may contain an mRNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In some embodiments, a suitable mRNA solution may contain an mRNA at a concentration ranging from about 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml. In some embodiments, a suitable mRNA solution may contain an mRNA at a concentration up to about 5.0 mg/ml, 4.0 mg/ml, 3.0 mg/ml, 2.0 mg/ml, 1.0 mg/ml, 0.09 mg/ml, 0.08 mg/ml, 0.07 mg/ml, 0.06 mg/ml, or 0.05 mg/ml.

Typically, a suitable mRNA solution may also contain a buffering agent and/or salt. Generally, buffering agents can include HEPES, ammonium sulfate, sodium bicarbonate, sodium citrate, sodium acetate, potassium phosphate and sodium phosphate. In some embodiments, suitable concentration of the buffering agent may range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM. In some embodiments, suitable concentration of the buffering agent is or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM.

Exemplary salts can include sodium chloride, magnesium chloride, and potassium chloride. In some embodiments, suitable concentration of salts in an mRNA solution may range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM. Salt concentration in a suitable mRNA solution is or greater than about 1 mM, 5 mM, 10 mM, 20 mM, 30 mM, 40 mM, 50 mM, 60 mM, 70 mM, 80 mM, 90 mM, or 100 mM.

In some embodiments, a suitable mRNA solution may have a pH ranging from about 3.5-6.5, 3.5-6.0, 3.5-5.5., 3.5-5.0, 3.5-4.5, 4.0-5.5, 4.0-5.0, 4.0-4.9, 4.0-4.8, 4.0-4.7, 4.0-4.6, or 4.0-4.5. In some embodiments, a suitable mRNA solution may have a pH of or no greater than about 3.5, 4.0, 4.1, 4.2, 4.3, 4.4, 4.5, 4.6, 4.7, 4.8, 4.9, 5.0, 5.2, 5.4, 5.6, 5.8, 6.0, 6.1, 6.3, and 6.5.

Various methods may be used to prepare an mRNA solution suitable for the present invention. In some embodiments, mRNA may be directly dissolved in a buffer solution described herein. In some embodiments, an mRNA solution may be generated by mixing an mRNA stock solution with a buffer solution prior to mixing with a lipid solution for encapsulation. In some embodiments, an mRNA solution may be generated by mixing an mRNA stock solution with a buffer solution immediately before mixing with a lipid solution for encapsulation. In some embodiments, a suitable mRNA stock solution may contain mRNA in water at a concentration at or greater than about 0.2 mg/ml, 0.4 mg/ml, 0.5 mg/ml, 0.6 mg/ml, 0.8 mg/ml, 1.0 mg/ml, 1.2 mg/ml, 1.4 mg/ml, 1.5 mg/ml, or 1.6 mg/ml, 2.0 mg/ml, 2.5 mg/ml, 3.0 mg/ml, 3.5 mg/ml, 4.0 mg/ml, 4.5 mg/ml, or 5.0 mg/ml.

In some embodiments, an mRNA stock solution is mixed with a buffer solution using a pump. Exemplary pumps include but are not limited to gear pumps, peristaltic pumps and centrifugal pumps.

Typically, the buffer solution is mixed at a rate greater than that of the mRNA stock solution. For example, the buffer solution may be mixed at a rate at least 1×, 2×, 3×, 4×, 5×, 6×, 7×, 8×, 9×, 10×, 15×, or 20× greater than the rate of the mRNA stock solution. In some embodiments, a buffer solution is mixed at a flow rate ranging between about 100-6000 ml/minute (e.g., about 100-300 ml/minute, 300-600 ml/minute, 600-1200 ml/minute, 1200-2400 ml/minute, 2400-3600 ml/minute, 3600-4800 ml/minute, 4800-6000 ml/minute, or 60-420 ml/minute). In some embodiments, a buffer solution is mixed at a flow rate of or greater than about 60 ml/minute, 100 ml/minute, 140 ml/minute, 180 ml/minute, 220 ml/minute, 260 ml/minute, 300 ml/minute, 340 ml/minute, 380 ml/minute, 420 ml/minute, 480 ml/minute, 540 ml/minute, 600 ml/minute, 1200 ml/minute, 2400 ml/minute, 3600 ml/minute, 4800 ml/minute, or 6000 ml/minute.

In some embodiments, an mRNA stock solution is mixed at a flow rate ranging between about 10-600 ml/minute (e.g., about 5-50 ml/minute, about 10-30 ml/minute, about 30-60 ml/minute, about 60-120 ml/minute, about 120-240 ml/minute, about 240-360 ml/minute, about 360-480 ml/minute, or about 480-600 ml/minute). In some embodiments, an mRNA stock solution is mixed at a flow rate of or greater than about 5 ml/minute, 10 ml/minute, 15 ml/minute, 20 ml/minute, 25 ml/minute, 30 ml/minute, 35 ml/minute, 40 ml/minute, 45 ml/minute, 50 ml/minute, 60 ml/minute, 80 ml/minute, 100 ml/minute, 200 ml/minute, 300 ml/minute, 400 ml/minute, 500 ml/minute, or 600 ml/minute.

Lipid Solution

According to the present invention, a lipid solution contains a mixture of lipids suitable to form lipid nanoparticles for encapsulation of mRNA. In some embodiments, a suitable lipid solution is ethanol based. For example, a suitable lipid solution may contain a mixture of desired lipids dissolved in pure ethanol (i.e., 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. For example, a suitable lipid solution may contain a mixture of desired lipids at a total concentration of or greater than about 0.1 mg/ml, 0.5 mg/ml, 1.0 mg/ml, 2.0 mg/ml, 3.0 mg/ml, 4.0 mg/ml, 5.0 mg/ml, 6.0 mg/ml, 7.0 mg/ml, 8.0 mg/ml, 9.0 mg/ml, 10 mg/ml, 15 mg/ml, 20 mg/ml, 30 mg/ml, 40 mg/ml, 50 mg/ml, or 100 mg/ml. In some embodiments, a suitable lipid solution may contain a mixture of desired lipids at a total concentration ranging from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9 mg/ml, 1.0-8 mg/ml, 1.0-7 mg/ml, 1.0-6 mg/ml, or 1.0-5 mg/ml. In some embodiments, a suitable lipid solution may contain a mixture of desired lipids at a total concentration up to about 100 mg/ml, 90 mg/ml, 80 mg/ml, 70 mg/ml, 60 mg/ml, 50 mg/ml, 40 mg/ml, 30 mg/ml, 20 mg/ml, or 10 mg/ml.

Any desired lipids may be mixed at any ratios suitable for encapsulating mRNAs. In some embodiments, a suitable lipid solution contains a mixture of desired lipids including cationic lipids, helper lipids (e.g. non cationic lipids and/or cholesterol lipids) and/or PEGylated lipids. In some embodiments, a suitable lipid solution contains a mixture of desired lipids including one or more cationic lipids, one or more helper lipids (e.g. non cationic lipids and/or cholesterol lipids) and one or more PEGylated lipids.

Cationic Lipids

As used herein, the phrase "cationic lipids" refers to any of a number of lipid species that have a net positive charge at a selected pH, such as physiological pH. Several cationic lipids have been described in the literature, many of which are commercially available. Particularly suitable cationic lipids for use in the compositions and methods of the invention include those described in international patent publications WO 2010/053572 (and particularly, C12-200 described at paragraph [00225]) and WO 2012/170930, both of which are incorporated herein by reference. In certain embodiments, cationic lipids suitable for the compositions and methods of the invention include an ionizable cationic lipid described in U.S. provisional patent application 61/617,468, filed Mar. 29, 2012 (incorporated herein by reference), such as, e.g, (15Z, 18Z)-N,N-dimethyl-6-(9Z, 12Z)-octadeca-9,12-dien-1-yl)tetracosa-15,18-dien-1-amine (HGT5000), (15Z, 18Z)-N,N-dimethyl-6-((9Z, 12Z)-octadeca-9,12-dien-1-yl)tetracosa-4,15,18-trien-1-amine (HGT5001), and (15Z,18Z)-N,N-dimethyl-6-((9Z, 12Z)-octadeca-9,12-dien-1-yl)tetracosa-5,15,18-trien-1-amine (HGT5002).

In some embodiments, cationic lipids suitable for the compositions and methods of the invention include cationic lipids such as 3,6-bis(4-(bis((9Z,12Z)-2-hydroxyoctadeca-9,12-dien-1-yl)amino)butyl)piperazine-2,5-dione (OF-02).

In some embodiments, cationic lipids suitable for the compositions and methods of the invention include a cationic lipid described in WO 2015/184256 A2 entitled "Biodegradable lipids for delivery of nucleic acids" which is incorporated by reference herein such as 3-(4-(bis(2-hydroxydodecyl)amino)butyl)-6-(4-((2-hydroxydodecyl)(2-hydroxyundecyl)amino)butyl)-1,4-dioxane-2,5-dione (Target 23), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione (Target 24).

In some embodiments, cationic lipids suitable for the compositions and methods of the invention include a cationic lipid described in WO 2013/063468 and in U.S. provisional application entitled "Lipid Formulations for Delivery of Messenger RNA", both of which are incorporated by reference herein. In some embodiments, a cationic lipid comprises a compound of formula I-c1-a:

I-c1-a

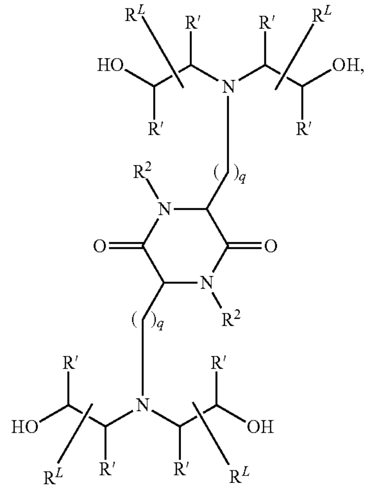

or a pharmaceutically acceptable salt thereof, wherein:

each $R^2$ independently is hydrogen or $C_{1-3}$ alkyl;

each q independently is 2 to 6;

each R' independently is hydrogen or $C_{1-3}$ alkyl;

and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each R L independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ independently is n-$C_{10}$ alkyl.

In some embodiments, each $R^2$ independently is hydrogen or methyl; each q independently is 3 to 5; each R' independently is hydrogen or methyl; and each $R^L$ independently is $C_{8-12}$ alkyl.

In some embodiments, each $R^2$ is hydrogen; each q independently is 3 to 5; each R' is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a cationic lipid comprises a compound of formula I-g:

I-g

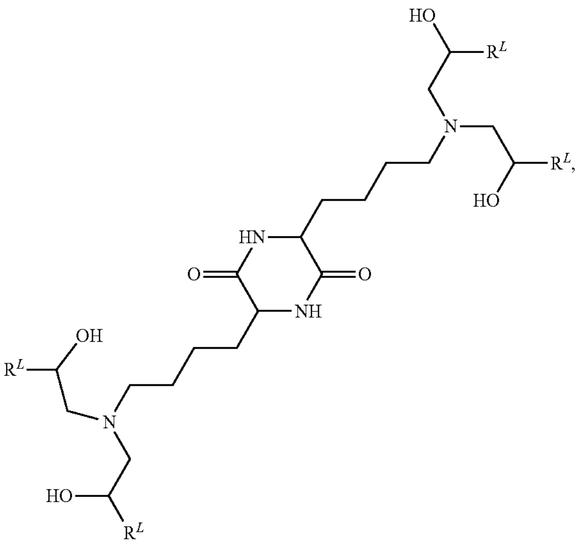

or a pharmaceutically acceptable salt thereof, wherein each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ is n-$C_{10}$ alkyl.

In particular embodiments, a suitable cationic lipid is cKK-E12, or (3,6-bis(4-(bis(2-hydroxydodecyl)amino) butyl)piperazine-2,5-dione). Structure of cKK-E12 is shown below:

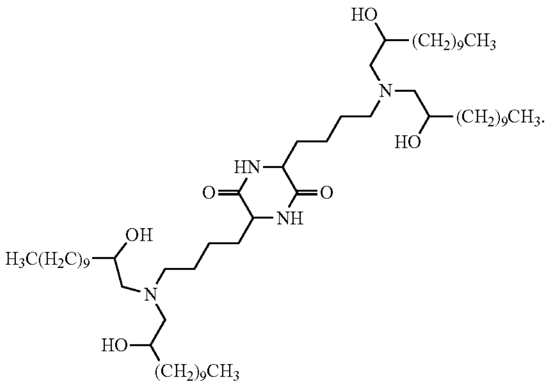

Additional exemplary cationic lipids include those of formula I:

I

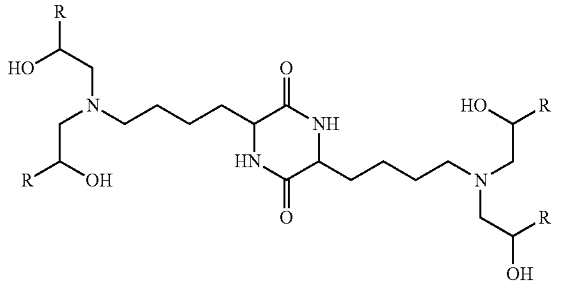

and pharmaceutically acceptable salts thereof, wherein,

R is ("OF-00")

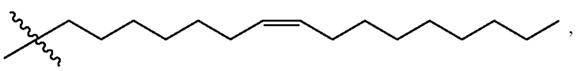

R is ("OF-01")

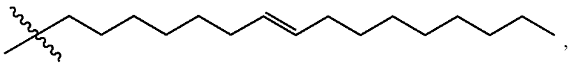

R is ("OF-02")

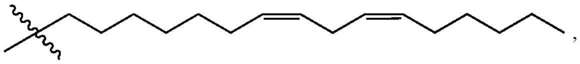

or

R is ("OF-03")

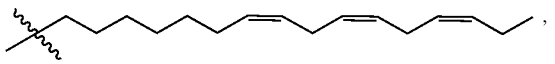

(see, e.g., Fenton, Owen S., et al. "Bioinspired Alkenyl Amino Alcohol Ionizable Lipid Materials for Highly Potent In Vivo mRNA Delivery." *Advanced materials* (2016)).

In some embodiments, one or more cationic lipids suitable for the present invention may be N-[1-(2,3-dioleyloxy) propyl]-N,N,N-trimethylammonium chloride or "DOTMA". (Feigner et al. (Proc. Nat'l Acad. Sci. 84, 7413 (1987); U.S. Pat. No. 4,897,355). Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylarnrnonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethy 1-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-DMA", 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (see, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, one or more cationic lipids may be chosen from XTC (2,2-Dilinoleyl-4-dimethylaminoethyl-[1,3]-dioxolane), MC3 (((6Z,9Z,28Z,31Z)-heptatriaconta-6,9,28,31-tetraen-19-yl4-(dimethylamino)butanoate), ALNY-100 ((3aR,5s,6aS)-N,N-dimethyl-2,2-di((9Z,12Z)-octadeca-9,12-dienyl)tetrahydro-3aH-cyclopenta[d] [1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617,468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869), N1GL, N2GL, V1GL and combinations thereof.

In some embodiments, the one or more cationic lipids are amino lipids. Amino lipids suitable for use in the invention include those described in WO2017180917, which is hereby incorporated by reference. Exemplary aminolipids in WO2017180917 include those described at paragraph [0744] such as DLin-MC3-DMA (MC3), (13Z,16Z)-N,N-dimethyl-3-nonyldocosa-13,16-dien-1-amine (L608), and Compound 18. Other amino lipids include Compound 2, Compound 23, Compound 27, Compound 10, and Compound 20. Further amino lipids suitable for use in the invention include those described in WO2017112865, which is hereby incorporated by reference. Exemplary amino lipids in WO2017112865 include a compound according to one of formulae (I), (Ia1)-(Ia6), (lb), (II), (IIa), (III), (IIia), (IV), (17-1), (19-1), (19-11), and (20-1), and compounds of paragraphs [00185], [00201], [0276]. In some embodiments, cationic lipids suitable for use in the invention include those described in WO2016118725, which is hereby incorporated by reference. Exemplary cationic lipids in WO2016118725 include those such as KL22 and KL25. In some embodiments, cationic lipids suitable for use in the invention include those described in WO2016118724, which is hereby incorporated by reference. Exemplary cationic lipids in WO2016118725 include those such as KL10, 1,2-dilinoleyloxy-N,N-dimethylaminopropane (DLin-DMA), and KL25.

In some embodiments, cationic lipids constitute at least about 5%, 10%, 20%, 30%, 35%, 40%, 45%, 50%, 55%, 60%, 65%, or 70% of the total lipids in a suitable lipid solution by weight or by molar. In some embodiments, cationic lipid(s) constitute(s) about 30-70% (e.g., about 30-65%, about 30-60%, about 30-55%, about 30-50%, about 30-45%, about 30-40%, about 35-50%, about 35-45%, or about 35-40%) of the total lipid mixture by weight or by molar.

Non-Cationic/Helper Lipids

As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, non-cationic lipids may constitute at least about 5%, 10%, 15%, 20%, 25%, 30%, 35%, 40%, 45%, 50%, 55%, 60%, 65% or 70% of the total lipids in a suitable lipid solution by weight or by molar. In some embodiments, non-cationic lipid(s) constitute(s) about 30-50% (e.g., about 30-45%, about 30-40%, about 35-50%, about 35-45%, or about 35-40%) of the total lipids in a suitable lipid solution by weight or by molar.

Cholesterol-Based Lipids

In some embodiments, a suitable lipid solution includes one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, cholesterol-based lipid(s) constitute(s) at least about 5%, 10%, 20%, 30%, 40%, 50%, 60%, or 70% of the total lipids in a suitable lipid solution by weight or by molar. In some embodiments, cholesterol-based lipid(s) constitute(s) about 30-50% (e.g., about 30-45%, about 30-40%, about 35-50%, about 35-45%, or about 35-40%) of the total lipids in a suitable lipid solution by weight or by molar.

PEGylated Lipids

In some embodiments, a suitable lipid solution includes one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl (Methoxy Polyethylene Glycol)-2000] (C8 PEG-2000 ceramide) is also contemplated by the present invention. Contemplated PEG-modified lipids include, but are not limited to, a polyethylene glycol chain of up to 2 kDa, up to 3 kDa, up to 4 kDa or up to 5 kDa in length covalently attached to a lipid with alkyl chain(s) of $C_6$-$C_{20}$ length. In some embodiments, a PEG-modified or PEGylated lipid is PEGylated cholesterol or PEG-2K. In some embodiments, particularly useful exchangeable lipids are PEG-ceramides having shorter acyl chains (e.g., $C_{14}$ or $C_{18}$).

PEG-modified phospholipid and derivatized lipids may constitute at least about 5%, 10%, 20%, 30%, 40%, 50%, 60%, or 70% of the total lipids in a suitable lipid solution by weight or by molar. In some embodiments, PEGylated lipid lipid(s) constitute(s) about 30-50% (e.g., about 30-45%, about 30-40%, about 35-50%, about 35-45%, or about 35-40%) of the total lipids in a suitable lipid solution by weight or by molar.

Various combinations of lipids, i.e., cationic lipids, non-cationic lipids, PEG-modified lipids and optionally cholesterol, that can used to prepare, and that are comprised in, pre-formed lipid nanoparticles are described in the literature and herein. For example, a suitable lipid solution may contain cKK-E12, DOPE, cholesterol, and DMG-PEG2K; C12-200, DOPE, cholesterol, and DMG-PEG2K; HGT5000, DOPE, cholesterol, and DMG-PEG2K; HGT5001, DOPE, cholesterol, and DMG-PEG2K; cKK-E12, DPPC, cholesterol, and DMG-PEG2K; C12-200, DPPC, cholesterol, and DMG-PEG2K; HGT5000, DPPC, chol, and DMG-PEG2K; HGT5001, DPPC, cholesterol, and DMG-PEG2K; or ICE, DOPE and DMG-PEG2K. Additional combinations of lipids are described in the art, e.g., U.S. Ser. No. 62/420,421 (filed on Nov. 10, 2016), U.S. Ser. No. 62/421,021 (filed on Nov. 11, 2016), U.S. Ser. No. 62/464,327 (filed on Feb. 27, 2017), and PCT Application entitled "Novel ICE-based Lipid Nanoparticle Formulation for Delivery of mRNA," filed on Nov. 10, 2017, the disclosures of which are included here in their full scope by reference. The selection of cationic lipids, non-cationic lipids and/or PEG-modified lipids which comprise the lipid mixture as well as the relative molar ratio of such lipids to each other, is based upon the characteristics of the selected lipid(s) and the nature of the and the characteristics of the mRNA to be encapsulated. Additional considerations include, for example, the saturation of the alkyl chain, as well as the size, charge, pH, pKa, fusogenicity and toxicity of the selected lipid(s). Thus the molar ratios may be adjusted accordingly.

Pre-Formed Nanoparticle Formation and Mixing Process

The present invention is based on the discovery of the surprisingly unexpected effect that mixing empty pre-formed lipid nanoparticles (i.e., lipid nanoparticles formed in the absence of mRNA) and mRNA has on the resulting encapsulated mRNA potency and efficacy.

In some previously disclosed processes, see U.S. patent application Ser. No. 14/790,562 entitled "Encapsulation of messenger RNA", filed Jul. 2, 2015 and its provisional U.S. patent application Ser. No. 62/020,163, filed Jul. 2, 2014, the disclosure of which are hereby incorporated in their entirety, in some embodiments, the previous invention provides a process of encapsulating messenger RNA (mRNA) in lipid nanoparticles by mixing an mRNA solution and a lipid solution, wherein the mRNA solution and/or the lipid solution are heated to a pre-determined temperature greater than ambient temperature prior to mixing, to form lipid nanoparticles that encapsulate mRNA.

The present invention relates to a novel method of formulating mRNA-containing lipid nanoparticles. In the present invention, a novel process for preparing a lipid nanoparticle containing mRNA has been identified, which involves combining pre-formed lipid nanoparticles with mRNA under conditions which, due to the order of addition of such components, the resultant formulated particles show improved potency and efficacy. The mixing of the components is achieved with pump systems which maintain the lipid/mRNA (N/P) ratio constant throughout the process and which also afford facile scale-up. In some embodiments, the process is performed at large scale. For example, in some embodiments, a composition according to the present invention contains at least about 1 mg, 5 mg, 10 mg, 50 mg, 100 mg, 500 mg, or 1000 mg of encapsulated mRNA.

For certain cationic lipid nanoparticle formulations of mRNA, in order to achieve high encapsulation of mRNA, which is essential for protection and delivery of mRNA, the mRNA in citrate buffer has to be heated. In those processes or methods, the heating is required to occur before the formulation process (i.e. heating the separate components) as heating post-formulation (post-formation of nanoparticles) does not increase the encapsulation efficiency of the mRNA in the lipid nanoparticles. In contrast, in some embodiments of the novel processes of the present invention, the order of heating of mRNA does not appear to affect the mRNA encapsulation percentage. In some embodiments, no heating (i.e., maintaining at ambient temperature) of one or more of the solution comprising the pre-formed lipid nanoparticles, the solution comprising the mRNA and the mixed solution comprising the lipid nanoparticle encapsulated mRNA is required to occur before or after the formulation process. This potentially provides a huge advantage for precisely scaling up, as controlled temperature change post-mixing is easier to achieve.

With this novel process, in some embodiments, encapsulating mRNA by using a step of mixing the mRNA with empty (i.e., empty of mRNA) pre-formed lipid nanoparticles (Process B) results in remarkably higher potency as compared to encapsulating mRNA by mixing the mRNA with just the lipid components (i.e., that are not pre-formed into lipid nanoparticles) (Process A). As described in the Examples below, for example in Tables 3 and 4, the potency of any mRNA encapsulated lipid nanoparticles tested is from more than 100% to more than 1000% more potent when prepared by Process B as compared to Process A.

In some embodiments, the empty (i.e., empty of mRNA) lipid nanoparticles without mRNA are formed by mixing a lipid solution containing dissolved lipids in a solvent, and an aqueous/buffer solution. In some embodiments, the solvent can be ethanol. In some embodiments, the aqueous solution can be a citrate buffer.

As used herein, the term "ambient temperature" refers to the temperature in a room, or the temperature which surrounds an object of interest (e.g., a pre-formed empty lipid nanoparticle solution, an mRNA solution, or a lipid nanoparticle solution containing mRNA) without heating or cooling. In some embodiments, the ambient temperature at which one or more of the solutions is maintained is or is less than about 35° C., 30° C., 25° C., 20° C., or 16° C. In some embodiments, the ambient temperature at which one or more of the solutions is maintained ranges from about 15-35° C., about 15-30° C., about 15-25° C., about 15-20° C., about 20-35° C., about 25-35° C., about 30-35° C., about 20-30° C., about 25-30° C. or about 20-25° C. In some embodiments, the ambient temperature at which one or more of the solutions is maintained is 20-25° C.

Therefore, a pre-determined temperature greater than ambient temperature is typically greater than about 25° C. In some embodiments, a pre-determined temperature suitable for the present invention is or is greater than about 30° C., 37° C., 40° C., 45° C., 50° C., 55° C., 60° C., 65° C., or 70° C. In some embodiments, a pre-determined temperature suitable for the present invention ranges from about 25-70° C., about 30-70° C., about 35-70° C., about 40-70° C., about 45-70° C., about 50-70° C., or about 60-70° C. In particular embodiments, a pre-determined temperature suitable for the present invention is about 65° C.

In some embodiments, the mRNA, or pre-formed empty (i.e., empty of mRNA) lipid nanoparticle solution, or both, may be heated to a pre-determined temperature above the ambient temperature prior to mixing. In some embodiments, the mRNA and the pre-formed empty lipid nanoparticle solution are heated to the pre-determined temperature separately prior to the mixing. In some embodiments, the mRNA and the pre-formed empty lipid nanoparticle solution are mixed at the ambient temperature but then heated to the pre-determined temperature after the mixing. In some embodiments, the pre-formed empty lipid nanoparticle solution is heated to the pre-determined temperature and mixed with mRNA at the ambient temperature. In some embodiments, the mRNA solution is heated to the pre-determined temperature and mixed with a pre-formed empty lipid nanoparticle solution at ambient temperature.

In some embodiments, the mRNA solution is heated to the pre-determined temperature by adding an mRNA stock solution that is at ambient temperature to a heated buffer solution to achieve the desired pre-determined temperature.

In some embodiments, the lipid solution containing dissolved lipids, or the aqueous/buffer solution, or both, may be heated to a pre-determined temperature above the ambient temperature prior to mixing. In some embodiments, the lipid solution containing dissolved lipids and the aqueous solution are heated to the pre-determined temperature separately prior to the mixing. In some embodiments, the lipid solution containing dissolved lipids and the aqueous solution are mixed at the ambient temperature but then heated to the pre-determined temperature after the mixing. In some embodiments, the lipid solution containing dissolved lipids is heated to the pre-determined temperature and mixed with an aqueous solution at the ambient temperature. In some embodiments, the aqueous solution is heated to the pre-determined temperature and mixed with a lipid solution containing dissolved lipids at ambient temperature. In some embodiments, no heating of one or more of the solution comprising the pre-formed lipid nanoparticles, the solution comprising the mRNA and the mixed solution comprising the lipid nanoparticle encapsulated mRNA occurs before or after the formulation process.

In some embodiments, the lipid solution and an aqueous or buffer solution may be mixed using a pump. In some embodiments, an mRNA solution and a pre-formed empty lipid nanoparticle solution may be mixed using a pump. As the encapsulation procedure can occur on a wide range of scales, different types of pumps may be used to accommodate desired scale. It is however generally desired to use a pulse-less flow pumps. As used herein, a pulse-less flow pump refers to any pump that can establish a continuous flow with a stable flow rate. Types of suitable pumps may include, but are not limited to, gear pumps and centrifugal pumps. Exemplary gear pumps include, but are not limited to, Cole-Parmer or Diener gear pumps. Exemplary centrifugal pumps include, but are not limited to, those manufactured by Grainger or Cole-Parmer.

An mRNA solution and a pre-formed empty lipid nanoparticle solution may be mixed at various flow rates. Typically, the mRNA solution may be mixed at a rate greater than that of the lipid solution. For example, the mRNA solution may be mixed at a rate at least 1×, 2×, 3×, 4×, 5×, 6×, 7×, 8×, 9×, 10×, 15×, or 20× greater than the rate of the lipid solution.

Suitable flow rates for mixing may be determined based on the scales. In some embodiments, an mRNA solution is mixed at a flow rate ranging from about 40-400 ml/minute, 60-500 ml/minute, 70-600 ml/minute, 80-700 ml/minute, 90-800 ml/minute, 100-900 ml/minute, 110-1000 ml/minute, 120-1100 ml/minute, 1301200 ml/minute, 140-1300 ml/minute, 150-1400 ml/minute, 160-1500 ml/minute, 170-1600 ml/minute, 180-1700 ml/minute, 150-250 ml/minute, 250-500 ml/minute, 500-1000 ml/minute, 1000-2000 ml/minute, 2000-3000 ml/minute, 3000-4000 ml/minute, or 4000-5000 ml/minute. In some embodiments, the mRNA solution is mixed at a flow rate of about 200 ml/minute, about 500 ml/minute, about 1000 ml/minute, about 2000 ml/minute, about 3000 ml/minute, about 4000 ml/minute, or about 5000 ml/minute.

In some embodiments, a lipid solution or a pre-formed lipid nanoparticle solution is mixed at a flow rate ranging from about 25-75 ml/minute, 20-50 ml/minute, 25-75 ml/minute, 30-90 ml/minute, 40-100 ml/minute, 50-110 ml/minute, 75-200 ml/minute, 200-350 ml/minute, 350-500 ml/minute, 500-650 ml/minute, 650-850 ml/minute, or 850-1000 ml/minute. In some embodiments, the lipid solution is mixed at a flow rate of about 50 ml/minute, about 100 ml/minute, about 150 ml/minute, about 200 ml/minute, about 250 ml/minute, about 300 ml/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

Typically, in some embodiments, a lipid solution containing dissolved lipids, and an aqueous or buffer solution are mixed into a solution such that the lipids can form nanoparticles without mRNA (or empty pre-formed lipid nanoparticles). In some embodiments, an mRNA solution and a pre-formed lipid nanoparticle solution are mixed into a solution such that the mRNA becomes encapsulated in the lipid nanoparticle. Such a solution is also referred to as a formulation or encapsulation solution. A suitable formulation or encapsulation solution includes a solvent such as ethanol. For example, a suitable formulation or encapsulation solution includes about 10% ethanol, about 15% ethanol, about 20% ethanol, about 25% ethanol, about 30% ethanol, about 35% ethanol, or about 40% ethanol.

In some embodiments, a suitable formulation or encapsulation solution includes a solvent such as isopropyl alcohol. For example, a suitable formulation or encapsulation solution includes about 10% isopropyl alcohol, about 15% isopropyl alcohol, about 20% isopropyl alcohol, about 25% isopropyl alcohol, about 30% isopropyl alcohol, about 35% isopropyl alcohol, or about 40% isopropyl alcohol.

In some embodiments, a suitable formulation or encapsulation solution includes a solvent such as dimethyl sulfoxide. For example, a suitable formulation or encapsulation solution includes about 10% dimethyl sulfoxide, about 15% dimethyl sulfoxide, about 20% dimethyl sulfoxide, about 25% dimethyl sulfoxide, about 30% dimethyl sulfoxide, about 35% dimethyl sulfoxide, or about 40% dimethyl sulfoxide.

In some embodiments, a suitable formulation or encapsulation solution may also contain a buffering agent or salt. Exemplary buffering agent may include HEPES, ammonium sulfate, sodium bicarbonate, sodium citrate, sodium acetate, potassium phosphate and sodium phosphate. Exemplary salt may include sodium chloride, magnesium chloride, and potassium chloride. In some embodiments, an empty preformed lipid nanoparticle formulation used in making this novel nanoparticle formulation can be stably frozen in 10% trehalose solution.

In some embodiments, an empty (i.e., empty of mRNA) pre-formed lipid nanoparticle formulation used in making this novel nanoparticle formulation can be stably frozen in about 5%, about 10%, about 15%, about 20%, about 25%, about 30%, about 35%, about 40%, about 45%, or about 50% trehalose solution. In some embodiments, addition of mRNA to empty lipid nanoparticles can result in a final formulation that does not require any downstream purification or processing and can be stably stored in frozen form.

In some embodiments, ethanol, citrate buffer, and other destabilizing agents are absent during the addition of mRNA and hence the formulation does not require any further downstream processing. In some embodiments, the lipid nanoparticle formulation prepared by this novel process consists of pre-formed lipid nanoparticles in trehalose solution. The lack of destabilizing agents and the stability of trehelose solution increase the ease of scaling up the formulation and production of mRNA-encapsulated lipid nanoparticles.

Purification

In some embodiments, the empty pre-formed lipid nanoparticles or the lipid nanoparticles containing mRNA are purified and/or concentrated. Various purification methods may be used. In some embodiments, lipid nanoparticles are purified using Tangential Flow Filtration. Tangential flow filtration (TFF), also referred to as cross-flow filtration, is a type of filtration wherein the material to be filtered is passed tangentially across a filter rather than through it. In TFF, undesired permeate passes through the filter, while the desired retentate passes along the filter and is collected downstream. It is important to note that the desired material is typically contained in the retentate in TFF, which is the opposite of what one normally encounters in traditional-dead end filtration.

Depending upon the material to be filtered, TFF is usually used for either microfiltration or ultrafiltration. Microfiltration is typically defined as instances where the filter has a pore size of between 0.05 μm and 1.0 μn, inclusive, while ultrafiltration typically involves filters with a pore size of less than 0.05 μm. Pore size also determines the nominal molecular weight limits (NMWL), also referred to as the molecular weight cut off (MWCO) for a particular filter, with microfiltration membranes typically having NMWLs of greater than 1,000 kilodaltons (kDa) and ultrafiltration filters having NMWLs of between 1 kDa and 1,000 kDa.

A principal advantage of tangential flow filtration is that non-permeable particles that may aggregate in and block the filter (sometimes referred to as "filter cake") during traditional "dead-end" filtration, are instead carried along the surface of the filter. This advantage allows tangential flow filtration to be widely used in industrial processes requiring continuous operation since down time is significantly reduced because filters do not generally need to be removed and cleaned.

Tangential flow filtration can be used for several purposes including concentration and diafiltration, among others. Concentration is a process whereby solvent is removed from a solution while solute molecules are retained. In order to effectively concentrate a sample, a membrane having a NMWL or MWCO that is substantially lower than the molecular weight of the solute molecules to be retained is used. Generally, one of skill may select a filter having a NMWL or MWCO of three to six times below the molecular weight of the target molecule(s).

Diafiltration is a fractionation process whereby small undesired particles are passed through a filter while larger desired nanoparticles are maintained in the retentate without changing the concentration of those nanoparticles in solution. Diafiltration is often used to remove salts or reaction buffers from a solution. Diafiltration may be either continuous or discontinuous. In continuous diafiltration, a diafiltration solution is added to the sample feed at the same rate that filtrate is generated. In discontinuous diafiltration, the solution is first diluted and then concentrated back to the starting concentration. Discontinuous diafiltration may be repeated until a desired concentration of nanoparticles is reached.

Purified and/or concentrated lipid nanoparticles may be formulated in a desired buffer such as, for example, PBS.

Provided Nanoparticles Encapsulating mRNA

A process according to the present invention results in higher potency and efficacy thereby allowing for lower doses thereby shifting the therapeutic index in a positive direction. In some embodiments, the process according to the present invention results in homogeneous and small particle sizes (e.g., less than 150 nm), as well as significantly improved encapsulation efficiency and/or mRNA recovery rate as compared to a prior art process.

Thus, the present invention provides a composition comprising purified nanoparticles described herein. In some embodiments, majority of purified nanoparticles in a composition, i.e., greater than about 50%, 55%, 60%, 65%, 70%, 75%, 80%, 85%, 90%, 95%, 96%, 97%, 98%, or 99% of the purified nanoparticles, have a size of about 150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm). In some embodiments, substantially all of the purified nanoparticles have a size of about 150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm).

In addition, more homogeneous nanoparticles with narrow particle size range are achieved by a process of the present invention. For example, greater than about 70%, 75%, 80%, 85%, 90%, 95%, 96%, 97%, 98%, 99% of the purified nanoparticles in a composition provided by the present invention have a size ranging from about 75-150 nm (e.g., about 75-145 nm, about 75-140 nm, about 75-135 nm, about 75-130 nm, about 75-125 nm, about 75-120 nm, about 75-115 nm, about 75-110 nm, about 75-105 nm, about 75-100 nm, about 75-95 nm, about 75-90 nm, or 75-85 nm). In some embodiments, substantially all of the purified nanoparticles have a size ranging from about 75-150 nm (e.g., about 75-145 nm, about 75-140 nm, about 75-135 nm, about 75-130 nm, about 75-125 nm, about 75-120 nm, about 75-115 nm, about 75-110 nm, about 75-105 nm, about 75-100 nm, about 75-95 nm, about 75-90 nm, or 75-85 nm).

In some embodiments, the dispersity, or measure of heterogeneity in size of molecules (PDI), of nanoparticles in a composition provided by the present invention is less than about 0.23 (e.g., less than about 0.23, 0.22, 0.21, 0.20, 0.19, 0.18, 0.17, 0.16, 0.15, 0.14, 0.13, 0.12, 0.11, 0.10, 0.09, or 0.08). In a particular embodiment, the PDI is less than about 0.16.

In some embodiments, greater than about 75%, 80%, 85%, 90%, 95%, 96%, 97%, 98%, or 99% of the purified lipid nanoparticles in a composition provided by the present invention encapsulate an mRNA within each individual particle. In some embodiments, substantially all of the purified lipid nanoparticles in a composition encapsulate an mRNA within each individual particle.

In some embodiments, a composition according to the present invention contains at least about 1 mg, 5 mg, 10 mg, 100 mg, 500 mg, or 1000 mg of encapsulated mRNA. In some embodiments, a process according to the present invention results in greater than about 60%, 65%, 70%, 75%, 80%, 85%, 90%, 95%, 96%, 97%, 98%, or 99% recovery of mRNA.

In some embodiments, a composition according to the present invention is formulated so as to administer doses to a subject. In some embodiments, a composition of mRNA lipid nanoparticles as described herein is formulated at a dose concentration of less than 1.0 mg/kg mRNA lipid nanoparticles (e.g., 0.6 mg/kg, 0.5 mg/kg, 0.3 mg/kg, 0.016 mg/kg. 0.05 mg/kg, and 0.016 mg/kg. In some embodiments, the dose is decreased due to the unexpected finding that lower doses yield high potency and efficacy. In some embodiments, the dose is decreased by about 70%, 65%, 60%, 55%, 50%, 45% or 40%.

In some embodiments, the potency of mRNA encapsulated lipid nanoparticles produced by Process B is from more than 100% (i.e., more than 200%, more than 300%, more than 400%, more than 500%, more than 600%, more than 700%, more than 800%, or more than 900%) to more than 1000% more potent when prepared by Process B as compared to Process A.

EXAMPLES

While certain compounds, compositions and methods of the present invention have been described with specificity in accordance with certain embodiments, the following examples serve only to illustrate the invention and are not intended to limit the same.

Lipid Materials

The formulations described in the following Examples, unless otherwise specified, contain a multi-component lipid mixture of varying ratios employing one or more cationic lipids, helper lipids (e.g., non-cationic lipids and/or cholesterol lipids) and PEGylated lipids designed to encapsulate various nucleic acid materials, as discussed previously.

Example 1. Lipid Nanoparticle Formulation Process A

This example illustrates an exemplary lipid nanoparticle formulation process for encapsulating mRNA. As used herein, Process A refers to a conventional method of encapsulating mRNA by mixing mRNA with a mixture of lipids, without first pre-forming the lipids into lipid nanoparticles. As compared to Process B described below, Process A does not involve pre-formation of lipid nanoparticles.

An exemplary formulation Process A is shown in FIG. 1. In this process, in some embodiments, the ethanol lipid solution and the aqueous buffered solution of mRNA were prepared separately. A solution of mixture of lipids (cationic lipid, helper lipids, zwitterionic lipids, PEG lipids etc.) was prepared by dissolving lipids in ethanol. The mRNA solution was prepared by dissolving the mRNA in citrate buffer, resulting in mRNA at a concentration of 0.0833 mg/ml in citrate buffer with a pH of 4.5. As shown in FIG. 1, the mixtures were then both heated to 65° C. prior to mixing. Then, these two solutions were mixed using a pump system. In some instances, the two solutions were mixed using a gear pump system. In certain embodiments, the two solutions were mixing using a ‘T’ junction (or “Y” junction). The mixture was then purified by diafiltration with a TFF process. The resultant formulation concentrated and stored at 2-8° C. until further use.

Example 2. Lipid Nanoparticle Formulation Process B with Pre-Formed Lipid Nanoparticles This example illustrates an exemplary Process B for encapsulating mRNA. As used herein, Process B refers to a process of encapsulating messenger RNA (mRNA) by mixing pre-formed lipid nanoparticles with mRNA. A range of different conditions, such as varying temperatures (i.e., heating or not heating the mixture), buffers, and concentrations, may be employed in Process B. The exemplary conditions described in this and other examples are for illustration purposes only.

Figure 2:
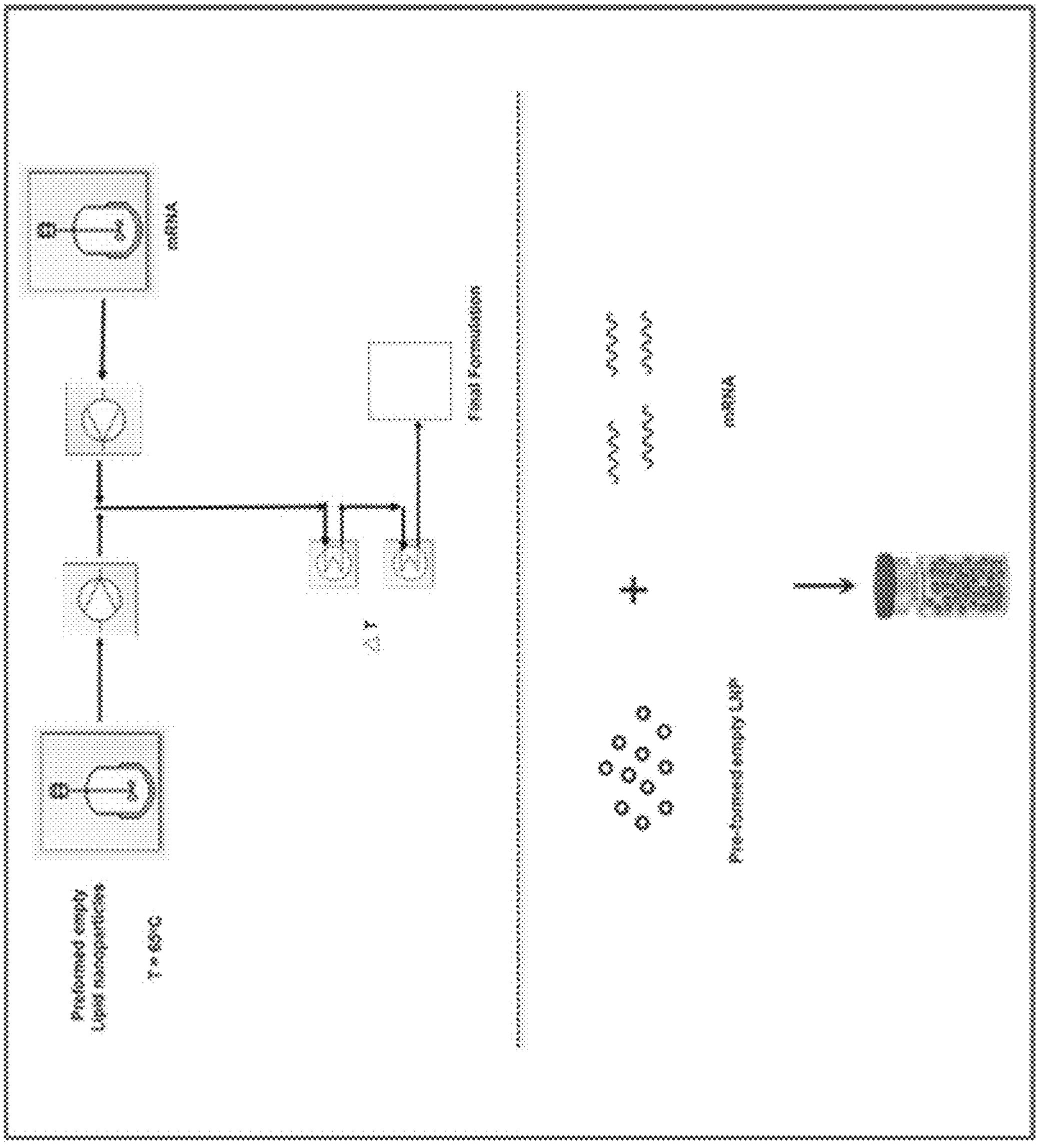
FIG. 2 shows a schematic of an exemplary lipid nanoparticle mRNA encapsulation process (Process B) that involves mixing pre-formed empty lipid nanoparticles with mRNA dissolved in an aqueous buffer, using a pump system.

An exemplary formulation Process B is shown in FIG. 2. In this process, in some embodiments, lipids dissolved in ethanol and citrate buffer were mixed using a pump system. The instantaneous mixing of the two streams resulted in the formation of empty lipid nanoparticles, which was a self-assembly process. The resultant formulation mixture was empty lipid nanoparticles in citrate buffer containing alcohol. The formulation was then subjected to a TFF purification process wherein buffer exchange occurred. The resulting suspension of pre-formed empty lipid nanoparticles was then mixed with mRNA using a pump system. For certain cationic lipids, heating the solution post-mixing resulted in a higher percentage of lipid nanoparticles containing mRNA and a higher total yield of mRNA.

In addition, the effects of the presence of citrate buffer during the addition of mRNA in the Process B were studied. Table 1 shows exemplary encapsulation efficiencies for lipid nanoparticle formulation Process B with and without citrate buffer (pH 4.5). Decreases in the encapsulation efficiency of mRNA were observed when citrate buffer was present during the mixing of pre-formed empty lipid nanoparticles and mRNA. In the presence of citrate buffer, the encapsulation efficiencies for the lipid nanoparticle formulation Process B were less than 60%. The encapsulation efficiencies for the lipid nanoparticle formulation prepared by Process B without citrate buffer were around or above 90%.

TABLE 1

Encapsulation efficiencies for lipid nanoparticle formulation using Process B with and without citrate buffer.

| Formulation | Lipid nanoparticle formulation - Process B in the absence of citrate buffer | Lipid nanoparticle formulation - Process B in the presence of citrate buffer |
|---|---|---|
| 1 | 96 | 56 |
| 2 | 94 | 48 |
| 3 | 90 | 52 |
| 4 | 93 | 51 |

Example 3. In Vivo Activity of the Expressed hOTC in spf$^{ash}$ Mice

This example illustrates that mRNA delivered via lipid nanoparticles produced by Process B were unexpectedly more effective than those produced by Process A.

In this example, OTC spf$^{ash}$ mice were administered a single 0.5 mg/kg dose of hOTC mRNA encapsulated in lipid nanoparticles prepared by Process A or Process B. The liver tissues from these mice were analyzed 24 hours after administration for citrulline production. The formulations were first tested directly after mixing without storing, as well as tested after the mixture of the formulation was stored for a period of 2.5 months at −80° C.

Figure 3:
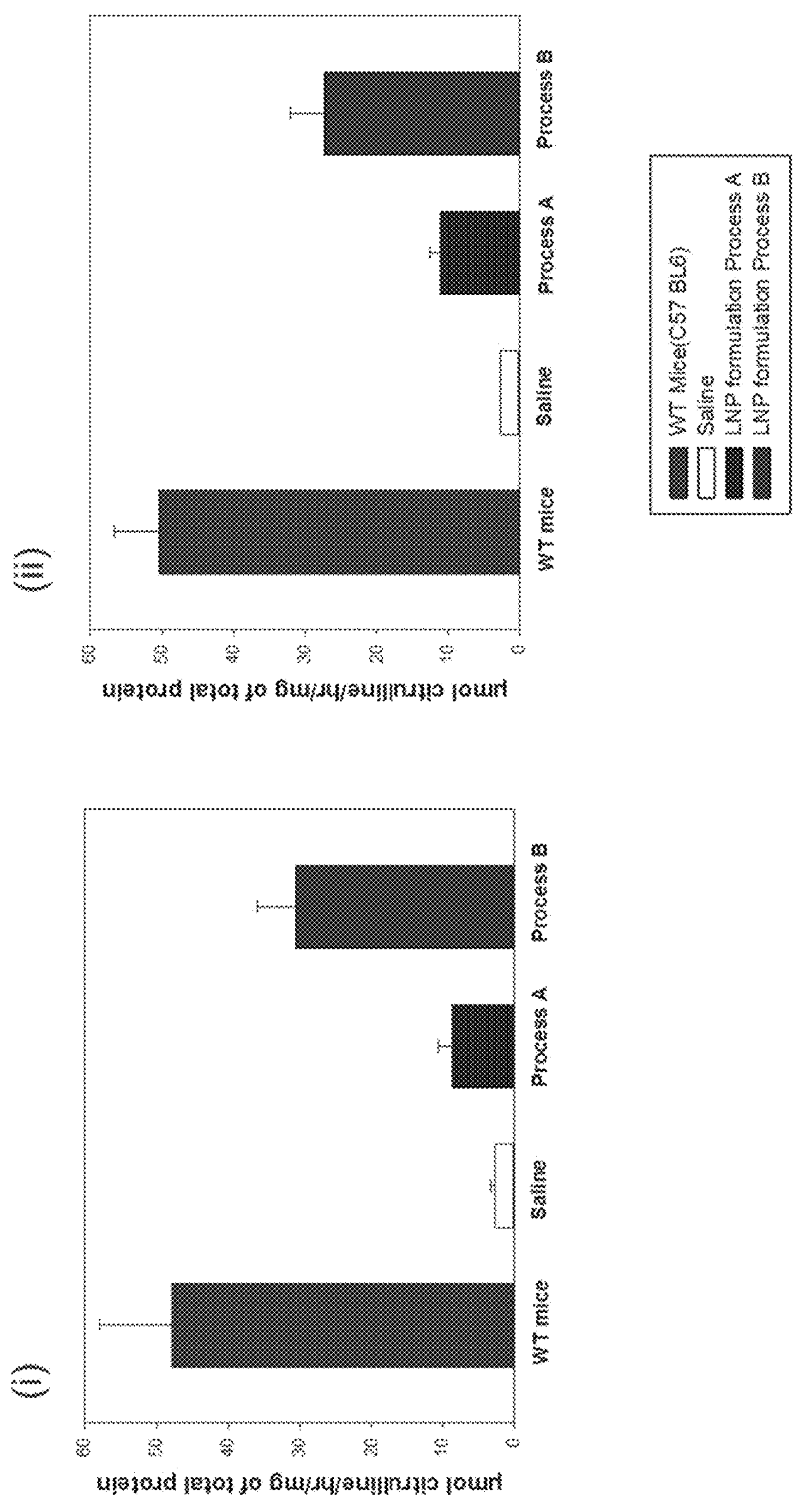
FIG. 3 depicts exemplary activity of expressed human ornithine transcarbamylase (hOTC) protein (in terms of citrulline production) in livers of OTC spf$^{ash}$ mice 24 hours after a single 0.5 mg/kg dose of hOTC mRNA encapsulated in lipid nanoparticle formulations made by Process A or Process B. Before use, lipid nanoparticle formulations made by Process A and Process B were stored in the frozen form at −80° C. for (i) T=0 months (fresh without freezing), or (ii) T=2.5 months.

FIG. 3 depicts exemplary activity of expressed hOTC protein (in terms of citrulline production) in livers of OTC spf$^{ash}$ mice 24 hours after a single 0.5 mg/kg dose of hOTC mRNA encapsulated in lipid nanoparticle formulations made by Process A or Process B.

Generally, the production of citrulline can be used to evaluate the activity of the expressed hOTC protein. As shown in FIG. 3, citrulline activity due to expressed hOTC protein in OTC spf$^{ash}$ mice liver was measured 24 hours after the single dose of the lipid nanoparticle mRNA formulation made by Process A and Process B, respectively. The graph (i) in FIG. 3 illustrates the citrulline activity due to expressed hOTC after the delivery of the lipid nanoparticle mRNA formulation by Process A and Process B, respectively, right after the mixture of the formulation and without the storing time. Graph (ii) in FIG. 3 illustrates the citrulline activity due to expressed hOTC after the delivery of the lipid nanoparticle mRNA formulation by Process A and Process B, respectively, after the mixture of the formulation was stored for a period of 2.5 months at −80° C.

The results shown in FIG. 3 indicate that the formulation prepared by Process B with pre-formed empty lipid nanoparticles resulted in about 3 times the citrulline activity of hOTC protein when compared to the formulation prepared by Process A. As evidenced by the similarity in the results shown in graphs (i) and (ii), formulations produced by both Process A and by Process B exhibited stability and functionality after extended storage at −80° C.

Example 4. In Vivo Activity of the Expressed hOTC in spf$^{ash}$ mice Under Different Process B Parameters This example illustrates that lipid nanoparticles produced by Process B with different parameters, when delivered to spf$^{ash}$ mice, lead to citrulline activity comparable to that seen in wild type mice.

In this example, OTC spf$^{ash}$ mice were administered a single 0.5 mg/kg dose of hOTC mRNA encapsulated in lipid nanoparticles prepared by Process A or Process B. The liver tissues from these mice were analyzed 24 hours after administration for citrulline production. Four different lipid nanoparticle formulations were produced by Process B, each prepared using a different type of pump.

Figure 4:
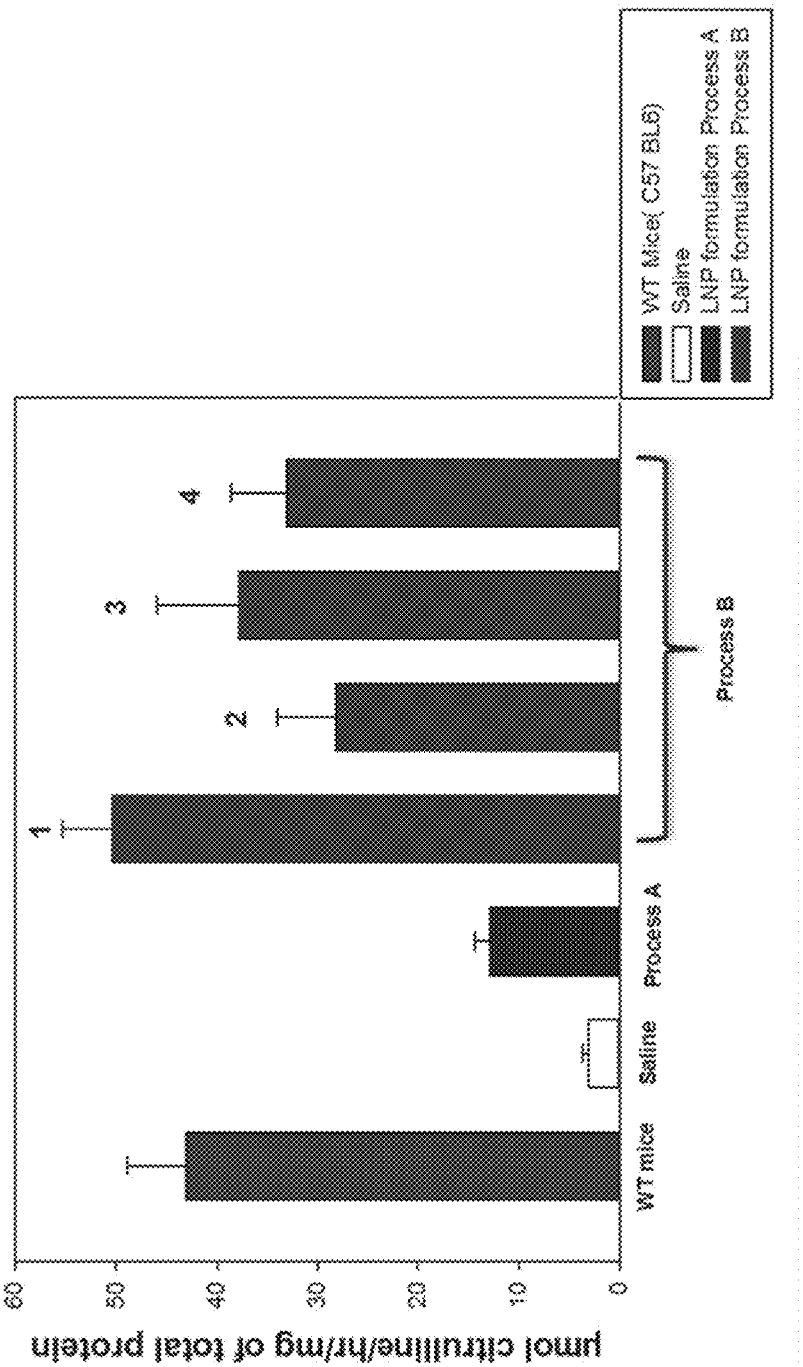
FIG. 4 depicts exemplary activity of expressed hOTC protein (in terms of citrulline production) in livers of female OTC spf$^{ash}$ mice 24 hours after a single 0.5 mg/kg dose of hOTC mRNA encapsulated in lipid nanoparticle formulations made by Process A or by Process B using different pump combinations. Lipid nanoparticle formulations made by Process B were prepared (1) using gear pumps, (2) using peristaltic pumps, (3) using peristaltic pumps at lower flow rates, and (4) using peristaltic pumps at different flow rates of mRNA and empty pre-formed lipid nanoparticles.

FIG. 4 depicts exemplary activity of expressed hOTC protein (in terms of citrulline production) in livers of OTC spf$^{ash}$ mice 24 hours after a single 0.5 mg/kg dose of hOTC mRNA encapsulated in lipid nanoparticle formulations made by Process A or Process B. Lipid nanoparticle formulations made by Process B were prepared (1) using gear pumps, (2) using peristaltic pumps, (3) using peristaltic pumps at lower flow rates, and (4) using peristaltic pumps at different flow rates of mRNA and empty pre-formed lipid nanoparticles.

In some embodiments, the lipid nanoparticle formulations by Process B can be prepared under different process parameters, as shown in Table 2.

TABLE 2

| Process B Formulation | Pump System | Flow Rate of Empty Lipid Nanoparticle Solution (mL/minute) | Flow Rate of mRNA Solution (mL/minute) |
|---|---|---|---|
| 1 | Gear Pump | 50 | 50 |
| 2 | Peristaltic Pump | 50 | 50 |
| 3 | Peristaltic Pump | 10 | 10 |
| 4 | Peristaltic Pump | 50 | 10 |

In some embodiments, different formulations prepared by Process A and Process B formulations numbered 1-4 were tested in vivo.

Generally, the production of citrulline can be used to evaluate the activity of the expressed hOTC protein. As shown in FIG. 4, citrulline activity of hOTC protein in OTC spf$^{ash}$ mice liver was measured 24 hours after the single dose of a lipid nanoparticle mRNA formulation made by either Process A or Process B with different parameters.

As shown in FIG. 4, the exemplary data demonstrate that when different lipid nanoparticle formulations made by Process B (numbered 1-4) were administered to spf$^{ash}$ mice, the treatment led to surprisingly high levels of citrulline activity of hOTC protein that was comparable to that of wild type mice. At the same dosage level (0.5 mg/kg) of OTC mRNA, the lipid nanoparticle formulations prepared by Process B showed 2-4 times as much in vivo activity as the formulation prepared by Process A.

Example 5. In Vitro ASS1 Expression in 293T Cells

This example illustrates that the lipid nanoparticles prepared by Process B resulted in unexpectedly high protein expression in transfected cells.

Figure 5:
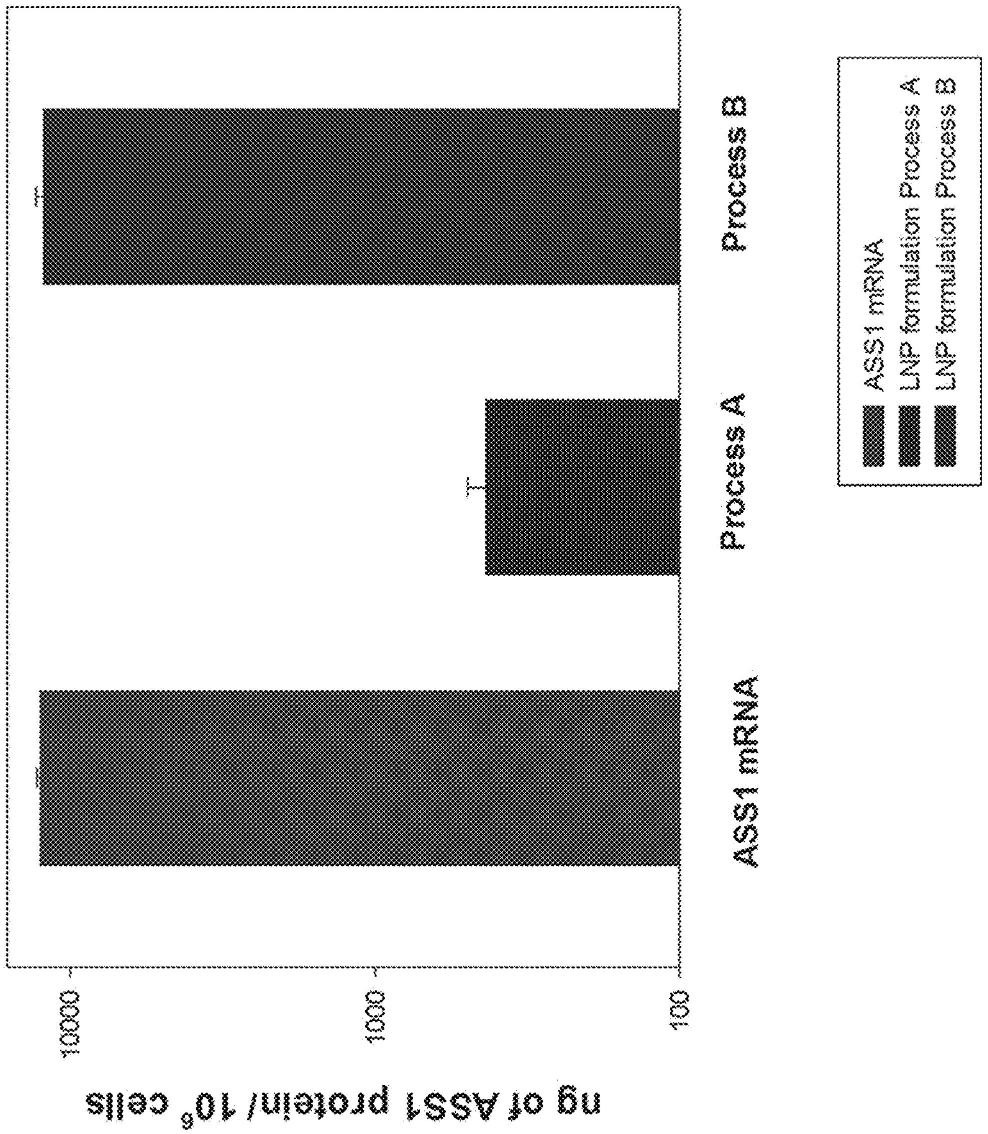
FIG. 5 depicts exemplary human argininosuccinate synthetase (ASS1) protein expression in 293T cells 16 hours post-transfection with either naked hASS1 mRNA (with lipofectamine) or hASS1 mRNA-encapsulated lipid nanoparticles (without lipofectamine) produced by Process A or Process B.

FIG. 5 depicts exemplary human ASS1 protein expression in 293T cells 16 hours post-transfection with either naked hASS1 mRNA (with lipofectamine) or hASS1 mRNA-encapsulated lipid nanoparticles (without lipofectamine) produced by Process A or Process B.

In this example, 293T cells were transfected with ASS1 mRNA lipid nanoparticle formulations prepared by Process A or by Process B. Either 1 μg of ASS1 mRNA was transfected using lipofectamine or 10 μg of ASS1 mRNA encapsulated in lipid nanoparticle formulations were transfected per $10^6$ cells for 24 hours. ASS1 protein expression was determined by ELISA.

As shown in FIG. 5, the lipid nanoparticle formulation prepared by Process B lead to much higher levels of ASS1 protein expression than the formulation prepared by Process A. The levels of ASS1 protein expression resulting from transfection with lipid nanoparticles prepared by Process B was comparable to the levels resulting from transfection with an ASS1 mRNA-lipofectamine complex. The ASS1 protein level per $10^6$ cells for the mRNA-lipofectamine complex, lipid nanoparticle formulation—Process A and lipid nanoparticle formulation—Process B was 12.43, 0.43 and 12.11 μg respectively. The ASS1 protein level resulting from transfection with a lipid nanoparticle formulation prepared by Process B was 28 times that from transfection with a lipid nanoparticle formulation prepared by Process A.

Example 6. In Vivo Expression of hCFTR in Rat Lungs

Figure 6:
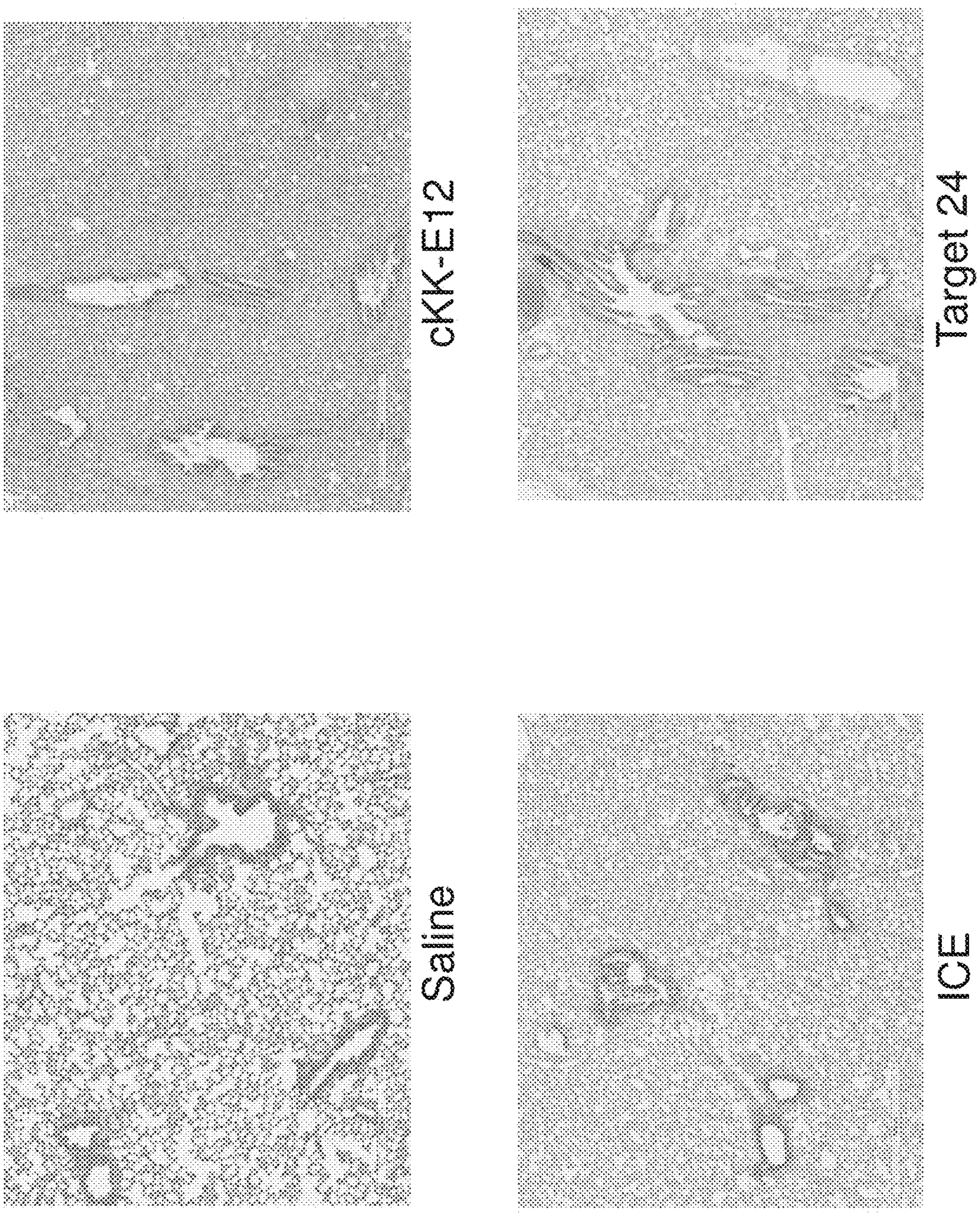
FIG. 6 shows exemplary immunohistochemical detection of human cystic fibrosis transmembrane conductance receptor (hCFTR) protein in rat lungs 24 hours after nebulization of hCFTR mRNA lipid nanoparticles prepared by Process B using different cationic lipids. Protein was detected in both the bronchial epithelial cells as well as the alveolar regions. Positive (brown) staining was observed in all mRNA lipid nanoparticles test article groups, as compared to saline-treated control rat lungs.

FIG. 6 shows exemplary immunohistochemical detection of hCFTR protein in rat lungs 24 hours after nebulization of hCFTR mRNA lipid nanoparticles prepared by Process B using different cationic lipids.

Male Sprague-Dawley rats were administered, via nebulization, lipid nanoparticle formulations containing hCFTR mRNA prepared by Process B. The lipid nanoparticle formulations were made using cKK-E12, ICE or Target 24 lipid as the cationic lipid. The fixed lung tissues from these rats were analyzed for the presence of hCFTR protein by immunohistochemical staining.

Protein was detected in both the bronchial epithelial cells as well as the alveolar regions. Positive (brown) staining was observed in all mRNA lipid nanoparticle test article groups, as compared to the lack of brown staining in the lungs of saline-treated control rats. Rats were dosed via nebulization with (i) saline, (ii) lipid nanoparticle formulation of cKK-E12 lipid prepared by Process B, (iii) lipid nanoparticle formulation of ICE lipid prepared by Process B, or (iv) lipid nanoparticle formulation of Target 24 lipid prepared by Process B.

Example 7. In Vivo Expression of hCFTR in Mice Lungs

Figure 7:
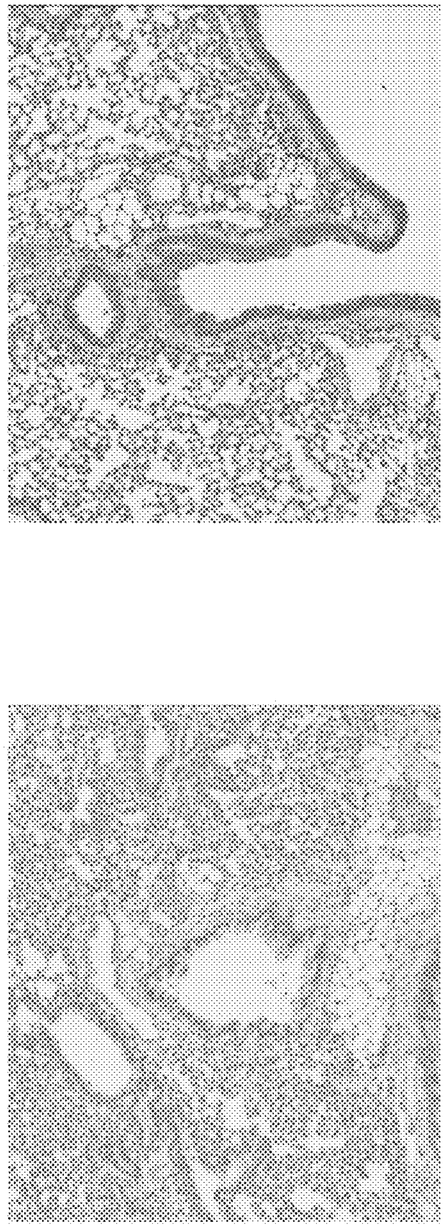
FIG. 7 shows exemplary immunohistochemical detection of hCFTR protein in mouse lungs 24 hours after nebulization of hCFTR mRNA lipid nanoparticles prepared by Process B. Protein was detected in both the bronchial epithelial cells as well as the alveolar regions. Positive (brown) staining was observed for the mRNA lipid nanoparticle test article group, as compared to saline-treated control mice lungs.

FIG. 7 shows exemplary immunohistochemical detection of hCFTR protein in mouse lungs 24 hours after nebulization of hCFTR mRNA lipid nanoparticles prepared by Process B.

In this example, C57BL mice were administered, via nebulization, lipid nanoparticles prepared by Process B that comprised cKK-E12 and contained hCFTR mRNA. The fixed lung tissues from these mice were analyzed for the presence of hCFTR protein by immunohistochemical staining.

Protein was detected in both the bronchial epithelial cells as well as the alveolar regions. Positive (brown) staining was observed for the mRNA lipid nanoparticle test article group, as compared to the lack of brown staining in the lungs of saline-treated control mice.

Example 8. In Vivo Expression of Firefly Luciferase Protein in Mice after Intravitreal Administration This example illustrates exemplary methods of administering firefly luciferase (FFL) mRNA-loaded lipid nanoparticles produced by Process B and methods for analyzing firefly luciferase in target tissues in vivo.

Figure 8:
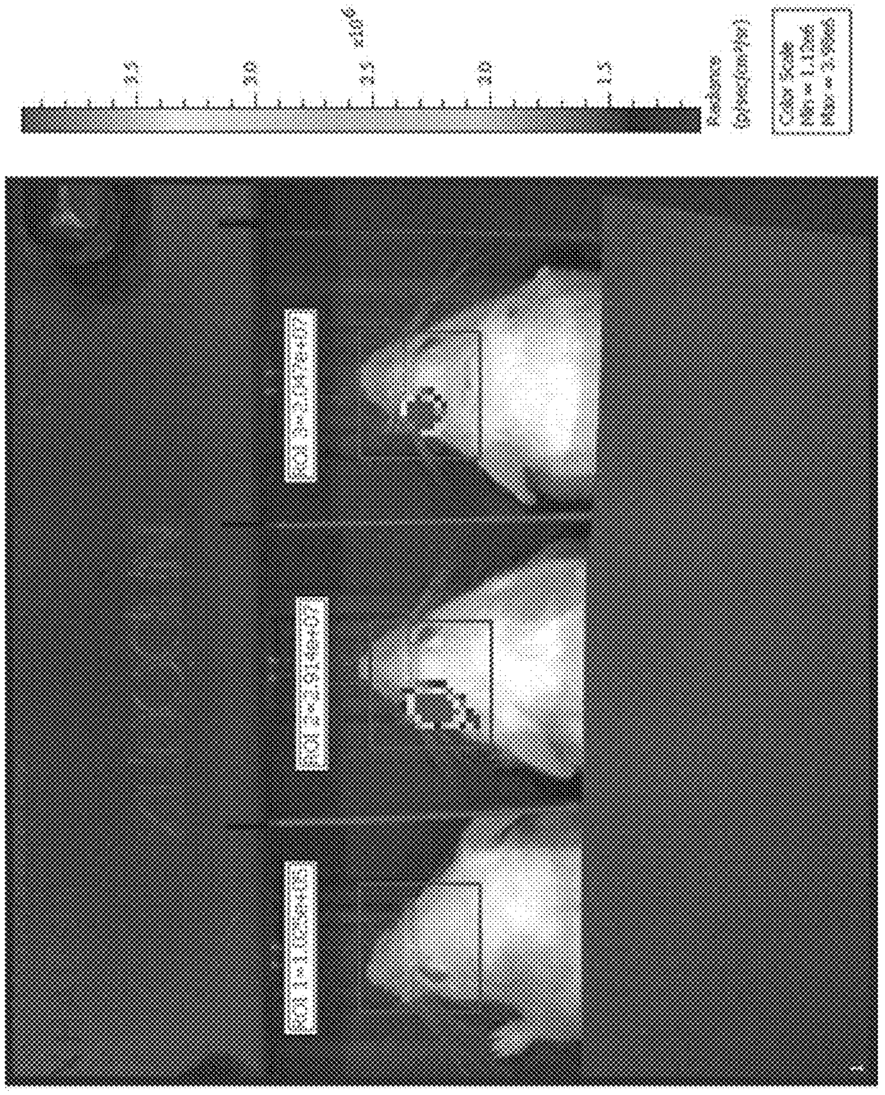
FIG. 8 shows exemplary bioluminescent imaging of wild type mice 24 hours after intravitreal administration of Firefly Luciferase (FFL) mRNA encapsulated in lipid nanoparticles prepared by Process B.

FIG. 8 depicts bioluminescent imaging of wild type mice 24 hours after intravitreal administration of FFL mRNA encapsulated in lipid nanoparticles.

In this example, wild type mice were treated with lipid nanoparticles encapsulating mRNA encoding FFL produced by Process B via intravitreal administration. A solution containing 5 μg of FFL mRNA lipid nanoparticles was injected into the left eye of mice. Luminescence was monitored 24 hours after injection.

The results shown in FIG. 8 indicate that significant luminescence was observed, representing the successful production of active FFL protein in the eyes of these mice. Furthermore, sustained FFL activity was maintained for at least 24 hours.

Example 9. In Vivo Expression of Firefly Luciferase Protein in Mice After Topical Ocular Application This example illustrates exemplary methods of administering firefly luciferase (FFL) mRNA-loaded lipid nanoparticles produced by Process B and methods for analyzing firefly luciferase in target tissues in vivo.

Figure 9:
FIG. 9 shows exemplary bioluminescent imaging of wild type mice 24 hours after topical application of eye drops containing FFL mRNA-encapsulated lipid nanoparticles formulated with polyvinyl alcohol and prepared by Process B.

FIG. 9 depicts bioluminescent imaging of wild type mice 24 hours after topical application of eye drops containing FFL mRNA encapsulated in a lipid nanoparticle formulated with polyvinyl alcohol.

In this example, wild type mice were treated with lipid nanoparticles encapsulating mRNA encoding FFL produced by Process B via topical application (eye drops). A solution containing 5 μg of FFL mRNA lipid nanoparticles formulated with polyvinyl alcohol was applied to the right eye of mice. Luminescence was monitored 24 hours after application.

The results shown in FIG. 9 indicate that significant luminescence was observed, representing the successful production of active FFL protein in the eyes of these mice. Furthermore, sustained FFL activity was maintained for at least 24 hours.

Example 10. In Vivo Activity of PAH Expressed in Mice

In this example, phenylalanine hydroxylase (PAH) knockout (KO) mice were administered a single subcutaneous injection of 20.0 mg/kg hPAH lipid nanoparticles produced by Process B. Phenylalanine levels in the mice serum were measured 24 hours after administration.

Figure 10:
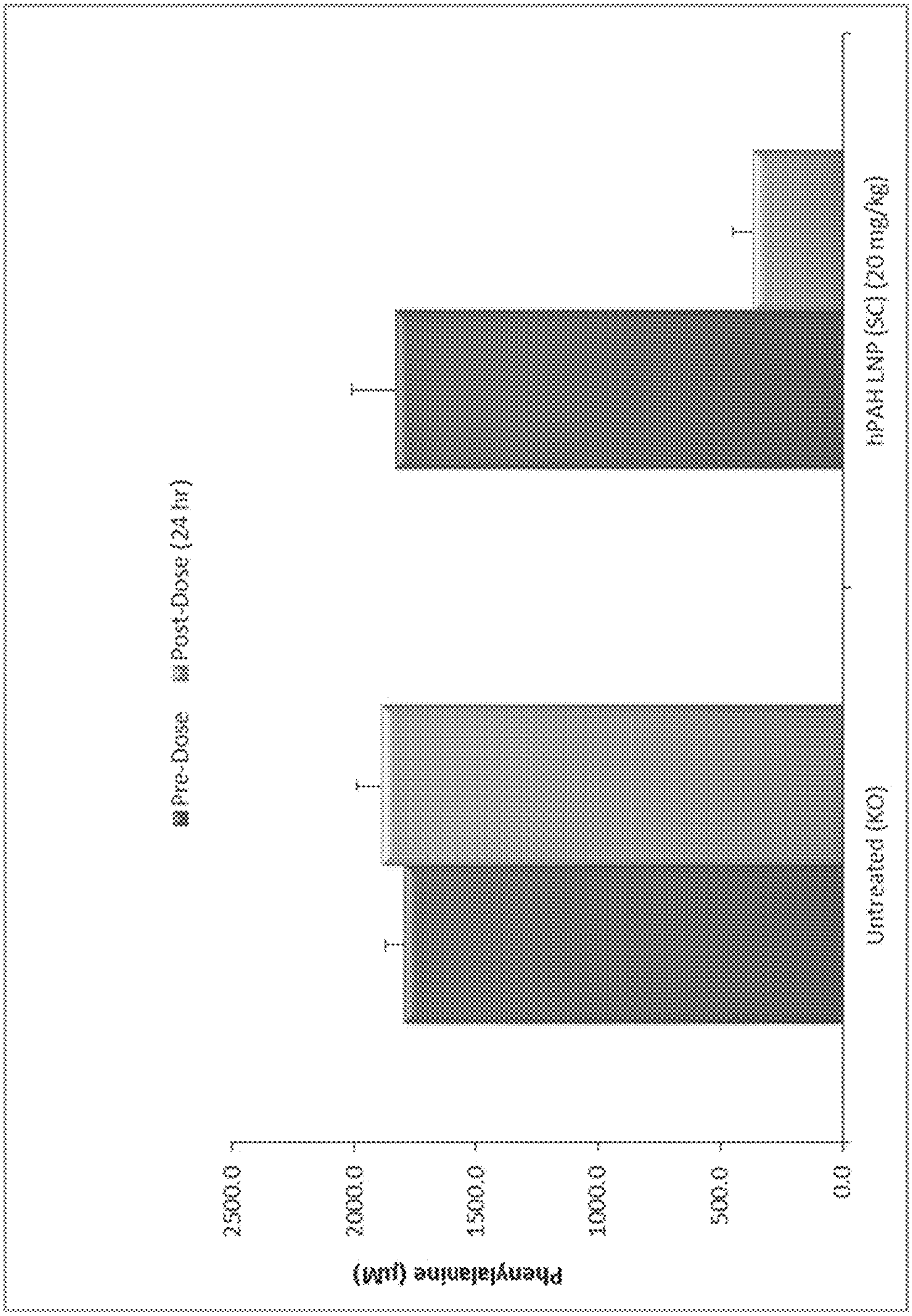
FIG. 10 depicts exemplary serum phenylalanine levels in phenylalanine hydroxylase (PAH) knockout (KO) mice pre- and post-treatment of human PAH (hPAH) mRNA encapsulated in lipid nanoparticles prepared by Process B. Serum samples were measured 24 hours after a single subcutaneous administration.

FIG. 10 shows exemplary serum phenylalanine levels in PAH KO mice pre- and post-treatment with human PAH (hPAH) mRNA encapsulated in lipid nanoparticles produced by Process B. Serum samples were measured 24 hours after a single subcutaneous administration.

The mRNA-derived hPAH protein was shown to be enzymatically active, as demonstrated by measuring levels of serum phenylalanine reduction using a custom ex vivo activity assay. Generally, the reduction of serum phenylalanine can be used to evaluate the activity of the potency (i.e., expressed PAH protein) and the efficacy of the delivery method. As shown in FIG. 10, exemplary serum phenylalanine levels in PAH KO mice were measured before and 24 hours after the single dose of the lipid nanoparticle encapsulating hPAH mRNA formulation prepared by Process B that was delivered subcutaneously. As a comparison, serum phenylalanine levels in saline treated PAH KO mice were also measured.

The results shown in FIG. 10 indicate that the subcutaneously injected lipid nanoparticle hPAH mRNA formulation resulted in significant phenylalanine level reduction. There was not a significant difference in phenylalanine levels in saline-treated PAH KO mice before and after the dose.

Example 11. In Vivo Activity of OTC Expressed in Mice

This example shows a comparison of levels of OTC protein activity in the livers of saline treated OTC KO $spf^{ash}$ mice and OTC KO $spf^{ash}$ mice treated with subcutaneous administration of hOTC mRNA-loaded lipid nanoparticles made by Process B.

Figure 11:
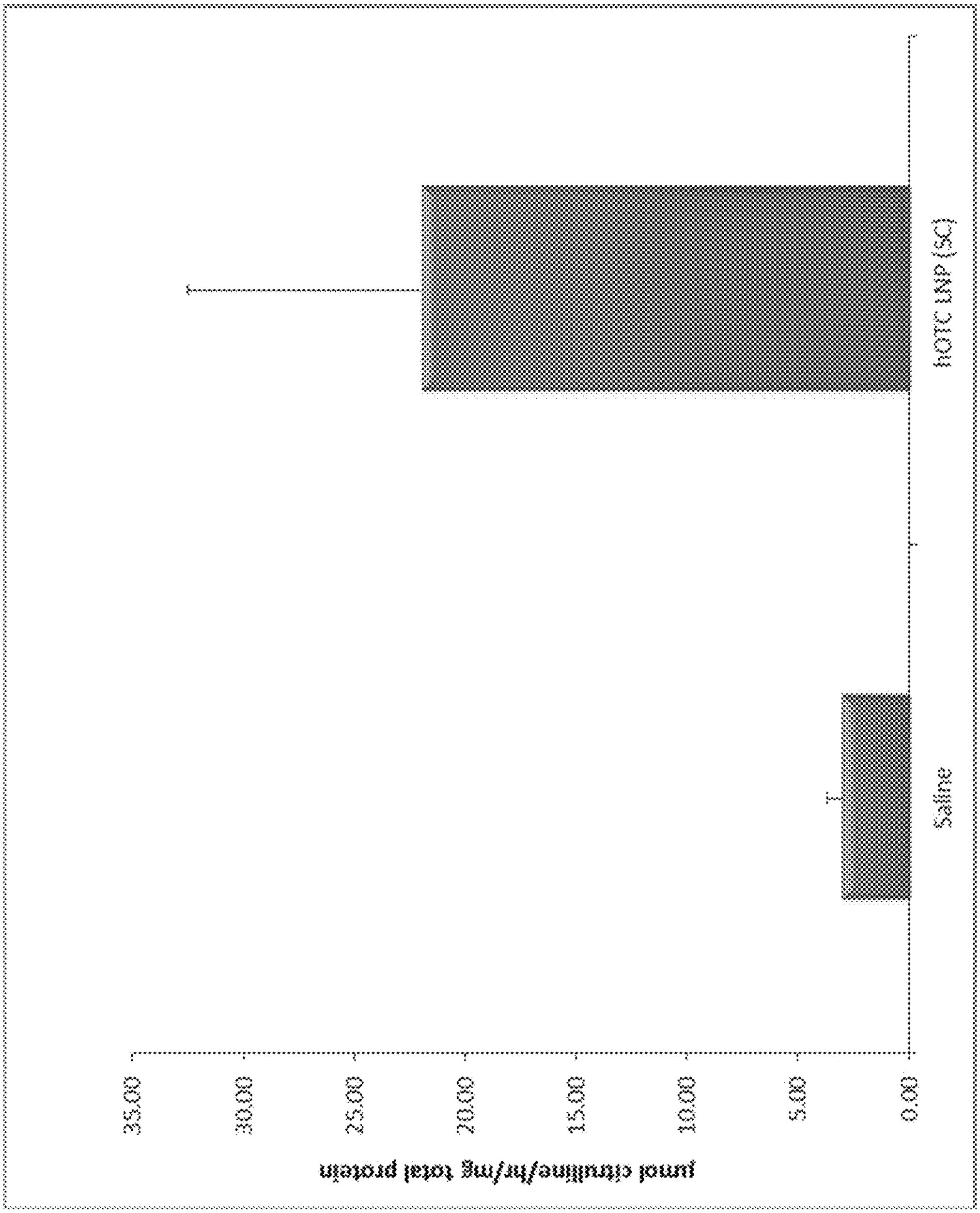
FIG. 11 depicts exemplary activity of expressed hOTC protein (in terms of citrulline production) in the livers of OTC KO spf$^{ash}$ mice 24 hours after a single subcutaneous administration of hOTC mRNA-encapsulated lipid nanoparticles prepared by Process B.

As shown in FIG. 11, exemplary citrulline production as a result of expressed hOTC protein in the livers of OTC KO $spf^{ash}$ mice was measured 24 hours after the single subcutaneous dose of the lipid nanoparticle encapsulating hOTC mRNA formulation made by Process B. In addition, as a comparison, citrulline production in livers of OTC KO $spf^{ash}$ mice was measured after saline was injected.

The results shown in FIG. 11 indicate that the subcutaneously injected lipid nanoparticle hOTC mRNA formulation made by Process B resulted in significant activity of the expressed hOTC protein 24 hours post-dose compared with saline treated diseased mice.

Example 12. In Vivo Expression of ASS1 in Mice

Figure 12:
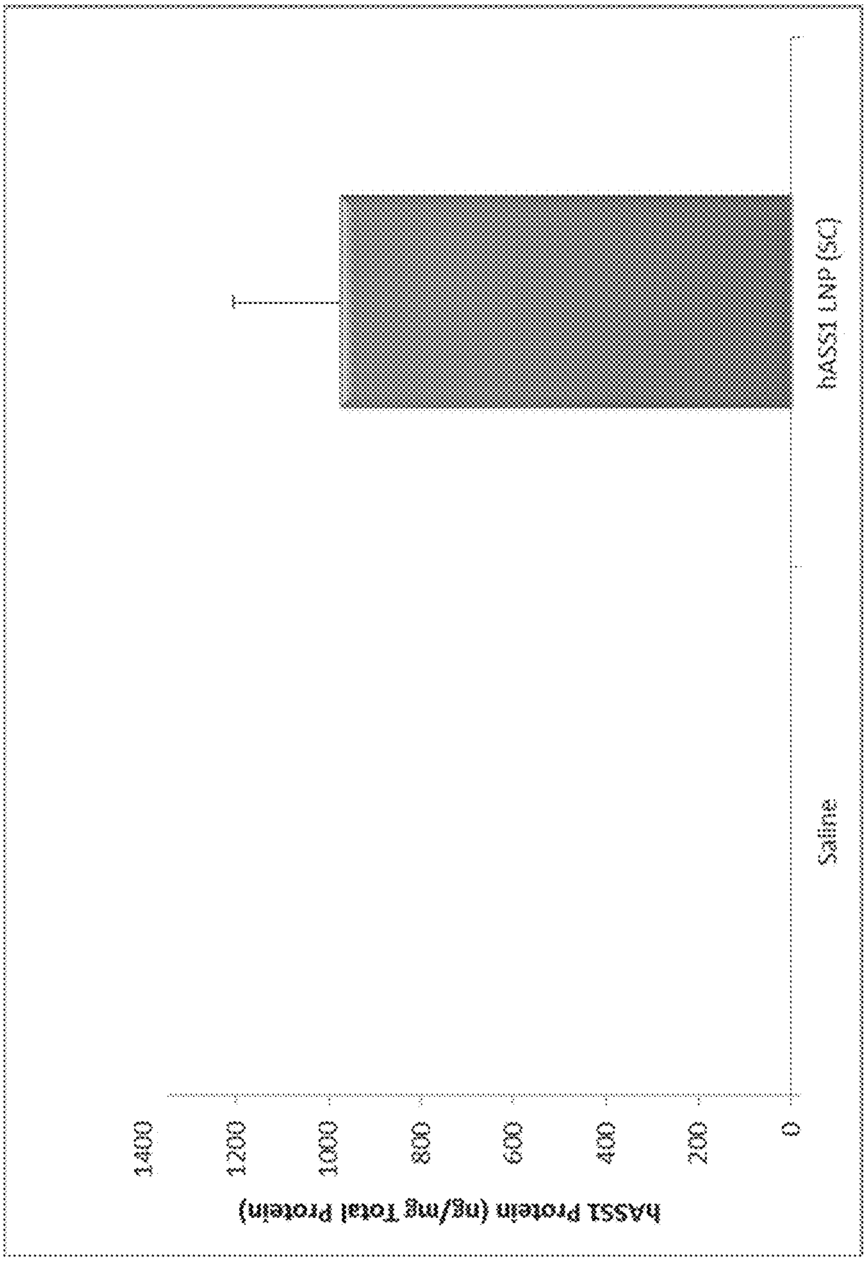
FIG. 12 depicts exemplary human ASS1 protein levels measured in the livers of ASS1 KO mice 24 hours after a single subcutaneous administration of hASS1 mRNA-encapsulated lipid nanoparticles prepared by Process B.

FIG. 12 depicts exemplary human ASS1 protein levels measured in ASS1 KO mice liver 24 hours after a single subcutaneous administration of lipid nanoparticle formulation encapsulating hASS1 mRNA made by Process B.

Generally, the expressed hASS1 protein levels can be used to evaluate the efficiency of the delivery method. As shown in FIG. 12, exemplary hASS1 protein level in ASS1 KO mice was measured 24 hours after the single subcutaneous dose of the lipid nanoparticle encapsulating hASS1 mRNA formulation made by Process B. In addition, as a comparison, hASS1 protein level in ASS1 KO mice treated with saline was also measured.

The results shown in FIG. 12 indicate that subcutaneously injected hASS1 mRNA lipid nanoparticle formulation made by Process B resulted in significant hASS1 protein level in hASS1 KO mice 24 hours post-dose when compared with saline-treated hASS1 KO mice.

Example 13. In Vivo Expression of hEPO in Mice Via Various Routes of Administration This example shows a comparison of expressed human EPO (hEPO) in wild type mice after administration of hEPO mRNA encapsulated in lipid nanoparticles made by Process B by various routes. This example further illustrates a comparison of potency of mRNA delivered via lipid nanoparticles produced by Process A and Process B for intradermal and intramuscular administration at various dose levels. It is shown that mRNA delivered via lipid nanoparticles produced by process B were substantially more potent than those produced by Process A at all dosages and time points, whether delivered by intradermal or intramuscular routes of administration assessed.

In this example, wild type mice were administered via intradermal, subcutaneous, or intramuscular routes a single dose at varying concentrations (i.e., 1 μg, 10 μg, or 50 μg) of hEPO mRNA encapsulated lipid nanoparticles produced by Process B. Serum levels of hEPO protein were measured 6 hours and 24 hours after administration. Additionally, wild type mice were administered via intradermal or intramuscular routes a single dose at varying concentrations (i.e., 1 μg, 10 μg, or 50 μg) of hEPO mRNA encapsulated lipid nanoparticles produced by Process A or Process B. Serum levels of hEPO protein were measured 6 hours and 24 hours after administration.

Figure 13:
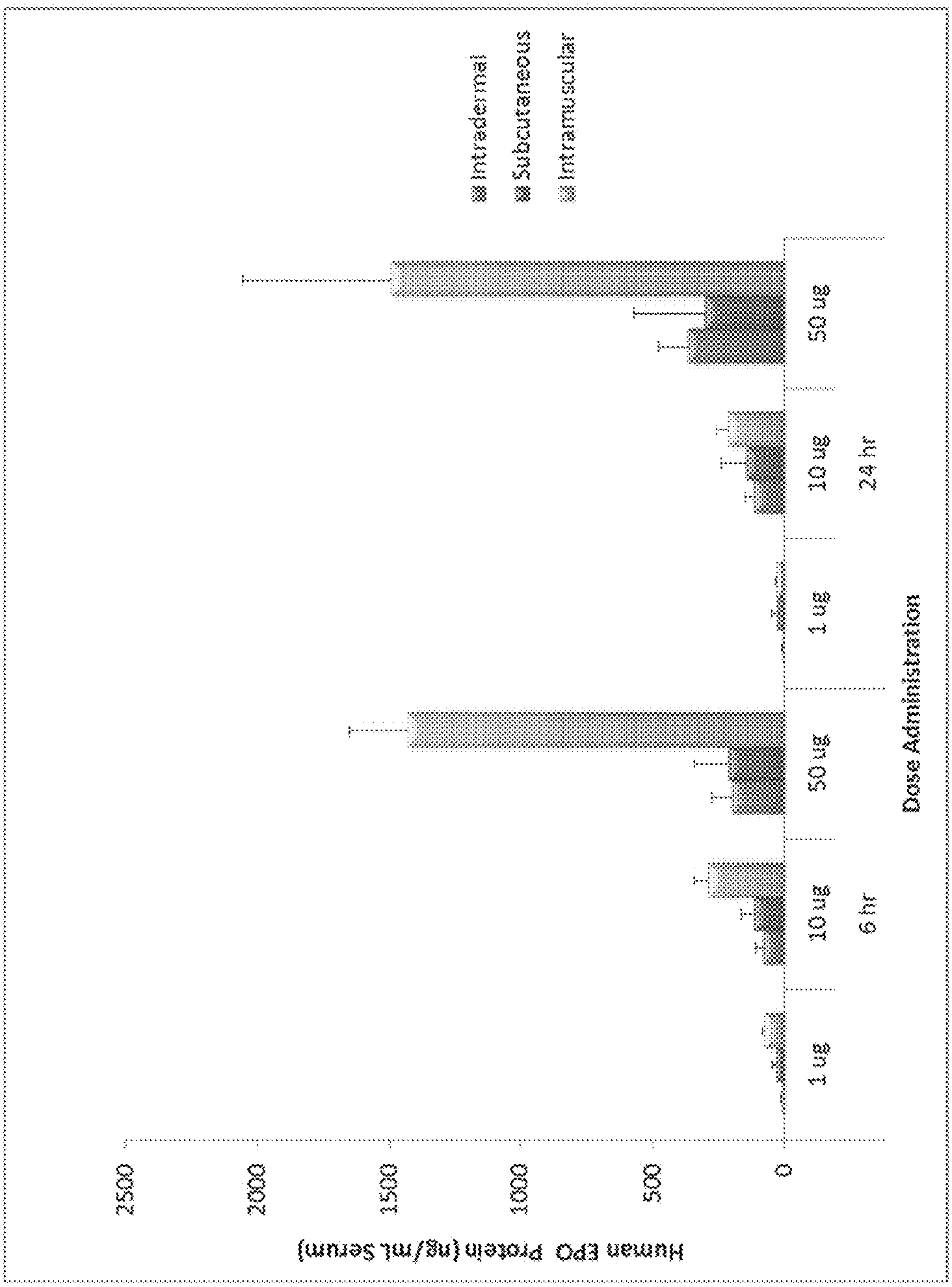
FIG. 13 depicts exemplary human erythropoietin (hEPO) protein levels measured in serum of treated mice at 6 hours and 24 hours after a single administration of different doses of hEPO mRNA-encapsulated lipid nanoparticles prepared by Process B. The routes of administration used were intradermal, subcutaneous and intramuscular delivery.

FIG. 13 depicts exemplary hEPO protein levels measured in the serum of treated mice 6 hours and 24 hours after a single administration of hEPO mRNA formulation made by Process B. The routes compared were administration by intradermal, subcutaneous or intramuscular injection.

The levels of hEPO protein in the serum of mice after treatment can be used to evaluate the potency of mRNA via the different delivery methods. As shown in FIG. 13, exemplary hEPO protein levels protein in mice sera were evaluated by ELISA 6 hours and 24 hours after the single dose of the hEPO mRNA lipid nanoparticle formulation made by Process B at 1 μg, 10 μg and 50 μg. In addition, hEPO protein levels from intradermal, subcutaneous and intramuscular routes of administration were compared.

The results shown in FIG. 13 indicate that the hEPO mRNA lipid nanoparticle formulation intramuscularly injected generally resulted in highest levels of hEPO protein when compared to the intradermal and subcutaneous routes. At 6 hours post-dose, hEPO protein levels were slightly higher from subcutaneous administration than from intradermal administration.

Figure 14:
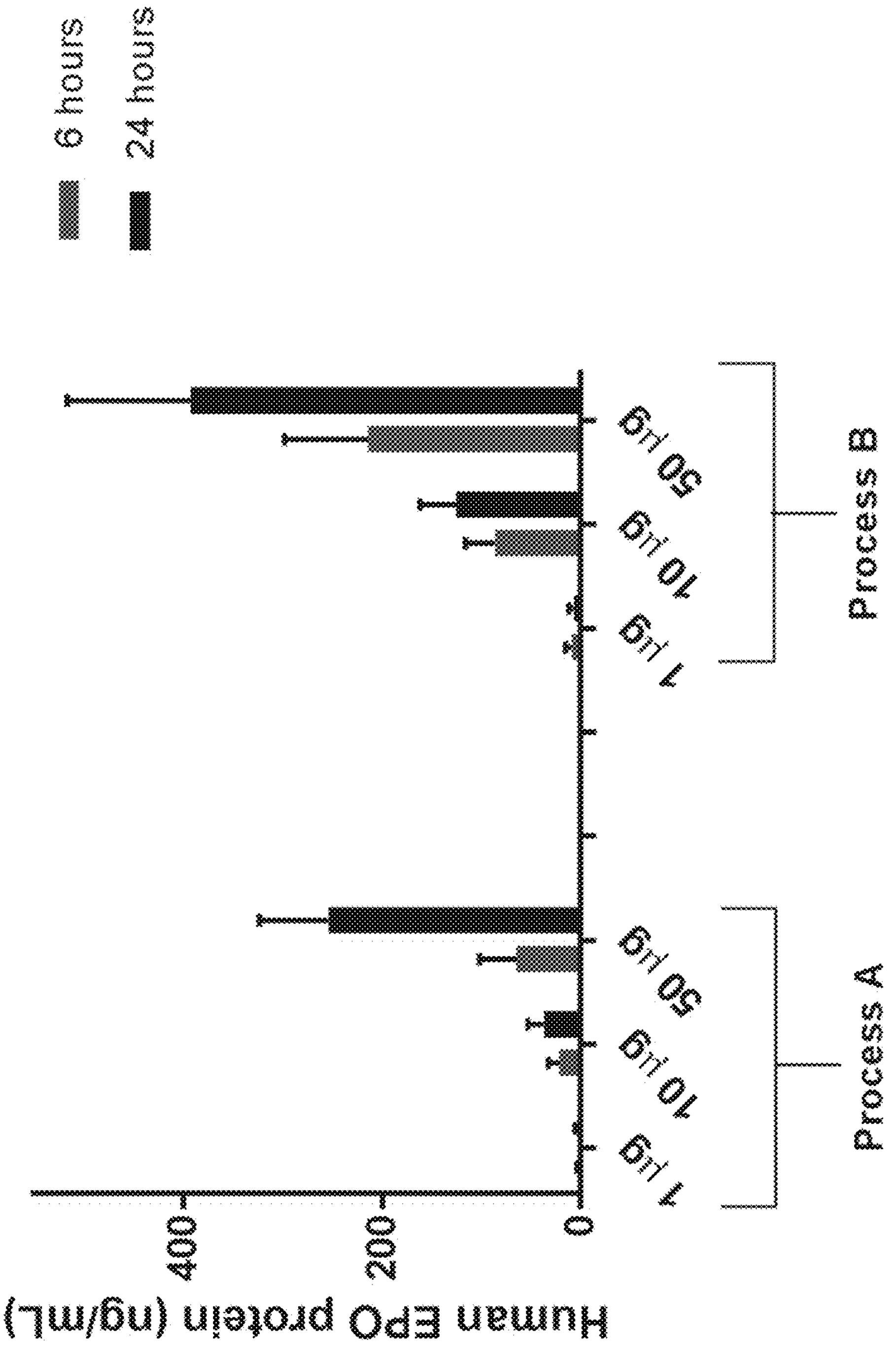
FIG. 14 shows a comparison of hEPO protein levels measured in the serum of treated mice 6 hours and 24 hours after a single intradermal dose of hEPO mRNA encapsulated in a lipid nanoparticle formulation made by Process A or by Process B.

Comparison of mRNA Lipid Nanoparticles Produced by Process A and Process B for Intradermal and Intramuscular Administration at Various Dose Levels FIG. 14 depicts a comparison of hEPO protein levels measured in the serum of treated mice 6 hours and 24 hours after a single intradermal dose of hEPO mRNA encapsulated in lipid nanoparticle formulation made by Process A or Process B. FIG. 14 indicates that, at all doses, the formulation prepared by Process B resulted in about 2-4 times higher hEPO protein level expression as compared to the formulation prepared by Process A.

Figure 15:
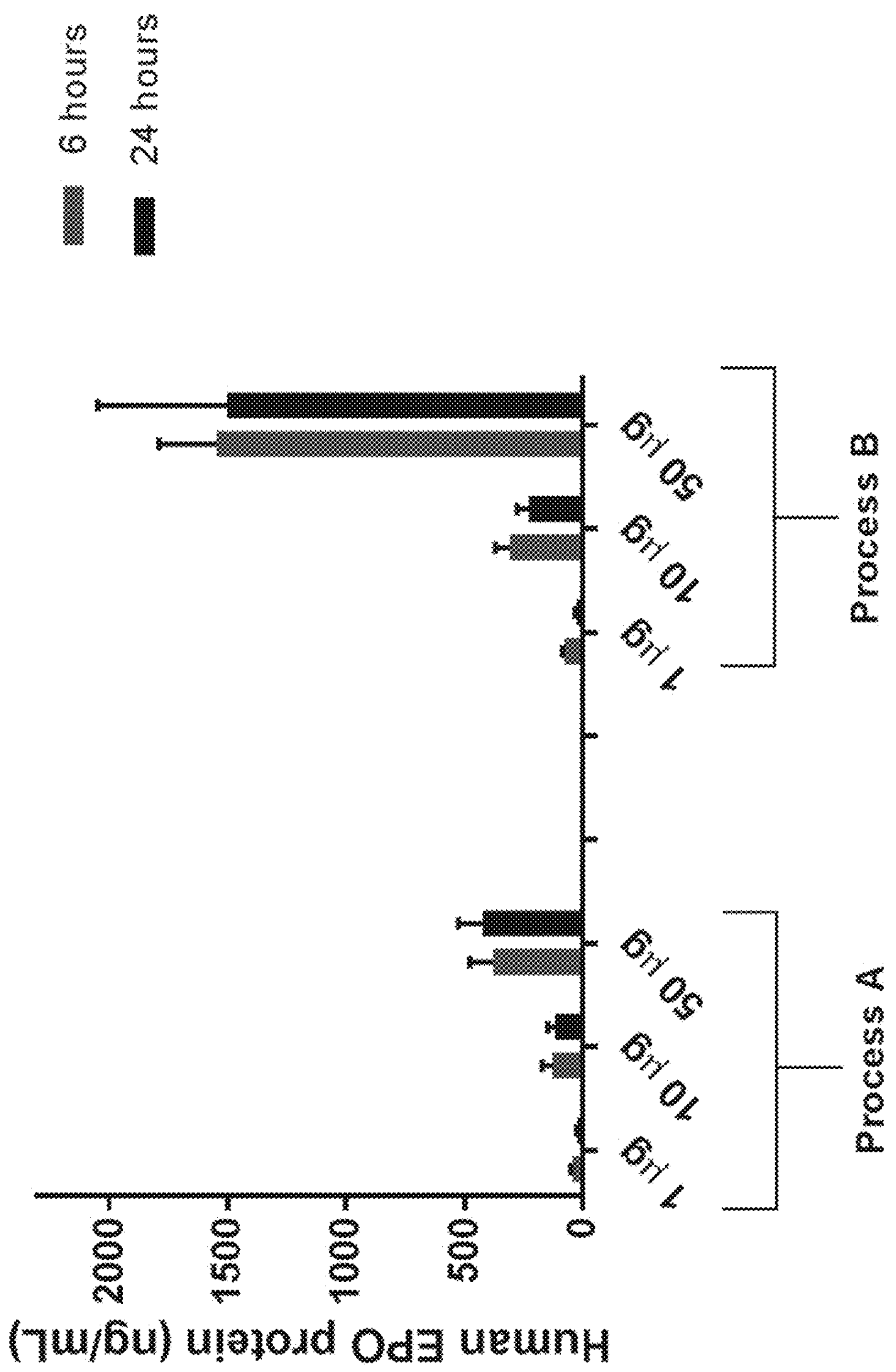
FIG. 15 depicts a comparison of hEPO protein levels measured in the serum of treated mice 6 hours and 24 hours after a single intramuscular dose of hEPO mRNA encapsulated in lipid nanoparticle formulation made by Process A or by Process B.

FIG. 15 depicts a comparison of hEPO protein levels measured in the serum of treated mice 6 hours and 24 hours after a single intramuscular dose of hEPO mRNA encapsulated in lipid nanoparticle formulation made by Process A or Process B. FIG. 15 indicates that, at all doses, the formulation prepared by Process B resulted in about 2-4 times higher hEPO protein level expression as compared to the formulation prepared by Process A.

As shown in FIG. 14 and FIG. 15, hEPO protein levels protein in mice sera were evaluated by ELISA 6 hours and 24 hours after the single dose of the hEPO mRNA lipid nanoparticle formulation made by Process A or Process B at 1 μg, 10 μg and 50 μg via intradermal and intramuscular administration, respectively. The results show substantially higher potency of the mRNA encapsulated lipid nanoparticles produced by Process B. It also was observed that higher potency of the Process B formulation was associated with various cells of the integumentary system (i.e., myocytes, fibroblasts, macrophages, adipocytes, etc.).

Example 14. Protein Expression from mRNA Lipid Nanoparticles in an Animal Model This example illustrates significantly improved in vivo protein expression with mRNA delivered via lipid nanoparticles produced by Process B as compared to Process A, across a range of dose levels.

In this study, male spf$^{ash}$ mice were treated with hOTC mRNA lipid nanoparticles produced by Process A or by Process B, in each case at four different dose levels (0.50 mg/kg, 0.16 mg/kg, 0.05 mg/kg, and 0.016 mg/kg). The test articles used throughout the study were the same except for the noted differences in the lipid nanoparticle production process (Process A versus Process B) and dose.

The test articles were administered as a single dose via tail vein injection. At 24 hours post administration mice were presented with an ammonia challenge wherein a bolus injection of ammonium chloride (5 mmol/kg $NH_4Cl$) was administered intraperitoneally. Blood was collected 40 minutes after the $NH_4Cl$ challenge by collecting aliquots of whole blood into lithium heparin plasma tubes, which were processed to plasma and plasma ammonia was analyzed using an IDEXX Catalyst Dx analyzer. Then the animals were sacrificed, and their livers were harvested and assessed for hOTC expression using sandwich ELISA.

Figure 16:
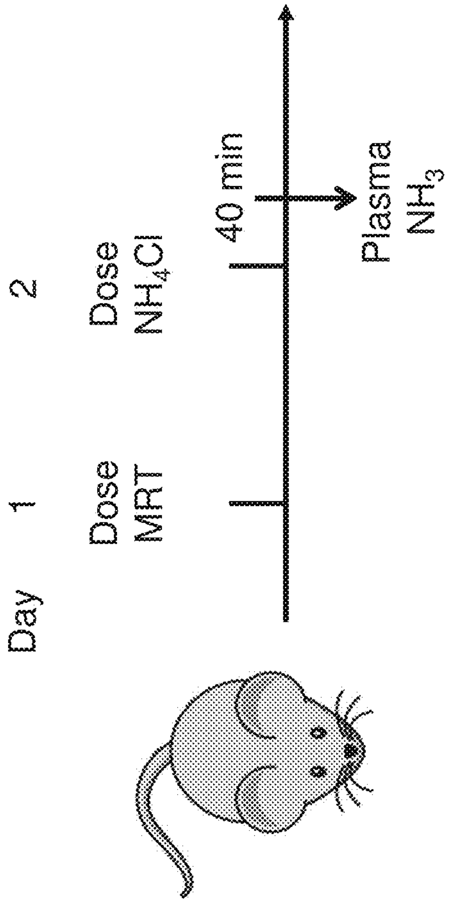
FIG. 16 depicts an exemplary dosing and testing scheme in Spf$^{ash}$ mice that involved an ammonia challenge.

FIG. 16 depicts a schematic of the ammonia challenge portion of the study, which was performed to represent a hyperammonemic episode that a patient suffering from OTC deficiency could experience.

Figure 17:
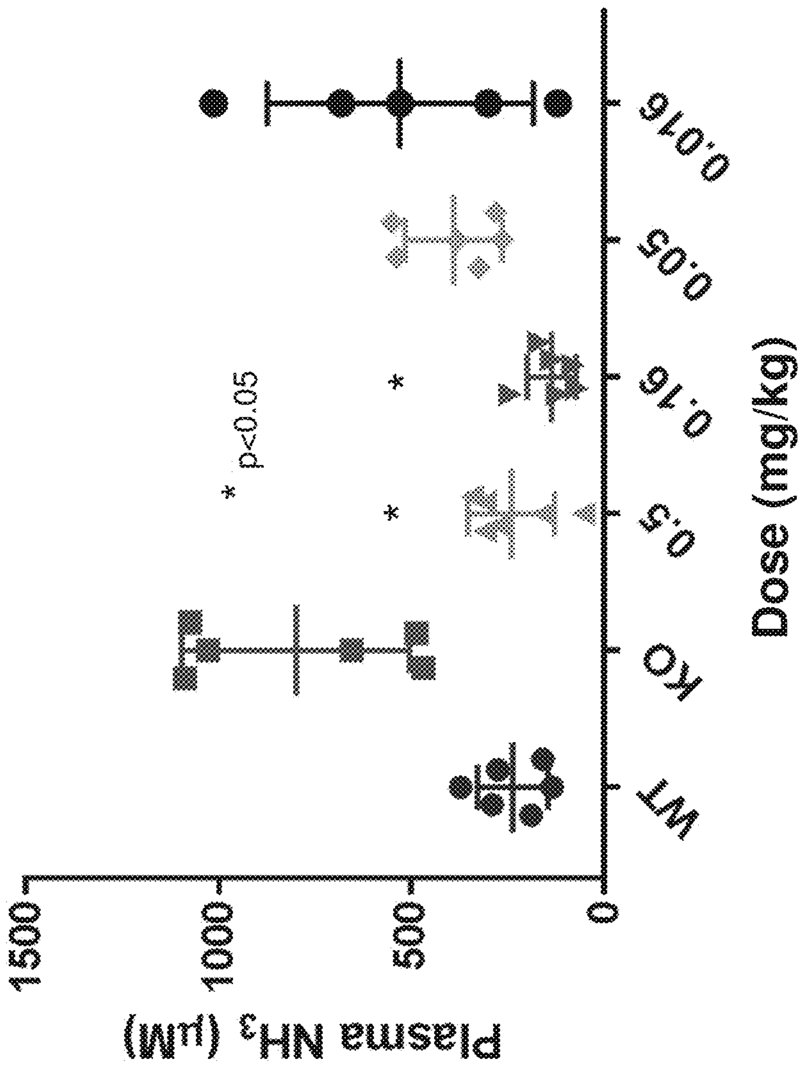
FIG. 17 depicts exemplary plasma ammonia levels in Spf$^{ash}$ mice after treatment with different dose levels of hOTC mRNA-loaded lipid nanoparticles, each prepared via Process B, following an ammonia challenge with $NH_4Cl$.

FIG. 17 shows the plasma ammonia levels of each of the ammonia-challenged mice, particularly the wild-type mice having normal murine OTC (WT), spf$^{ash}$ mice that received no hOTC mRNA lipid nanoparticles (KO), and spf$^{ash}$ mice that received a single dose of 0.5, 0.16, 0.05 or 0.016 mg/kg mRNA lipid nanoparticles produced by Process B. As shown by the figure, a statistically significant protection of the model hyperammonemic episode was achieved at the 0.5 mg/kg and at the 0.16 mg/kg doses of the hOTC mRNA lipid nanoparticles produced by Process B, as compared to the marked elevations in plasma ammonia under identical conditions for the spf$^{ash}$ mice that received no hOTC mRNA lipid nanoparticles (KO). This data illustrates that mRNA lipid nanoparticles produced by Process B and administered at doses of 0.5 mg/kg and at 0.16 mg/kg was effective for at least 24 hours following administration in protecting against an ammonium chloride challenge.

Figure 18:
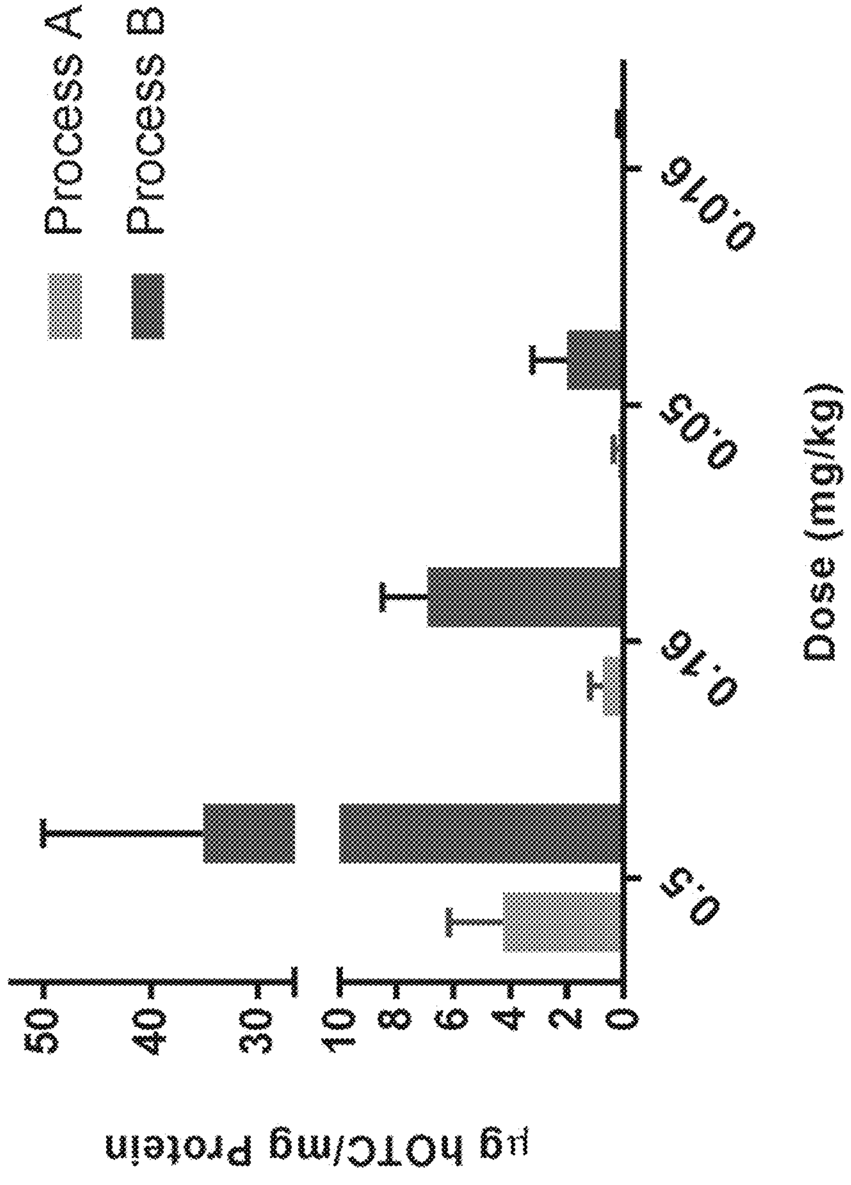
FIG. 18 shows hOTC protein expression in Spf$^{ash}$ mouse livers 24 hours after a single intravenous dose (i.e., 0.5 mg/kg, 0.16 mg/kg, 0.05 mg/kg, or 0.016 mg/kg) of hOTC mRNA encapsulated in lipid nanoparticle formulations made by Process A or by Process B.

FIG. 18 and Table 3 show the hOTC protein levels from the livers of the animals sacrificed at 24 hours post administration of the hOTC mRNA lipid nanoparticles, as measured by sandwich ELISA. As these results show, the hOTC protein expressed from livers of mice treated with the mRNA lipid nanoparticles prepared by Process B was nearly 1000% (i.e., ten times) higher than that from livers of mice treated with the same mRNA lipid nanoparticles prepared by Process A. Table 3 provides the particular amounts of hOTC protein (as a percent of total protein) expressed from livers of mice treated with the mRNA lipid nanoparticles prepared by Process A and by Process B for all doses 24 hours following administration.

TABLE 3

In vivo hOTC protein expression measured 24 hours following administration of different doses (as shown) of hOTC mRNA lipid nanoparticles formulated by Process A or Process B.

| Dose (mg/kg) | μg hOTC/mg protein Process A | μg hOTC/mg protein Process B | Avg. increase in hOTC expression from Process A to Process B |
|---|---|---|---|
| 0.5 | 4.26 ± 1.90 | 35.12 ± 14.94 | 724% (8.2x) |
| 0.16 | 0.73 ± 0.46 | 6.90 ± 1.61 | 845% (9.35x) |
| 0.05 | 0.18 ± 0.19 | 2.01 ± 1.19 | 1016% (11.04x) |
| 0.016 | 0.012 ± 0.006 | 0.126 ± 0.077 | 950% (10.01x) |
| Average across all doses | | | 884% (9.65x) |

As shown by Table 3, the amount of hOTC protein expressed (as a percent of total protein) from livers of mice treated with the mRNA lipid nanoparticles prepared by Process B exceeded by more than about 700% (about 8×) and by up to about 1000% (about 11×) the amount of hOTC protein expressed (as a percent of total protein) from livers of mice treated with the mRNA lipid nanoparticles prepared by Process A, across all dosages at 24 hours following administration. The overall average increase in the amount of hOTC protein expressed (as a percent of total protein) from livers of mice treated with the mRNA lipid nanoparticles prepared by Process B versus by Process A was 884% (9.65×), across all dosages at 24 hours following administration. This data illustrates that mRNA lipid nanoparticles produced by Process B were significantly more potent than the same mRNA lipid nanoparticles produced by Process A, at all doses, at 24 hours following administration.

Figure 19:
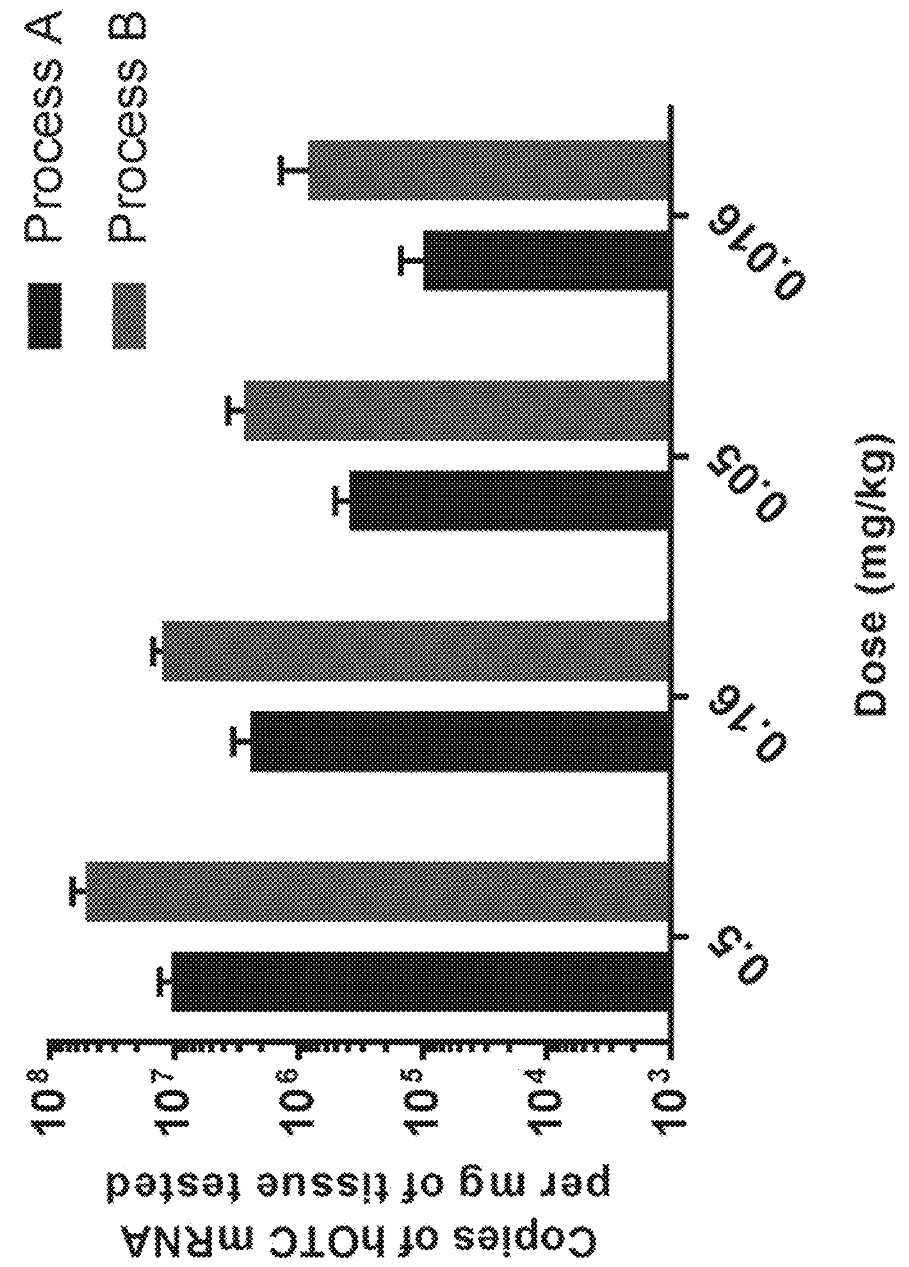
FIG. 19 shows a comparison of hOTC mRNA copy number in liver tissue of OTC spf$^{ash}$ mice 24 hours after a single intravenous a dose (i.e., 0.5 mg/kg, 0.16 mg/kg, 0.05 mg/kg, or 0.016 mg/kg) of hOTC mRNA encapsulated in lipid nanoparticle formulation made by Process A or by Process B.
Figure 20:
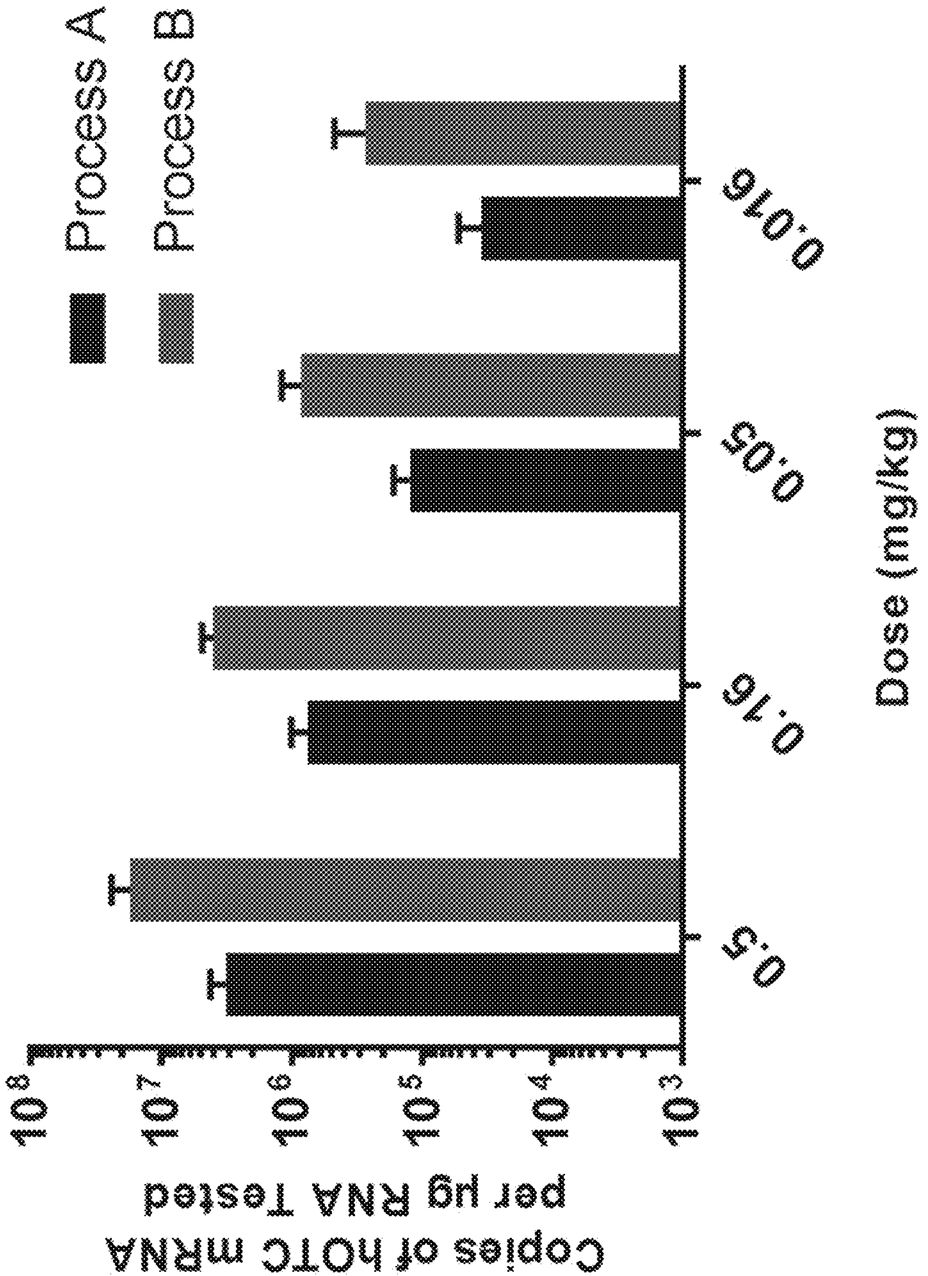
FIG. 20 shows a comparison of hOTC mRNA copy number in RNA tested of OTC spf$^{ash}$ mice 24 hours after a single intravenous dose (i.e., 0.5 mg/kg, 0.16 mg/kg, 0.05 mg/kg, and 0.016 mg/kg) of hOTC mRNA encapsulated in lipid nanoparticle formulations made by Process A or by Process B.

FIG. 19 shows a comparison of hOTC protein amount in liver tissue of OTC spf$^{ash}$ mice 24 hours after a single intravenous injection of hOTC mRNA at various doses (i.e., 0.5 mg/kg, 0.16 mg/kg, 0.05 mg/kg, and 0.016 mg/kg) encapsulated in lipid nanoparticle formulations made by Process A or Process B. As can be seen in the figure, the formulation doses produced by Process B resulted in more copies of hOTC mRNA per mg tissue than did the formulation produced by Process A. FIG. 20 shows a comparison of hOTC protein amount in RNA tested of OTC spf$^{ash}$ mice 24 hours after a single intravenous injection of hOTC mRNA at various doses (i.e., 0.5 mg/kg, 0.16 mg/kg, 0.05 mg/kg, and 0.016 mg/kg) encapsulated in lipid nanoparticle formulations made by Process A or Process B. As can be seen in the figure, the formulation doses produced by Process B resulted in more copies of hOTC mRNA per μg RNA tested than did the formulation produced by Process A.

Example 15. Duration of Activity by Protein Expressed from mRNA Lipid Nanoparticles in an Animal Model In this example, the activity of an exemplary protein expressed in vivo from an mRNA lipid nanoparticle persisted for an extended duration of at least 15 days.

In this study, male spf$^{ash}$ mice were administered via single intravenous tail vein injection a dose of 1.0 mg/kg hOTC mRNA lipid nanoparticles produced by Process B. At each timepoint of 24 hours (Day 2), 48 hours (Day 3), 72 hours (Day 4), 96 hours (Day 5), 8 days (Day 8), 11 days (Day 11), and 15 days (Day 15) following administration a cohort of the mice were removed.

For each removed cohort, animals were subjected to an ammonia challenge after which blood was collected for plasma ammonia (μmol/L) measurements. Then the animals were sacrificed and citrulline citrulline/hr/mg of total protein) and urinary orotic acid (μ mol/mmol creatinine) were measured.

For the ammonia challenge and plasma ammonia measurements, see FIG. 16 for a general schematic and Example 14 for a description of this test.

For the citrulline measurements, mouse liver homogenate was prepared and diluted in 1×DPBS then added into UltraPure water. Citrulline standard was added in predetermined amounts to serve as an internal reference. A reaction mix containing carbamoyl phosphate, ornithine and triethanolamine was added and the reaction was allowed to proceed at 37° C. for 30 minutes. The reaction was stopped with a mix of phosphoric and sulfuric acid, and diacetylmonoxime was added. The sample was incubated at 85 degrees Celsius for 30 minutes, cooled briefly, and read at 490 nm to quantify the citrulline against the citrulline standard.

For the urinary orotic acid measurements, orotic acid quantification from animal urine samples was performed via Ultra Performance Liquid Chromatography (UPLC) using an ion exchange column. Briefly, urine samples were diluted two-fold using RNase-free water and a portion was loaded onto a ThermoScientific 100× column. The mobile phase comprising acetonitrile and 25 mM ammonium acetate afforded separation and quantification of orotic acid with detection based on absorbance at 280 nm.

Figure 21:
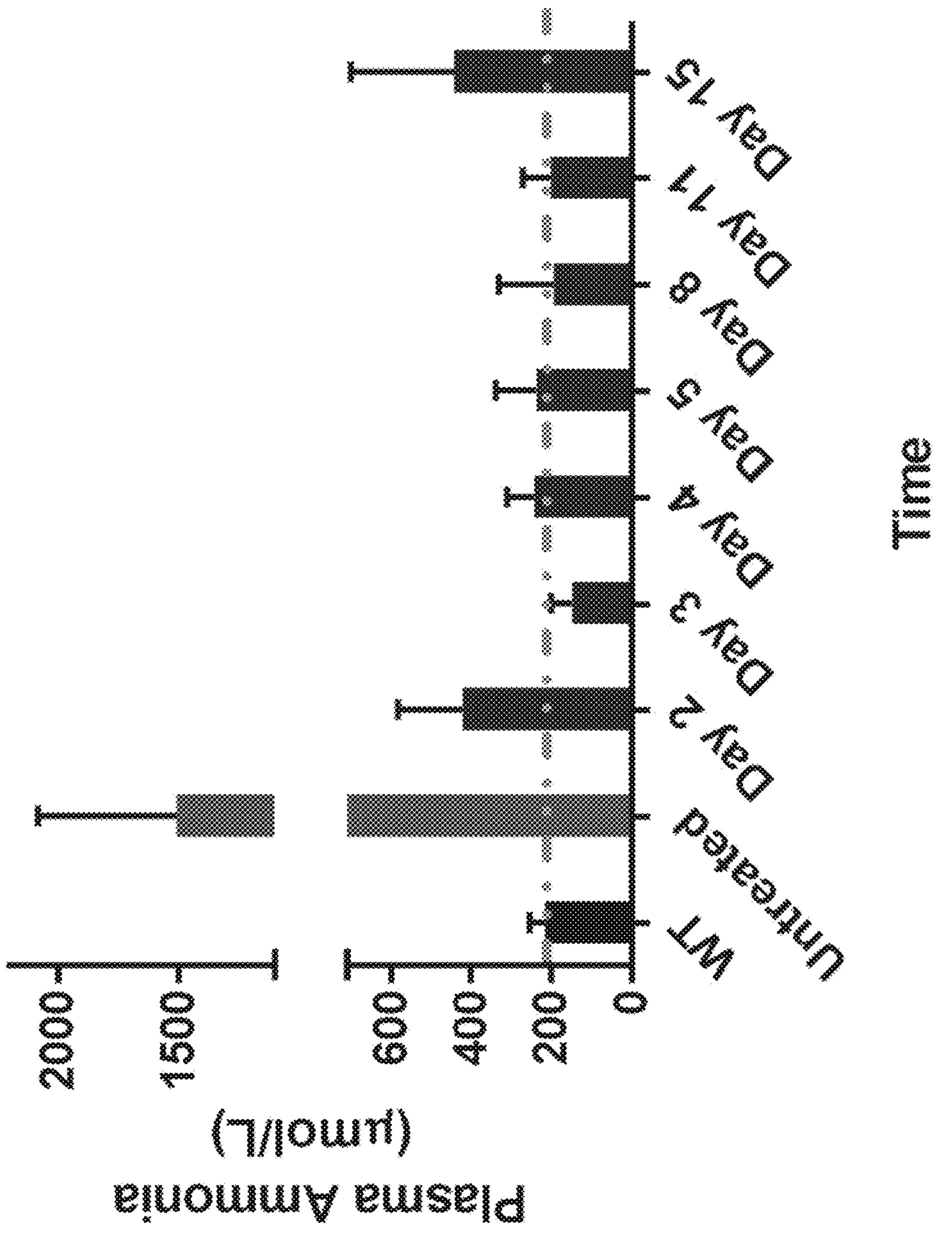
FIG. 21 shows plasma ammonia results 40 minutes after being subjected to an ammonia challenge in each of wild-type mice (WT), untreated spf$^{ash}$ mice (Untreated), and spf$^{ash}$ mice at 24 hours (Day 2), 48 hours (Day 3), 72 hours (Day 4), 96 hours (Day 5), 8 days (Day 8), 11 days (Day 11), and 15 days (Day 15) following administration of 1.0 mg/kg hOTC mRNA lipid nanoparticles produced by Process B.

FIG. 21 shows the plasma ammonia in animals 40 minutes after being subjected to an ammonia challenge, for each of wildtype mice (WT), untreated spf$^{ash}$ mice (Untreated), and spf$^{ash}$ mice at 24 hours (Day 2), 48 hours (Day 3), 72 hours (Day 4), 96 hours (Day 5), 8 days (Day 8), 11 days (Day 11), and 15 days (Day 15) following administration of 1.0 mg/kg hOTC mRNA lipid nanoparticles produced by Process B. The dashed line represents the average plasma ammonia level of the wild-type control group (WT). As can be seen by the results depicted in the figure, a single dose of the hOTC mRNA lipid nanoparticles provides significant protection against hyperammonemia for at least 15 days. Specifically, the plasma ammonia levels post challenge are comparable to wild type levels (WT) or far less than untreated levels (Untreated) at all the time points assessed out to 15 days.

Figure 22:
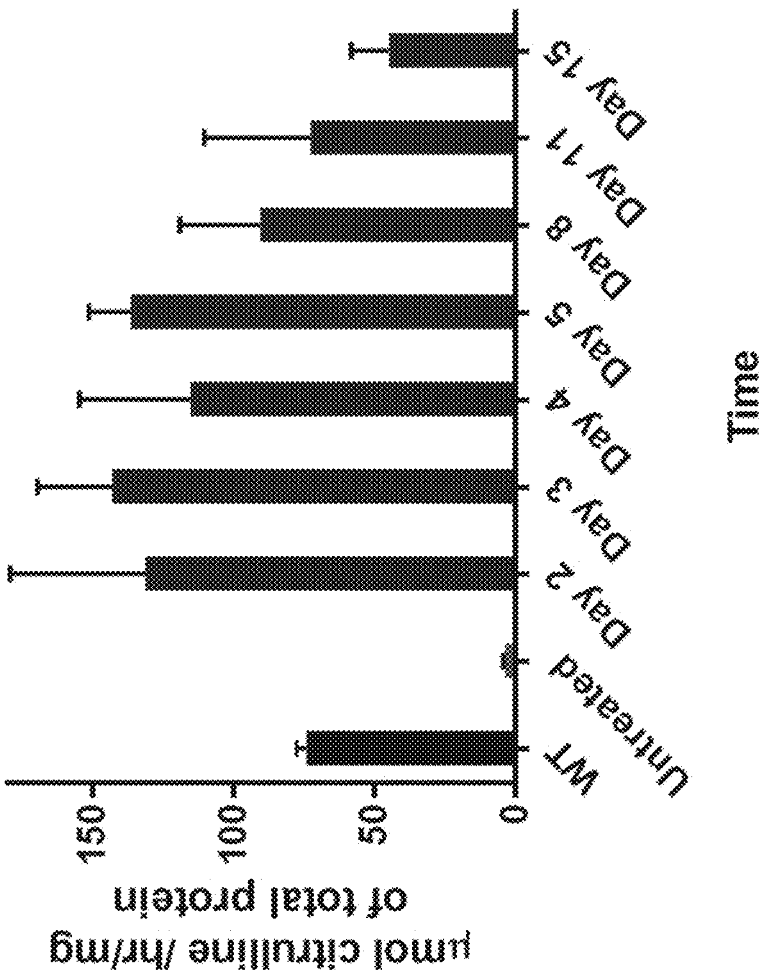
FIG. 22 shows hOTC protein activity as measured by citrulline production in each of wildtype mice (WT), untreated spf$^{ash}$ mice (Untreated), and spf$^{ash}$ mice at 24 hours (Day 2), 48 hours (Day 3), 72 hours (Day 4), 96 hours (Day 5), 8 days (Day 8), 11 days (Day 11), and 15 days (Day 15) following administration of 1.0 mg/kg hOTC mRNA lipid nanoparticles produced by Process B.

FIG. 22 shows the hOTC protein activity as measured by citrulline production in each of wildtype mice (WT), untreated spf$^{ash}$ mice (Untreated), and spf$^{ash}$ mice at 24 hours (Day 2), 48 hours (Day 3), 72 hours (Day 4), 96 hours (Day 5), 8 days (Day 8), 11 days (Day 11), and 15 days (Day 15) following administration of 1.0 mg/kg hOTC mRNA lipid nanoparticles produced by Process B. As can be seen by the results depicted in the figure, a single dose of hOTC mRNA lipid nanoparticles provides a resulting citrulline level that exceeds or is comparable to the wild type control (WT) and far exceeds the untreated control (Untreated) at all the time points assessed out to 15 days.

Figure 23:
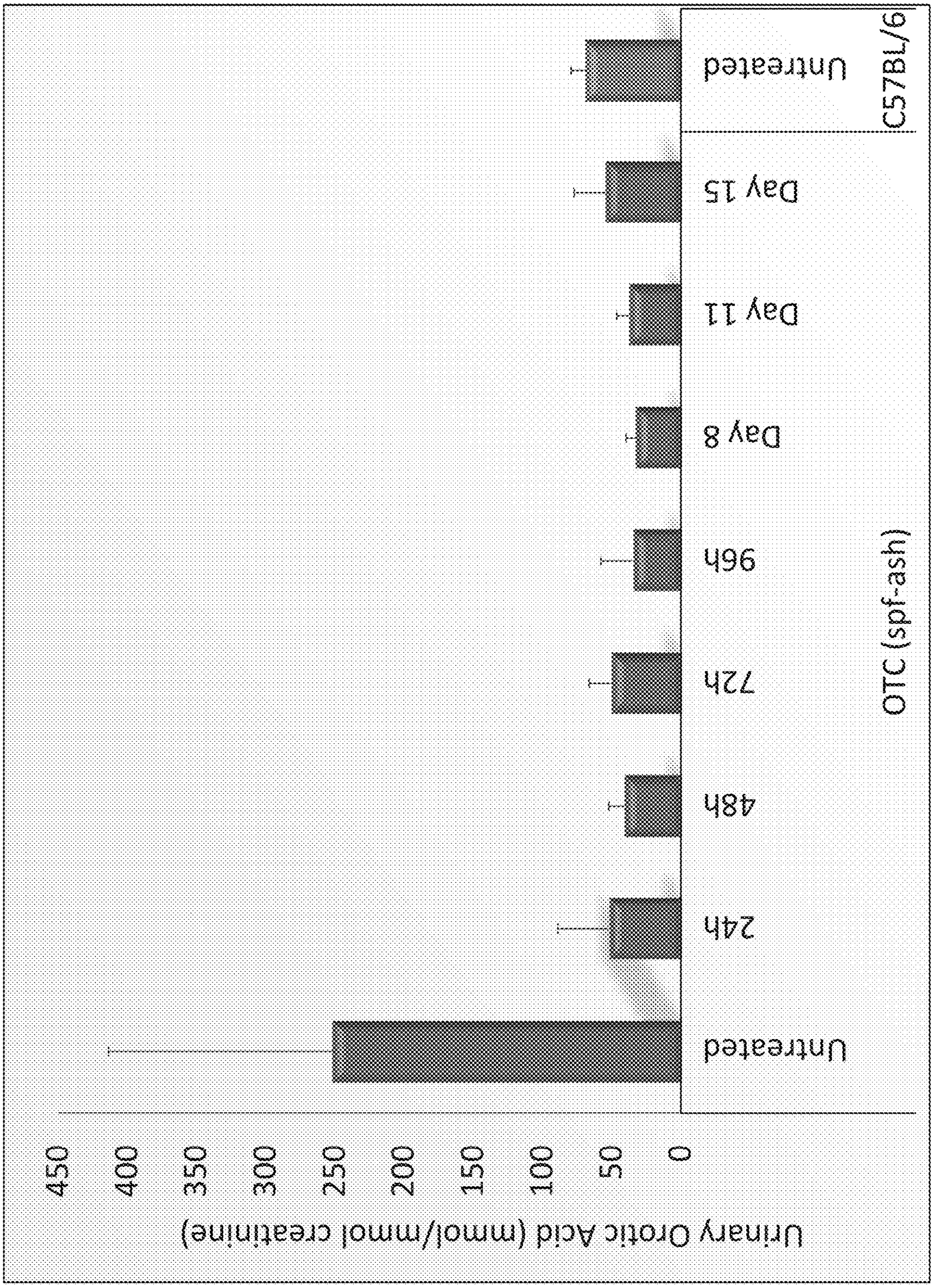
FIG. 23 shows hOTC protein activity as measured by maintained low levels of urinary orotic acid production in each of untreated spf$^{ash}$ mice (Untreated), spf$^{ash}$ mice at 24 hours (Day 2), 48 hours (Day 3), 72 hours (Day 4), 96 hours (Day 5), 8 days (Day 8), 11 days (Day 11), and 15 days (Day 15) following administration of 1.0 mg/kg hOTC mRNA lipid nanoparticles produced by Process B, and untreated wildtype mice (Untreated C57BL/6).

FIG. 23 shows the hOTC protein activity as measured by maintained low levels of urinary orotic acid production in each of untreated spf$^{ash}$ mice (Untreated), spf$^{ash}$ mice at 24 hours (Day 2), 48 hours (Day 3), 72 hours (Day 4), 96 hours (Day 5), 8 days (Day 8), 11 days (Day 11), and 15 days (Day 15) following administration of 1.0 mg/kg hOTC mRNA lipid nanoparticles produced by Process B, and untreated wildtype mice (Untreated C57BL/6). As can be seen by the results depicted in the figure, a single dose of hOTC mRNA lipid nanoparticles provides a resulting low level of urinary orotic acid that is less than or is comparable to the wild type control (Untreated C57BL/6) and is far less than the untreated spf$^{ash}$ mice (Untreated) at all the time points assessed out to 15 days.

Taken together, the data in this example shows that a single intravenous administration of an exemplary mRNA lipid nanoparticle produced by Process B yields active protein that is active across several measures for at least 15 days.

Example 16. In Vivo Activity of the Expressed hOTC in spf$^{ash}$ Mice at Various Doses This example illustrates that hOTC mRNA, at three different dose levels (1.0 mg/kg, 0.6 mg/kg, and 0.3 mg/kg), delivered via lipid nanoparticles produced by Process B were unexpectedly more potent than those produced by Process A at each dose evaluated.

In this example, OTC spf$^{ash}$ mice were administered a single intravenous dose (at varying concentrations, i.e., 1 mg/kg, 0.6 mg/kg, or 0.3 mg/kg) of hOTC mRNA encapsulated in lipid nanoparticles produced by Process A or Process B. The liver tissues from these mice were analyzed 24 hours after administration for citrulline production.

Figure 24:
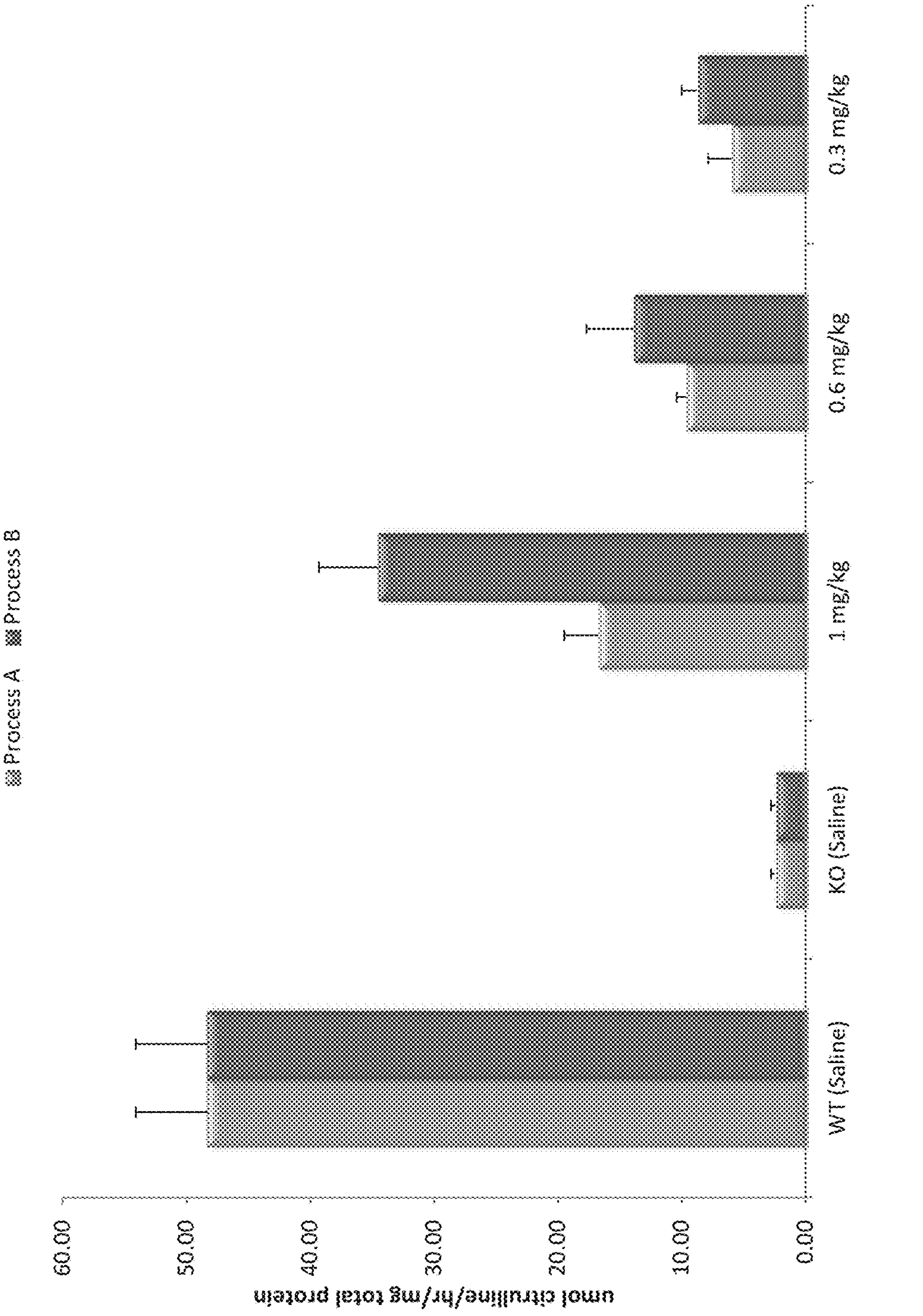
FIG. 24 depicts exemplary activity of expressed hOTC protein (in terms of citrulline production) in livers of OTC $spf^{ash}$ mice 24 hours after a single intravenous dose at different dose levels of hOTC mRNA encapsulated in lipid nanoparticle formulations made by Process A or by Process B.

FIG. 24 depicts exemplary activity of expressed hOTC protein (in terms of citrulline production) in livers of OTC spf$^{ash}$ mice 24 hours after a single intravenous dose of hOTC mRNA encapsulated in lipid nanoparticle formulations made by Process A or Process B. The hOTC mRNA was administered at different dosing levels of 1.0 mg/kg, 0.6 mg/kg, and 0.3 mg/kg.

Generally, the production of citrulline can be used to evaluate the activity of the expressed hOTC protein. As shown in FIG. 24, citrulline activity due to expressed hOTC protein in OTC spf$^{ash}$ mice liver was measured 24 hours after the single dose of the lipid nanoparticle mRNA formulation made by Process A and Process B, respectively, at various dose levels. The graph in FIG. 24 illustrates the citrulline activity due to expressed hOTC after the delivery of the lipid nanoparticle mRNA formulation by Process A and Process B, formulated per the processes described above.

The results shown in FIG. 24 indicate that the formulation prepared by Process B with pre-formed empty lipid nanoparticles resulted in higher citrulline activity of hOTC protein when compared to the formulation prepared by Process A.

Figure 25:
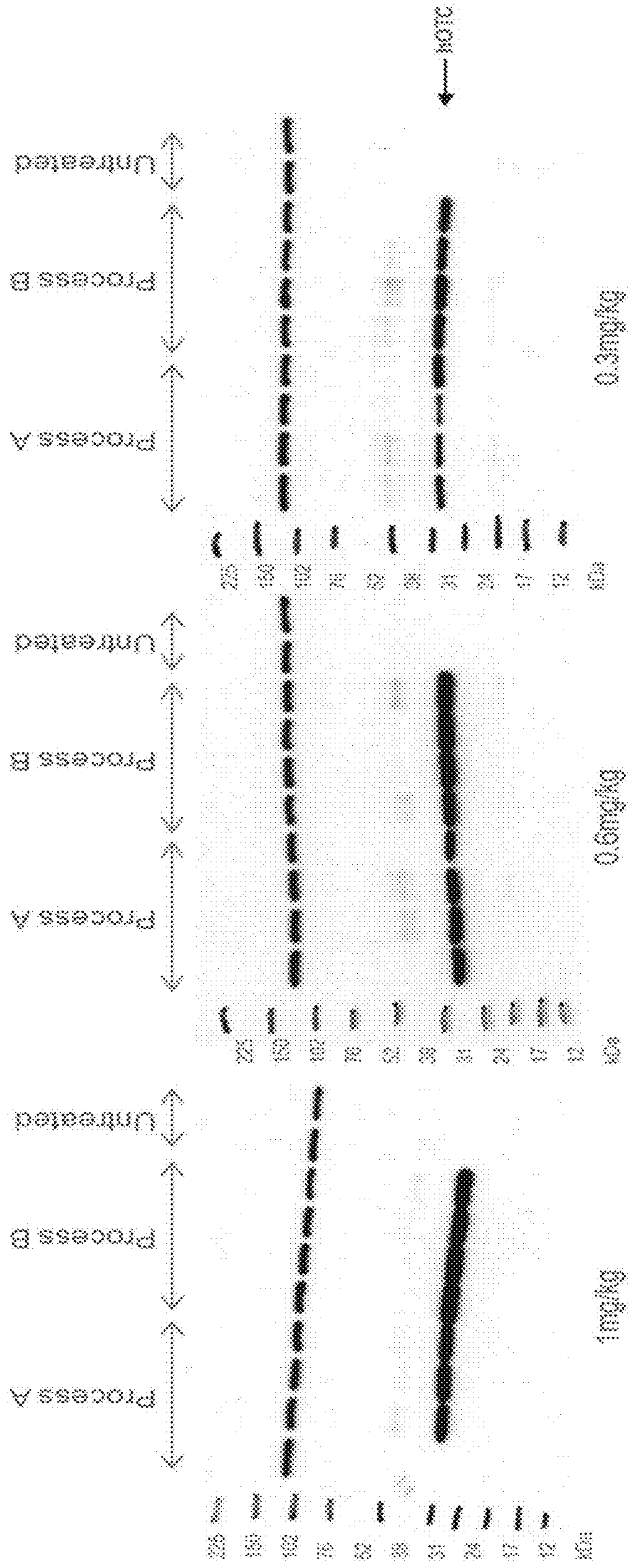
FIG. 25 depicts the immunohistochemical detection of expressed hOTC protein in the mice livers by Western blot after a single intravenous dose of hOTC mRNA encapsulated in lipid nanoparticle formulations made by Process A or by Process B at various dosing levels.

FIG. 25 depicts the immunohistochemical detection of hOTC protein in the mice livers by Western blot images after the single intravenous dose of hOTC mRNA encapsulated in lipid nanoparticle formulations made by Process A or Process B at various dosing levels (i.e., 1.0 mg/kg, 0.6 mg/kg, and 0.3 mg/kg). As shown in the Figure, at all three doses, the hOTC protein expressed was higher for the group dosed by lipid nanoparticle formulation made by Process B as compared to Process A, as evidenced by intensity of the bands.

Example 17. In Vivo Activity of the Expressed hOTC in spf$^{ash}$ Mice

This example illustrates that hOTC mRNA delivered via lipid nanoparticles produced by Process B were unexpectedly more effective than those produced by Process A.

Figure 26:
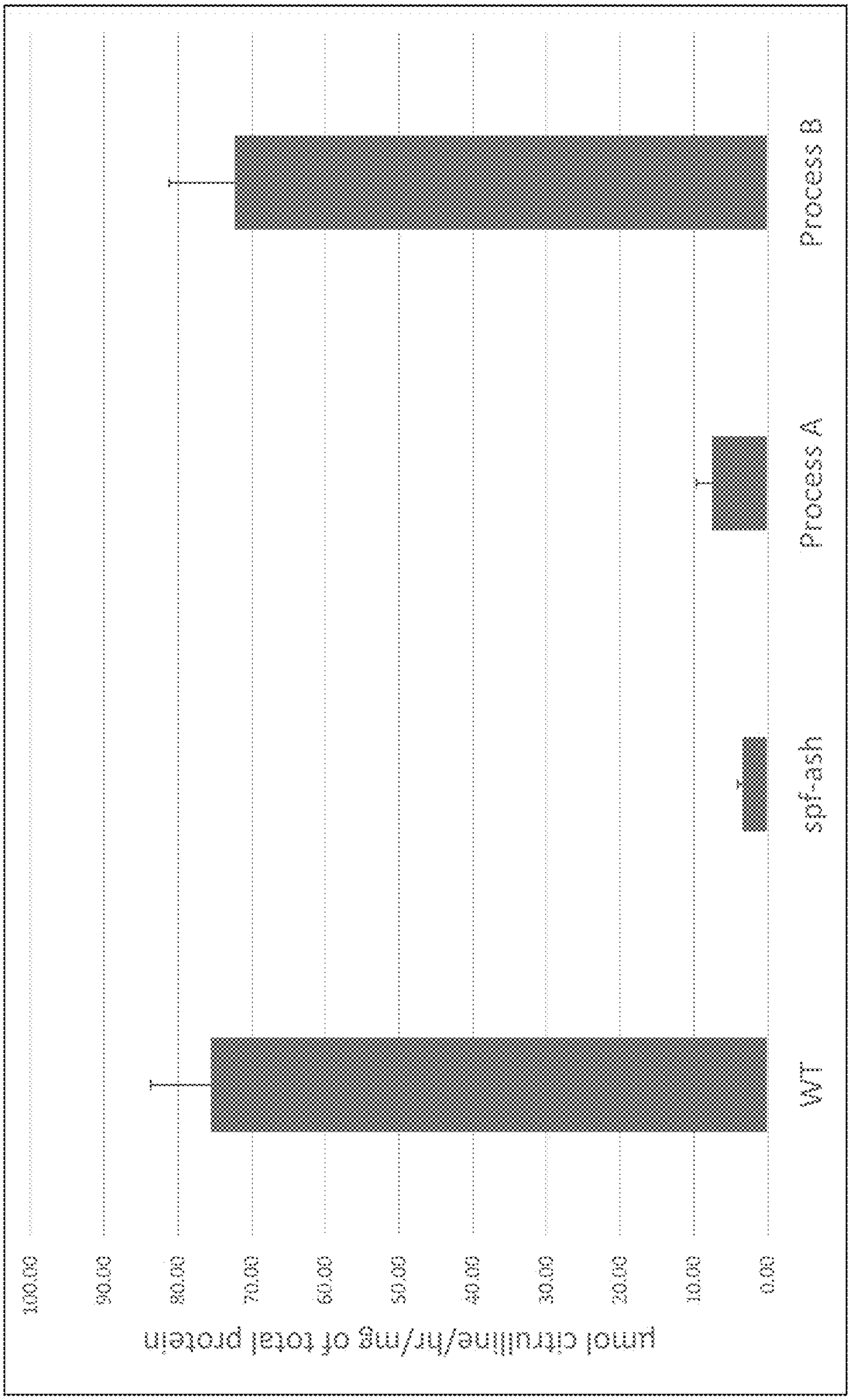
FIG. 26 depicts exemplary activity of expressed hOTC protein (in terms of citrulline production) in livers of OTC $spf^{ash}$ mice 24 hours after a single intravenous 0.5 mg/kg dose of hOTC mRNA encapsulated in lipid nanoparticle formulations made by Process B, as compared to those made by Process A.
Figure 27A:
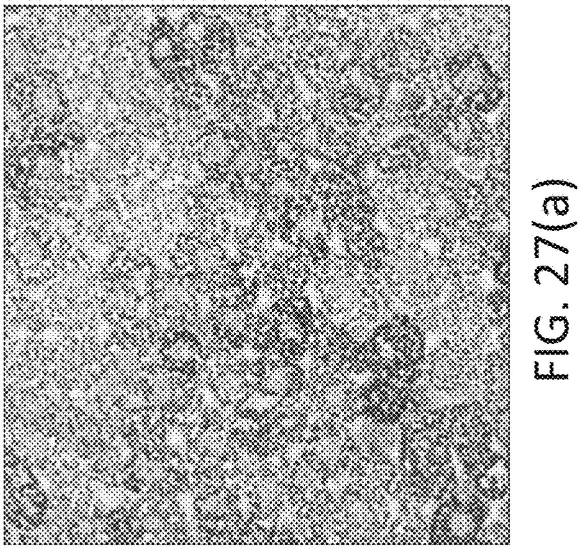
FIG. 27(*a*)-(*d*) shows the immunohistochemical detection of hOTC protein in mouse liver tissue 24 hours after dosing of hOTC mRNA lipid nanoparticles prepared by Process A or by Process B via immunohistochemical staining.
Figure 27B:
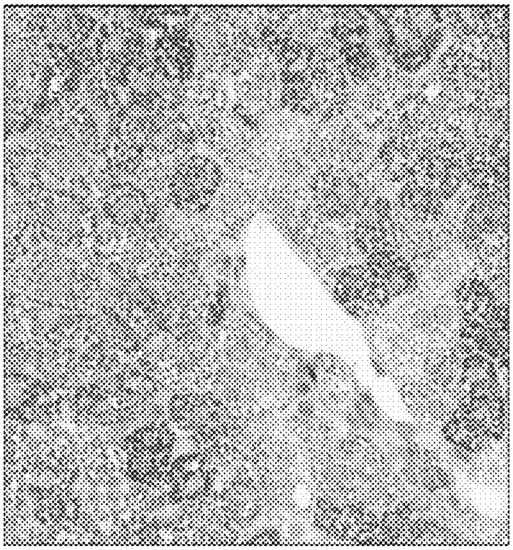
Figure 27C:
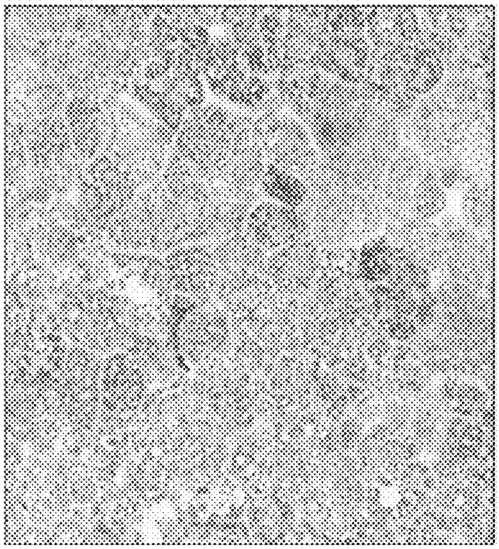
Figure 27D:
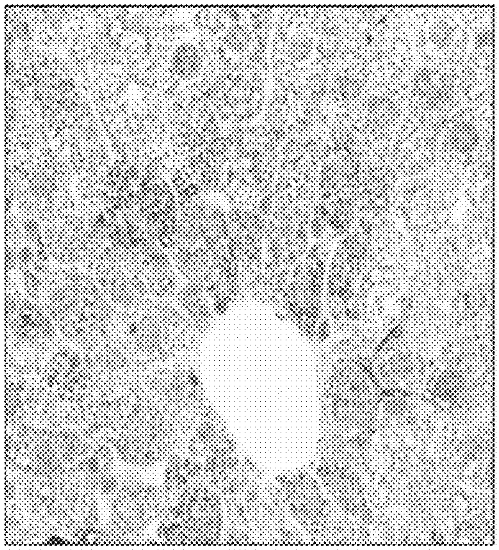

FIG. 26 depicts exemplary activity of expressed hOTC protein (in terms of citrulline production) in livers of OTC spf$^{ash}$ mice 24 hours after a single intravenous 0.5 mg/kg dose of hOTC mRNA encapsulated in lipid nanoparticle formulations made by Process A or Process B.

Generally, the production of citrulline can be used to evaluate the activity of the expressed hOTC protein. As shown in FIG. 26, citrulline activity due to expressed hOTC protein in OTC spf$^{ash}$ mice liver was measured 24 hours after the dose was administered and the results indicate that, at equal doses, the formulation prepared by Process B resulted in higher citrulline activity of hOTC protein as compared to the formulation prepared by Process A.

FIG. 27(*a*)-(*d*) shows the immunohistochemical detection of hOTC protein in mouse livers 24 hours after dosing of hOTC mRNA lipid nanoparticles prepared by Process A or Process B via immunohistochemical staining. As can be seen in the Figure, the staining of hOTC protein is stronger for the mice group dosed with LMP formulation prepared by Process B (FIG. 27(*a*)-(*b*)), as compared to Process A (FIG. 27(*c*)-(*d*)). The results shown in FIG. 27(*a*)-(*d*) agree with the higher citrulline production of the dose of the formulation prepared by Process B as compared to Process A, as depicted in FIG. 26.

Example 18. In vivo Expression of mRNA Lipid Nanoparticle Formulations Prepared by Process B and Process A Using Different Cationic Lipids This example illustrates that EPO mRNA delivered via lipid nanoparticles (consisting of a variety of different cationic lipids) produced by Process B were unexpectedly more effective than those produced by Process A.

In this study, male CD1 mice were administered on Day 1 a single intravenous tail vein injection at a dose of 1.0 mg/kg hEPO mRNA lipid nanoparticles each prepared using one of five different cationic lipids and produced by Process A or by Process B (as described earlier).

Table 4 provides the particular hEPO protein expression levels as measured in the serum of the animals sacrificed at 6 hours post administration of the hEPO mRNA lipid nanoparticles each prepared using one of five different cationic lipids and produced by Process A or by Process B, as measured by ELISA. As these results show, the hEPO protein expressed, as measured in the serum of the mice, from the mRNA lipid nanoparticles prepared by Process B was substantially higher than the same mRNA lipid nanoparticles prepared by Process A, across all the different cationic lipids evaluated. The percent increase ranged from 133% to 603%, with a consistent increase of greater than 100% potency observed across the 5 different lipids tested in the study.

Figure 28:
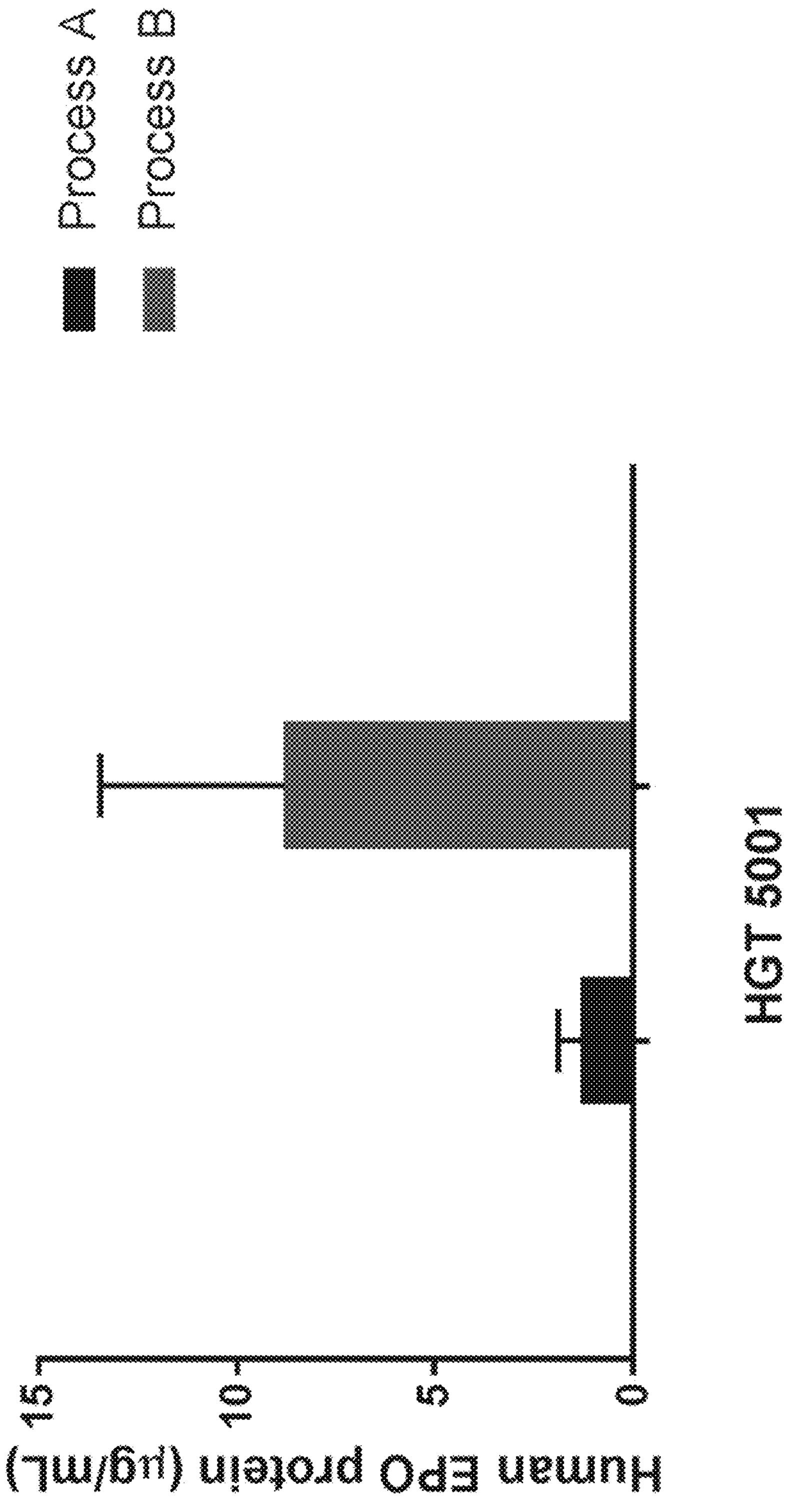
FIG. 28 depicts hEPO protein expression after the delivery of the lipid nanoparticle mRNA formulation produced by Process A and Process B, formulated using HGT 5001 as the cationic lipid.
Figure 29:
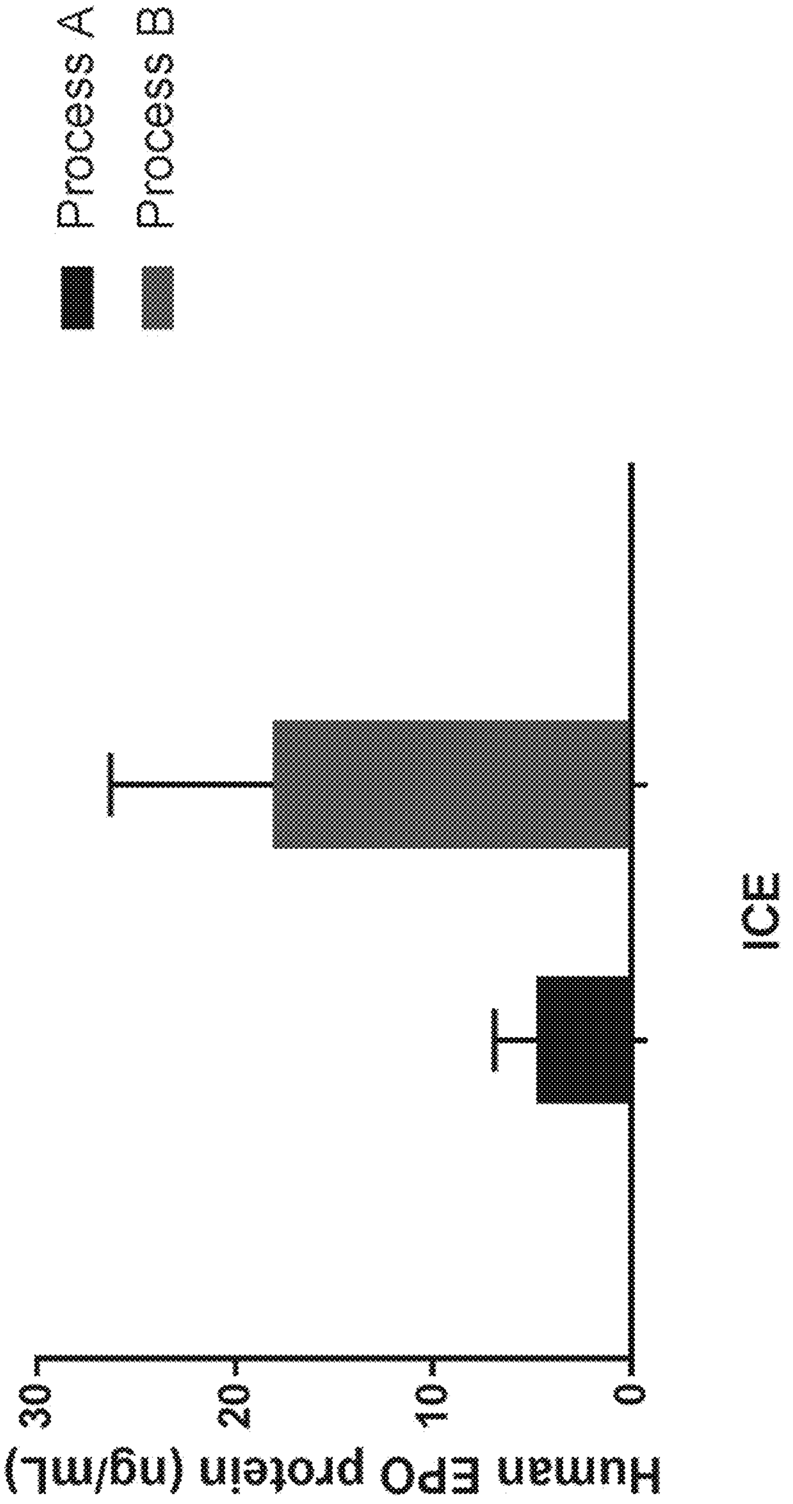
FIG. 29 depicts hEPO protein expression after the delivery of the lipid nanoparticle mRNA formulation produced by Process A and Process B, formulated using ICE as the cationic lipid.
Figure 30:
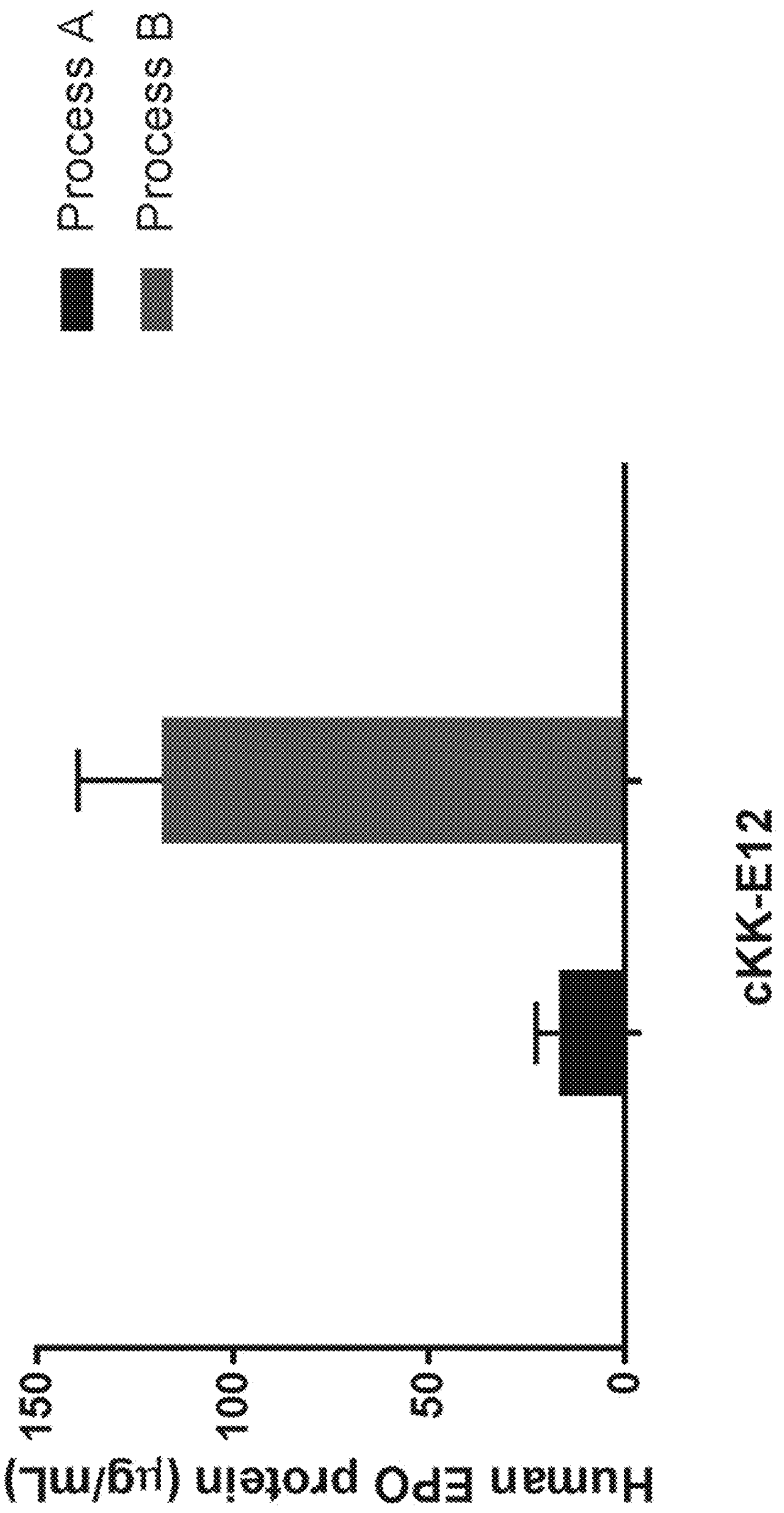
FIG. 30 depicts hEPO protein expression after the delivery of the lipid nanoparticle mRNA formulation produced by Process A and Process B, formulated using cKK-E12 as the cationic lipid.
Figure 31:
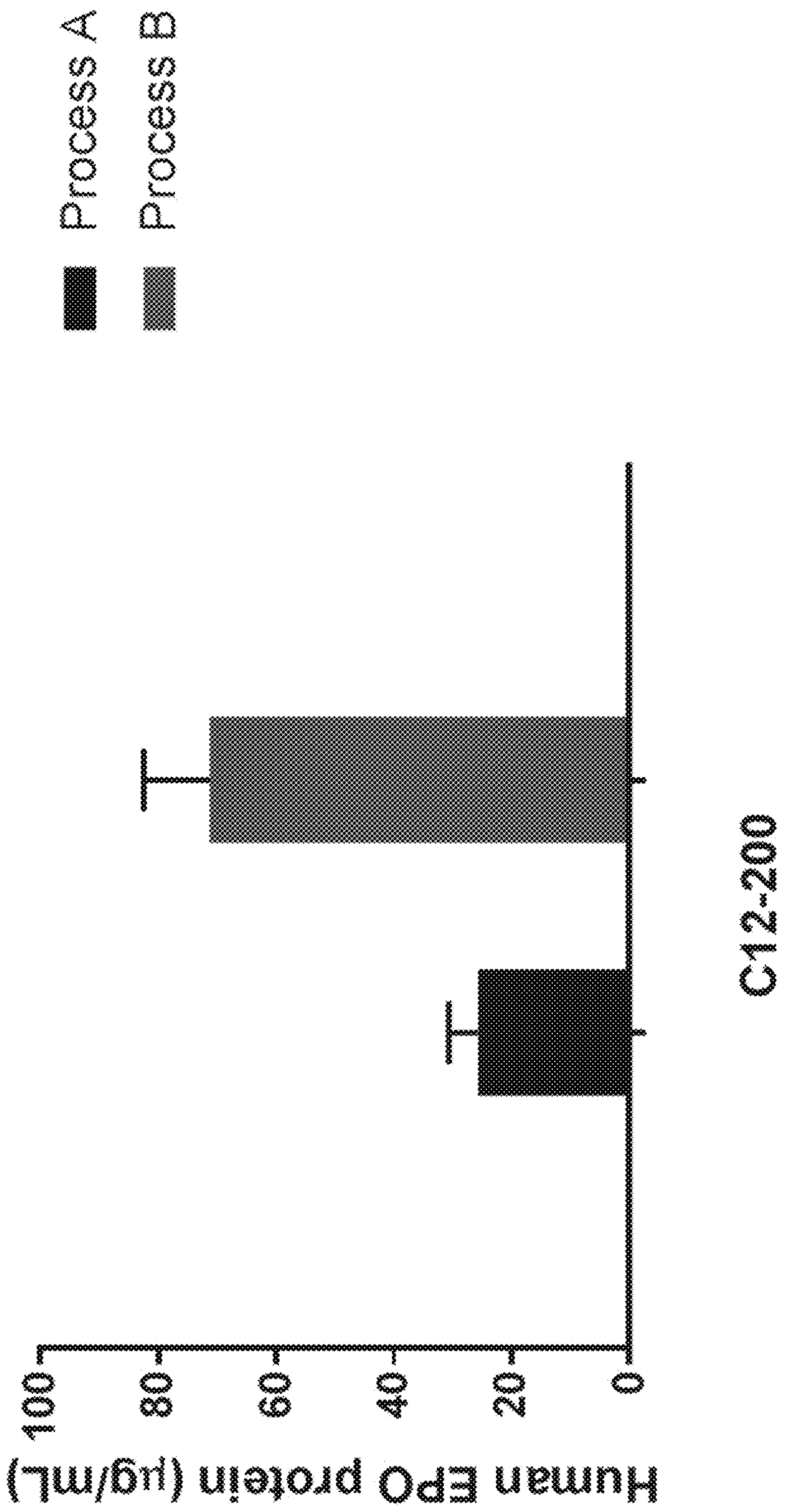
FIG. 31 depicts hEPO protein expression after the delivery of the lipid nanoparticle mRNA formulation produced by Process A and Process B, formulated using C12-200 as the cationic lipid.
Figure 32:
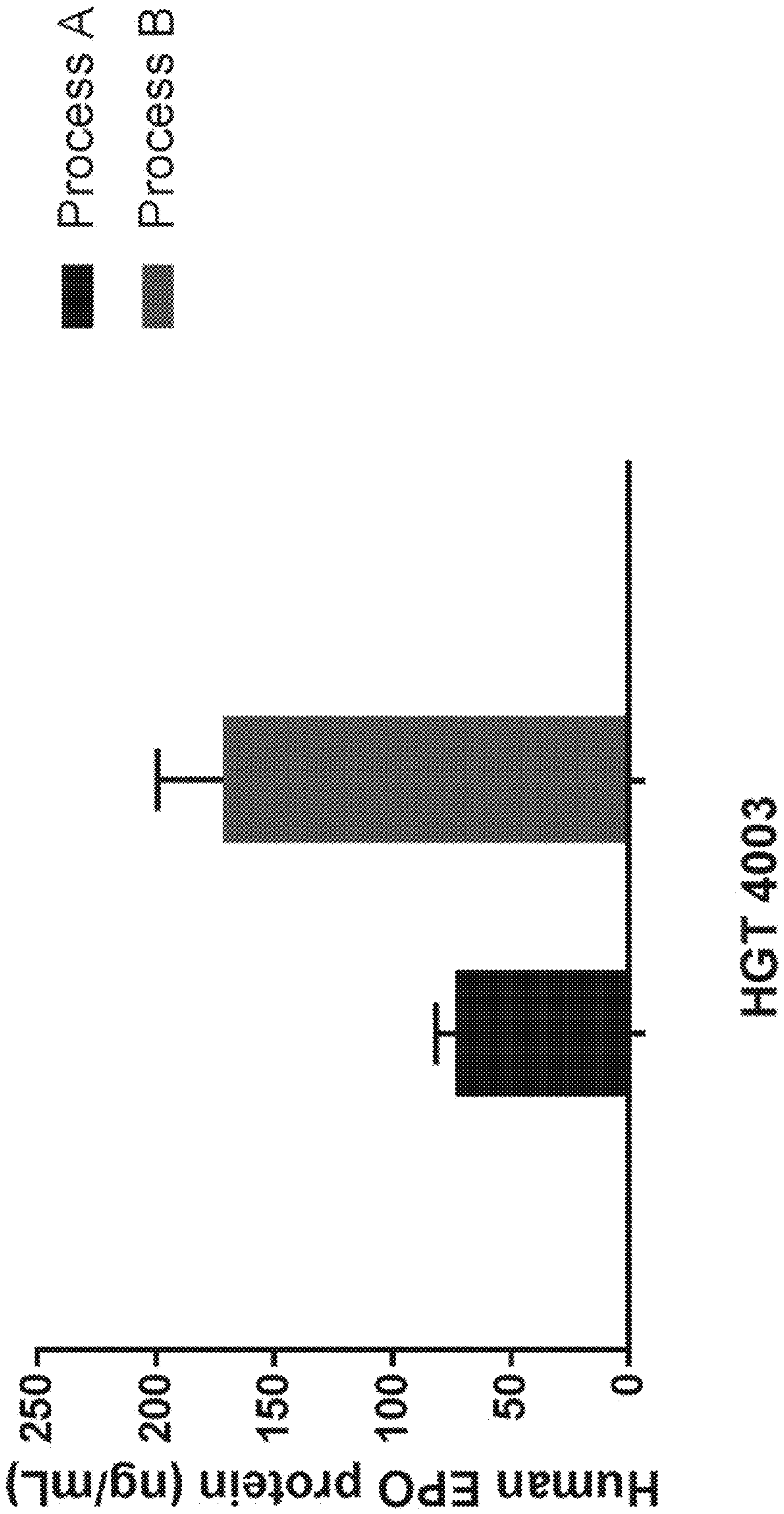
FIG. 32 depicts hEPO protein expression after the delivery of the lipid nanoparticle mRNA formulation produced by Process A and Process B, formulated using HGT 4003 as the cationic lipid.

FIG. 28 depicts hEPO protein expression after the delivery of the lipid nanoparticle mRNA formulation produced by Process A and Process B, formulated using HGT 5001 as the cationic lipid. FIG. 29 depicts hEPO protein expression after the delivery of the lipid nanoparticle mRNA formulation produced by Process A and Process B, formulated using ICE as the cationic lipid. FIG. 30 depicts hEPO protein expression after the delivery of the lipid nanoparticle mRNA formulation produced by Process A and Process B, formulated using cKK-E12 as the cationic lipid. FIG. 31 depicts hEPO protein expression after the delivery of the lipid nanoparticle mRNA formulation produced by Process A and Process B, formulated using C12-200 as the cationic lipid. FIG. 32 depicts hEPO protein expression after the delivery of the lipid nanoparticle mRNA formulation produced by Process A and Process B, formulated using HGT 4003 as the cationic lipid. As the results in each of these FIGS. 28-32 graphs show, the hEPO protein expressed, as measured in the serum of the mice, from the mRNA lipid nanoparticles prepared by Process B was substantially higher than the same mRNA lipid nanoparticles prepared by Process A, across all five different cationic lipids evaluated.

TABLE 4

In vivo Human EPO protein expression measured in mouse serum 6 hours following administration of hEPO mRNA lipid nanoparticles (across a variety of cationic lipids) formulated by Process A or Process B.

| | Human EPO protein measured in mouse serum 6 hours post dosing (μg/mL) | | |
|---|---|---|---|
| Lipid | Process A | Process B | % increase |
| HGT 5001 | 1.33 ± 0.56 | 8.83 ± 4.63 | 565% |
| ICE | 0.0048 ± 0.002 | 0.0181 ± 0.008 | 279% |
| cKK-E12 | 16.82 ± 5.92 | 118.4 ± 21.3 | 603% |
| C12-200 | 25.7 ± 4.9 | 71.3 ± 11.3 | 176% |
| HGT 4003 | 0.073 ± 0.008 | 0.172 ± 0.027 | 133% |

Table 5 depicts structural details of hEPO lipid nanoparticles prepared by Process A or Process B, using various cationic lipids. In particular, Table 5 depicts nanoparticle size (nm) and PdI of hEPO lipid nanoparticles when different cationic lipids are employed, as prepared by Process A or Process B. As shown in the Table, the nanoparticle sizes of hEPO mRNA lipid nanoparticles prepared by Process B were between about 90 nm and 150 nm across all nanoparticles prepared using the five different cationic lipids evaluated whereas those prepared by Process A were between about 75 nm and 95 nm across all nanoparticles prepared using the five cationic lipids evaluated.

TABLE 5

| Group # | Cationic Lipid | Concentration (mg/ml) | Type | Size (nm) | PdI |
|---|---|---|---|---|---|
| 1 | N/A (Saline) | N/A | N/A | N/A | N/A |
| 2 | HGT5001 | 0.2 | Process A | 85.21 | 0.26 |
| 3 | HGT 5001 | 0.2 | Process B | 128.3 | 0.16 |
| 4 | ICE | 0.2 | Process A | 79.02 | 0.27 |
| 5 | ICE | 0.2 | Process B | 147.4 | 0.23 |
| 6 | cKK-E12 | 0.2 | Process A | 91.55 | 0.19 |
| 7 | cKK-E12 | 0.2 | Process B | 126 | 0.16 |
| 8 | C12-200 | 0.2 | Process A | 77.12 | 0.204 |
| 9 | C12-200 | 0.2 | Process B | 116 | 0.18 |
| 10 | HGT4003 | 0.2 | Process A | 89.31 | 0.2 |
| 11 | HGT4003 | 0.2 | Process B | 91.05 | 0.16 |

Taken together, the data in this example shows that there is a substantial increase in potency for mRNA lipid nanoparticles produced by Process B as compared to by Process A, across lipid nanoparticles comprising various different lipid components.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A process of encapsulating messenger RNA (mRNA) in lipid nanoparticles comprising:

(a) providing a lipid mixture comprising a cationic lipid, a non-cationic lipid, a polyethylene glycol (PEG)-modified lipid, and a cholesterol-based lipid dissolved in ethanol, at a total lipid concentration of up to 100 mg/ml;

(b) mixing the lipid mixture with citrate buffer using a pump system to obtain a solution comprising pre-formed, empty lipid nanoparticles in citrate buffer containing ethanol, wherein the pre-formed, empty lipid nanoparticles are of a homogenous particle size of less than 150 nm;

(c) buffer-exchanging the solution comprising the pre-formed, empty lipid nanoparticles into an aqueous solution comprising one or more of trehalose, sucrose, lactose, and mannitol to remove the citrate buffer and ethanol;

(d) mixing the aqueous solution comprising the pre-formed, empty lipid nanoparticles with an aqueous solution comprising mRNA at a concentration of up to 5.0 mg/ml and a pH of about 3.5-6.5; wherein said mixing takes place in the presence of less than 1% ethanol and less than 1 mM citrate; and (e) heating the lipid nanoparticle and mRNA solution obtained in step (d) at a temperature of or greater than 50° C.

2. The process of claim 1, wherein mixing the aqueous solution comprising the pre-formed, empty lipid nanoparticles with the aqueous solution comprising the mRNA takes place in the absence of ethanol.

3. The process of claim 1, wherein mixing the aqueous solution comprising the pre-formed, empty lipid nanoparticles with the aqueous solution comprising the mRNA takes place in the absence of citrate buffer.

4. The process of claim 1, wherein the cationic lipid constitutes about 30-55% by molar ratio of the lipid mixture.

5. The process of claim 1, wherein the cholesterol-based lipid constitutes about 30-50% by molar ratio of the lipid mixture.

6. The process of claim 1, wherein the aqueous solution comprising the mRNA contains a buffering agent.

7. The process of claim 6, wherein the buffering agent is selected from the group consisting of sodium bicarbonate, sodium acetate, potassium phosphate and sodium phosphate.

8. The process of claim 6, wherein the buffering agent is at a concentration of 0.1 mM to 100 mM.

9. The process of claim 1, wherein the aqueous solution comprising the mRNA contains a salt.

10. The process of claim 9, wherein the salt is selected from the group consisting of sodium chloride, magnesium chloride, and potassium chloride.

11. The process of claim 9, wherein the salt is at a concentration of 1 mM to 500 mM.

12. The method of claim 1, wherein the pump system comprises a pulse-less flow pump.

13. The method of claim 1, wherein the citrate buffer contains about 10 mM citrate, about 150 mM NaCl, and has a pH of about 4.5.

14. The process of claim 1, wherein the pump system maintains a lipid/mRNA ratio that is constant throughout the process.

15. The method of claim 1, wherein the non-cationic lipid constitutes at least about 5% by molar ratio of the total lipid mixture.

16. The method of claim 1, wherein the PEG-modified lipid comprises a poly (ethylene) glycol chain of up to 5 kDa in length covalently attached to a lipid with alkyl chain(s) of $C_6$-$C_{20}$ length.

17. The method of claim 1, wherein the cholesterol-based lipid is cholesterol.

18. The method of claim 1, wherein the non-cationic lipid is distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, or 18-1-trans PE, 1-stearoyl-2-oleoyl-phosphatidyethanolamine (SOPE).

19. A process of encapsulating messenger RNA (mRNA) in lipid nanoparticles comprising:

(a) providing pre-formed, empty lipid nanoparticles comprising a cationic lipid, a non-cationic lipid, a polyethylene glycol (PEG)-modified lipid, and a cholesterol-based lipid in an aqueous solution comprising one or more of trehalose, sucrose, lactose, and mannitol;

(b) mixing the aqueous solution comprising the pre-formed, empty lipid nanoparticles with an aqueous solution comprising mRNA at a concentration of up to 5.0 mg/ml and a pH of about 3.5-6.5; wherein said mixing takes place in the presence of less than 1% ethanol and less than 1 mM citrate; and (c) heating the lipid nanoparticle and mRNA solution obtained in step (b) at a temperature of about or greater than 50° C.

20. The process of claim 19, wherein the pre-formed, empty lipid nanoparticles are stably-stored in frozen form.

* * * * *

SEQUENCE LISTING

```
Sequence total quantity: 5
SEQ ID NO: 1            moltype = RNA  length = 1065
FEATURE                 Location/Qualifiers
misc_feature            1..1065
                        note = chemically synthesized oligonucleotide
source                  1..1065
                        mol_type = other RNA
                        organism = synthetic construct
SEQUENCE: 1
atgctgttca accttcggat cttgctgaac aacgctgcgt tccggaatgg tcacaacttc  60
atggtccgga acttcagatg cggccagccg ctccagaaca aggtgcagct caaggggagg  120
gacctcctca ccctgaaaaa cttcaccgga gaagagatca agtacatgct gtggctgtca  180
gccgacctca aattccggat caagcagaag ggcgaatacc ttcctttgct gcagggaaag  240
tccctgggga tgatcttcga gaagcgcagc actcgcacta gactgtcaac tgaaaccggc  300
ttcgcgctgc tgggaggaca cccctgcttc ctgaccaccc aagatatcca tctgggtgtg  360
aacgaatccc tcaccgacac agcgcgggtg ctgtcgtcca tggcagacgc ggtcctcgcc  420
cgcgtgtaca agcagtctga tctggacact ctggccaagg aagcctccat tcctatcatt  480
aatggattgt ccgacctcta ccatcccatc cagattctgg ccgattatct gactctgcaa  540
gaacattaca gctccctgaa ggggcttacc ctttcgtgga tcggcgacgg caacaacatt  600
ctgcacagca ttatgatgag cgctgccaag tttggaatgc acctccaagc agcgaccccg  660
aagggatacg agccagacgc ctccgtgacg aagctggctg agcagtacgc caaggagaac  720
ggcactaagc tgctgctcac caacgaccct ctcgaagccg cccacggtgg caacgtgctg  780
atcaccgata cctggatctc catgggacag gaggaggaaa agaagaagcg cctgcaagca  840
tttcaggggt accaggtgac tatgaaaacc gccaaggtcg ccgcctcgga ctggaccttc  900
ttgcactgtc tgcccagaaa gcccgaagag gtggacgacg aggtgttcta cagcccgcgg  960
tcgctggtct ttccggaggc cgaaaacagg aagtggacta tcatggccgt gatggtgtcc  1020
ctgctgaccg attactcccc gcagctgcag aaaccaaagt tctga                  1065

SEQ ID NO: 2            moltype = RNA  length = 1239
FEATURE                 Location/Qualifiers
misc_feature            1..1239
                        note = chemically synthesized oligonucleotide
source                  1..1239
                        mol_type = other RNA
                        organism = synthetic construct
SEQUENCE: 2
atgagcagca agggcagcgt ggtgctggcc tacagcggcg gcctggacac cagctgcatc  60
ctggtgtggc tgaaggagca gggctacgac gtgatcgcct acctggccaa catcggccag  120
aaggaggact tcgaggaggc ccgcaagaag gccctgaagc tgggcgccaa gaaggtgttc  180
atcgaggacg tgagccgcga gttcgtggag gagttcatct ggcccgccat ccagagcagc  240
gccctgtacg aggaccgcta cctgctgggc accagcctgg cccgcccctg catcgcccgc  300
aagcaggtgg agatcgccca gcgcgagggc gccaagtacg tgagccacgg cgccaccggc  360
aagggcaacg accaggtgcg cttcgagctg agctgctaca gcctggcccc ccagatcaag  420
gtgatcgccc cctggcgcat gcccgagttc tacaaccgct tcaagggccg caacgacctg  480
atggagtacg ccaagcagca cggcatcccc atccccgtga cccccaagaa cccctggagc  540
atggacgaga acctgatgca catcagctac gaggccggca tcctggagaa ccccaagaac  600
caggcccccc ccggcctgta caccaagacc caggaccccg ccaaggcccc caacaccccc  660
gacatcctgg agatcgagtt caagaagggc gtgcccgtga aggtgaccaa cgtgaaggac  720
ggcaccaccc accagaccag cctggagctg ttcatgtacc tgaacgaggt ggccggcaag  780
cacggcgtgg gccgcatcga catcgtggag aaccgcttca tcggcatgaa gagccgcggc  840
atctacgaga cccccgccgg caccatcctg taccacgccc acctggacat cgaggccttc  900
accatggacc gcgaggtgcg caagatcaag cagggcctgg gcctgaagtt cgccgagctg  960
gtgtacaccg gcttctggca cagccccgag tgcgagttcg tgcgccactg catcgccaag  1020
agccaggagc gcgtggaggg caaggtgcag gtgagcgtgc tgaagggcca ggtgtacatc  1080
ctgggccgcg agagcccccct gagcctgtac aacgaggagc tggtgagcat gaacgtgcag  1140
ggcgactacg agcccaccga cgccaccggc ttcatcaaca tcaacagcct gcgcctgaag  1200
gagtaccacc gcctgcagag caaggtgacc gccaagtga                         1239

SEQ ID NO: 3            moltype = RNA  length = 4443
FEATURE                 Location/Qualifiers
misc_feature            1..4443
                        note = chemically synthesized oligonucleotide
source                  1..4443
                        mol_type = other RNA
                        organism = synthetic construct
SEQUENCE: 3
atgcaacgct ctcctcttga aaaggcctcg gtggtgtcca agctcttctt ctcgtggact  60
agacccatcc tgagaaaggg gtacagacag cgcttggagc tgtccgatat ctatcaaatc  120
ccttccgtgg actccgcgga caacctgtcc gagaagctcg agagagaatg ggacagagaa  180
ctcgcctcaa agaagaaccc gaagctgatt aatgcgctta ggcggtgctt tttctggcgg  240
ttcatgttct acggcatctt cctctacctg ggagaggtca ccaaggccgt gcagcccctg  300
ttgctgggac ggattattgc ctcctacgac cccgacaaca aggaagaaag aagcatcgct  360
atctacttgg gcatcggtct gtgcctgctt ttcatcgtcc ggaccctctt gttgcatcct  420
gctattttcg gcctgcatca cattggcatg cagatgagaa ttgccatgtt ttccctgatc  480
tacaagaaaa ctctgaagct ctcgagccgc gtgcttgaca agatttccat cggccagctc  540
gtgtccctgc tctccaacaa tctgaacaag ttcgacgagg gcctcgccct ggcccacttc  600
gtgtggatcg cccctctgca agtggcgctt ctgatgggcc tgatctggga gctgctgcaa  660
gcctcggcat tctgtgggct tggattcctg atcgtgctgg cactgttcca ggccggactg  720
```

-continued

```
gggcggatga tgatgaagta cagggaccag agagccggaa agatttccga acggctggtg  780
atcacttcgg aaatgatcga aaacatccag tcagtgaagg cctactgctg ggaagaggcc  840
atggaaaaga tgattgaaaa cctccggcaa accgagctga agctgacccg caaggccgct  900
tacgtgcgct atttcaactc gtccgctttc ttcttctccg ggttcttcgt ggtgtttctc  960
tccgtgctcc cctacgccct gattaaggga atcatcctca ggaagatctt caccaccatt  1020
tccttctgta tcgtgctccg catggccgtg acccggcagt tcccatgggc cgtgcagact  1080
tggtacgact ccctgggagc cattaacaag atccaggact tccttcaaaa gcaggagtac  1140
aagaccctcg agtacaacct gactactacc gaggtcgtga tggaaaacgt caccgccttt  1200
tgggaggagg gatttggcga actgttcgag aaggccaagc agaacaacaa caaccgcaag  1260
acctcgaacg gtgacgactc cctcttcttt tcaaacttca gcctgctcgg gacgcccgtg  1320
ctgaaggaca ttaacttcaa gatcgaaaga ggacagctcc tggcggtggc cggatcgacc  1380
ggagccggaa agacttccct gctgatggtg atcatgggag agcttgaacc tagcgaggga  1440
aagatcaagc actccggccg catcagcttc tgtagccagt ttcctggat catgcccgga  1500
accattaagg aaaacatcat cttcggcgtg tcctacgatg aataccgcta ccggtccgtg  1560
atcaaagcct gccagctgga agaggatatt tcaaagttcg cggagaaaga taacatcgtg  1620
ctgggcgaag gggtattac cttgtcgggg ggccagcggg ctagaatctc gctggccaga  1680
gccgtgtata aggacgccga cctgtatctc ctggactccc ccttcggata cctggacgtc  1740
ctgaccgaaa aggagatctt cgaatcgtgc gtgtgcaagc tgatggctaa caagactcgc  1800
atcctcgtga cctccaaaat ggagcacctg aagaaggcag acaagattct gattctgcat  1860
gaggggtcct cctactttta cggcaccttc tcggagttgc agaacttgca gcccgacttc  1920
tcatcgaagc tgatgggttg cgacagcttc gaccagttct ccgccgaaag aaggaactcg  1980
atcctgacgg aaaccttgca ccgcttctct ttggaaggcg acgcccctgt gtcatggacc  2040
gagactaaga agcagagctt caagcagacc ggggaattcg gcgaaaagag gaagaacagc  2100
atcttgaacc ccattaactc catccgcaag ttctcaatcg tgcaaaagac gccactgcag  2160
atgaacggca ttgaggagga ctccgacgaa ccccttgaga ggcgcctgtc cctggtgccg  2220
gacagcgagc agggagaagc catcctgcct cggatttccg tgatctccac tggtccgacg  2280
ctccaagccc ggcggcggca gtccgtgctg aacctgatga cccacagcgt gaaccagggc  2340
caaaacattc accgcaagac taccgcatcc acccggaaag tgtccctggc acctcaagcg  2400
aatcttaccg agctcgacat ctactcccgg agactgtcgc aggaaaccgg gctcgaaatt  2460
tccgaagaaa tcaacgagga ggatctgaaa gagtgcttct tcgacgatat ggagtcgata  2520
cccgccgtga cgacttggaa cacttatctg cggtacatca ctgtgcacaa gtcattgatc  2580
ttcgtgctga tttggtgcct ggtgatttc ctggccgagg tcgcggcctc actggtggtg  2640
ctctggctgt tgggaaacac gcctctgcaa gacaagggaa actccacgca ctcgagaaac  2700
aacagctatg ccgtgattat cacttccacc tcctcttatt acgtgttcta catctacgtc  2760
ggagtggcgg ataccctgct cgcgatgggt ttcttcagag gactgccgct ggtccacacc  2820
ttgatcaccg tcagcaagat tcttcaccac aagatgttgc atagcgtgct gcaggccccc  2880
atgtccaccc tcaacactct gaaggccgga ggcattctga acagattctc caaggacatc  2940
gctatcctgg acgatctcct gccgcttacc atctttgact tcatccagct gctgctgatc  3000
gtgattggag caatcgcagt ggtggcggtg ctgcagcctt acattttcgt ggccactgtg  3060
ccggtcattg tggcgttcat catgctgcgg gcctacttcc tccaaaccag ccagcagctg  3120
aagcaactgg aatccgaggg acgatccccc atcttcactc accttgtgac gtcgttgaag  3180
ggactgtgga ccctccgggc tttcggacgg cagccctact tcgaaaccct cttccacaag  3240
gccctgaacc tccacaccgc caattggttc ctgtacctgt ccaccctgcg gtggttccag  3300
atgcgcatcg agatgatttt cgtcatcttc ttcatcgcgg tcacattcat cagcatcctg  3360
actaccggag agggagaggg acgggtcgga ataatcctga ccctcgccat gaacattatg  3420
agcaccctgc agtgggcagt gaacagctcg atcgacgtgg acagcctgat gcgaagcgtc  3480
agccgcgtgt tcaagttcat cgacatgcct actgagggaa aacccactaa gtccactaag  3540
ccctacaaaa atggccagct gagcaaggtc atgatcatcg aaaactccca cgtgaagaag  3600
gacgatattt ggccctccgg aggtcaaatg accgtgaagg acctgaccgc aaagtacacc  3660
gagggaggaa acgccattct cgaaaacatc agcttctcca tttcgccggg acagcgggtc  3720
ggccttctcg ggcggaccgg ttccgggaag tcaactctgc tgtcggcttt cctccggctg  3780
ctgaataccg agggggaaat ccaaattgac ggcgtgtctt gggattccat tactctgcag  3840
cagtggcgga aggccttcgg cgtgatcccc cagaaggtgt tcatcttctc gggtaccttc  3900
cggaagaacc tggatcctta cgagcagtgg agcgaccaag aaatctggaa ggtcgccgac  3960
gaggtcggcc tgcgctccgt gattgaacaa tttcctggaa agctggactt cgtgctcgtc  4020
gacgggggat gtgtcctgtc gcacggacat aagcagctca tgtgcctcgc acggtccgtg  4080
ctctccaagg ccaagattct gctgctggac gaaccttcgg cccacctgga tccggtcacc  4140
taccagatca tcaggaggac cctgaagcag gcctttgccg attgcaccgt gattctctgc  4200
gagcaccgca tcgaggccat gctggagtgc cagcagttcc tggtcatcga ggagaacaag  4260
gtccgccaat acgactccat tcaaaagctc ctcaacgagc ggtcgctgtt cagacaagct  4320
atttcaccgt ccgatagagt gaagctcttc ccgcatcgga acagctcaaa gtgcaaatcg  4380
aagccgcaga tcgcagcctt gaaggaagag actgaggaag aggtgcagga cacccggctt  4440
taa                                                                4443
```

```
SEQ ID NO: 4           moltype = RNA  length = 4443
FEATURE                Location/Qualifiers
misc_feature           1..4443
                       note = chemically synthesized oligonucleotide
source                 1..4443
                       mol_type = other RNA
                       organism = synthetic construct
SEQUENCE: 4
atgcagcggt ccccgctcga aaaggccagt gtcgtgtcca aactcttctt ctcatggact  60
cggcctatcc ttagaaaggg gtatcggcag aggcttgagt tgtctgacat ctaccagatc  120
ccctcggtag attcggcgga taacctctcg gagaagctcg aacgggaatg ggaccgcgaa  180
ctcgcgtcta agaaaaaccc gaagctcatc aacgcactga gaaggtgctt cttctggcgg  240
ttcatgttct acggtatctt cttgtatctc ggggaggtca caaaagcagt ccaacccctg  300
ttgttgggtc gcattatcgc ctcgtacgac cccgataaca aagaagaacg gagcatcgcg  360
atctacctcg ggatcggact gtgtttgctt ttcatcgtca gaacactttt gttgcatcca  420
```

-continued

```
gcaatcttcg gcctccatca catcggtatg cagatgcgaa tcgctatgtt tagcttgatc  480
tacaaaaaga cactgaaact ctcgtcgcgg gtgttggata agatttccat cggtcagttg  540
gtgtccctgc ttagtaataa cctcaacaaa ttcgatgagg gactggcgct ggcacatttc  600
gtgtggattg ccccgttgca agtcgccctt ttgatgggcc ttatttggga gctgttgcag  660
gcatctgcct tttgtggcct gggatttctg attgtgttgg cattgtttca ggctgggctt  720
gggcggatga tgatgaagta tcgcgaccag agagcgggta aaatctcgga aagactcgtc  780
atcacttcgg aaatgatcga aaacatccag tcggtcaaag cctattgctg ggaagaagct  840
atggagaaga tgattgaaaa cctccgccaa actgagctga aactgacccg caaggcggcg  900
tatgtccggt atttcaattc gtcagcgttc ttcttttccg ggttcttcgt tgtctttctc  960
tcggttttgc cttatgcctt gattaagggg attatcctcc gcaagatttt caccacgatt  1020
tcgttctgca ttgtattgcg catggcagtg acacggcaat ttccgtgggc cgtgcagaca  1080
tggtatgact cgcttggagc gatcaacaaa atccaagact tcttgcaaaa gcaagagtac  1140
aagaccctgg agtacaatct tactactacg gaggtagtaa tggagaatgt gacggctttt  1200
tgggaagagg gttttggaga actgtttgag aaagcaaagc agaataacaa caaccgcaag  1260
acctcaaatg ggacgattc cctgttttc tcgaacttct ccctgctcgg aacacccgtg  1320
ttgaaggaca tcaatttcaa gattgagagg ggacagcttc tcgcggtagc gggaagcact  1380
ggtgcgggaa aaactagcct cttgatggtg attatggggg agcttgagcc cagcgagggg  1440
aagattaaac actccgggcg tatctcattc tgtagccagt tttcatggat catgcccgga  1500
accattaaag agaacatcat tttcggagta tcctatgatg agtaccgata cagatcggtc  1560
attaaggcgt gccagttgga agaggacatt tctaagttcg ccgagaagga taacatcgtc  1620
ttgggagaag gggtattac attgtcggga gggcagcgag cgcggatcag cctcgcgaga  1680
gcggtataca aagatgcaga tttgtatctg cttgattcac cgtttggata cctcgacgta  1740
ttgacagaaa aagaaatctt cgagtcgtgc gtgtgtaaac ttatggctaa taagacgaga  1800
atcctggtga catcaaaaat ggaacacctt aagaaggcgg acaagatcct gatcctccac  1860
gaaggatcgt cctactttta cggcactttc tcagagttgc aaaacttgca gccggacttc  1920
tcaagcaaac tcatggggtg tgactcattc gaccagttca gcgcggaacg gcggaactcg  1980
atcttgacgg aaacgctgca ccgattctcg cttgagggtg atgccccggt atcgtggacc  2040
gagacaaaga agcagtcgtt taagcagaca ggagaatttg gtgagaaaag aaagaacagt  2100
atcttgaatc ctattaactc aattcgcaag ttctcaatcg tccagaaaac tccactgcag  2160
atgaatggaa ttgaagagga ttcggacgaa cccctggagc gcaggcttag cctcgtgccg  2220
gattcagagc aaggggaggc cattcttccc cggatttcgg tgatttcaac cggacctaca  2280
cttcaggcga ggcgaaggca atccgtgctc aacctcatga cgcattcggt aaaccagggg  2340
caaaacattc accgcaaaac gacggcctca acgagaaaag tgtcacttgc accccaggcg  2400
aatttgactg aactcgacat ctacagccgt aggctttcgc aagaaaccgg acttgagatc  2460
agcgaagaaa tcaatgaaga agatttgaaa gagtgtttct ttgatgacat ggaatcaatc  2520
ccagcggtga caacgtggaa cacatacttg cgttacatca cggtgcacaa gtccttgatt  2580
ttcgtcctca tctggtgtct cgtgatcttt ctcgctgagg tcgcagcgtc acttgtggtc  2640
ctctggctgc ttggtaatac gcccttgcaa gacaaaggca attctacaca ctcaagaaac  2700
aattcctatg ccgtgattat cacttctaca agctcgtatt acgtgtttta catctacgta  2760
ggagtggccg acactctgct cgcgatgggt ttcttccgag gactcccact cgttcacacg  2820
cttatcactg tctccaagat tctccaccat aagatgcttc atagcgtact gcaggctccc  2880
atgtccacct tgaatacgct caaggcggga ggtattttga atcgcttctc aaaagatatt  2940
gcaattttgg atgaccttct gcccctgacg atcttcgact tcatccagtt gttgctgatc  3000
gtgattgggg ctattgcagt agtcgctgtc ctccagcctt acatttttgt cgcgaccgtt  3060
ccggtgatcg tggcgtttat catgctgcgg gcctatttct tgcagacgtc acagcagctt  3120
aagcaactgg agtctgaagg gaggtcgcct atctttacgc atcttgtgac cagtttgaag  3180
ggattgtgga cgttgcgcgc ctttggcagg cagccctact ttgaaacact gttccacaaa  3240
gcgctgaatc tccatacggc aaattggttt ttgtatttga gtaccctccg atggtttcag  3300
atgcgcattg agatgatttt tgtgatcttc tttatcgcgg tgacttttat ctccatcttg  3360
accacgggag agggcgaggg acgggtcggt attatcctga cactcgccat gaacattatg  3420
agcactttgc agtgggcagt gaacagctcg attgatgtgg atagcctgat gaggtccgtt  3480
tcgagggtct ttaagttcat cgacatgccg acggagggaa agcccacaaa aagtacgaaa  3540
ccctataaga atgggcaatt gagtaaggta atgatcatcg agaacagtca cgtgaagaag  3600
gatgacatct ggcctagcgg gggtcagatg accgtgaagg acctgacggc aaaatacacc  3660
gagggaggga acgcaatcct tgaaaacatc tcgttcagca ttagccccgg tcagcgtgtg  3720
gggttgctcg ggaggaccgg gtcaggaaaa tcgacgttgc tgtcggcctt cttgagactt  3780
ctgaatacag agggtgagat ccagatcgac ggcgtttcgt gggatagcat caccttgcag  3840
cagtggcgga aagcgtttgg agtaatcccc caaaaggtct ttatctttag cggaaccttc  3900
cgaaagaatc tcgatcctta tgaacagtgg tcagatcaag agatttggaa agtcgcggac  3960
gaggttggcc ttcggagtgt aatcgagcag tttccgggaa aactcgactt tgtccttgta  4020
gatgggggat gcgtcctgtc gcatgggcac aagcagctca tgtgcctggc gcgatccgtc  4080
ctctctaaag cgaaaattct tctcttggat gaaccttcgg cccatctgga cccggtaacg  4140
tatcagatca tcagaaggac acttaagcag gcgtttgccg actgcacggt gattctctgt  4200
gagcatcgta tcgaggccat gctcgaatgc cagcaatttc ttgtcatcga agagaataag  4260
gtccgccagt acgactccat ccagaagctg cttaatgaga gatcattgtt ccggcaggcg  4320
atttcaccat ccgataggt gaaacttttt ccacacagaa attcgtcgaa gtgcaagtcc  4380
aaaccgcaga tcgcggcctt gaaagaagag actgaagaag aagttcaaga cacgcgtctt  4440
taa                                                                4443

SEQ ID NO: 5           moltype = RNA  length = 1359
FEATURE                Location/Qualifiers
misc_feature           1..1359
                       note = chemically synthesized oligonucleotide
source                 1..1359
                       mol_type = other RNA
                       organism = synthetic construct
SEQUENCE: 5
atgagcaccg ccgtgctgga gaaccccggc ctgggccgca agctgagcga cttcggccag  60
gagaccagct acatcgagga caactgcaac cagaacggcg ccatcagcct gatcttcagc  120
```

-continued

```
ctgaaggagg aggtgggcgc cctggccaag gtgctgcgcc tgttcgagga gaacgacgtg  180
aacctgaccc acatcgagag ccgccccagc cgcctgaaga aggacgagta cgagttcttc  240
acccacctgg acaagcgcag cctgcccgcc ctgaccaaca tcatcaagat cctgcgccac  300
gacatcggcg ccaccgtgca cgagctgagc cgcgacaaga agaaggacac cgtgccctgg  360
ttcccccgca ccatccagga gctggaccgc ttcgccaacc agatcctgag ctacggcgcc  420
gagctggacg ccgaccaccc cggcttcaag gaccccgtgt accgcgcccg ccgcaagcag  480
ttcgccgaca tcgcctacaa ctaccgccac ggccagccca tcccccgcgt ggagtacatg  540
gaggaggaga agaagacctg gggcaccgtg ttcaagaccc tgaagagcct gtacaagacc  600
cacgcctgct acgagtacaa ccacatcttc cccctgctgg agaagtactg cggcttccac  660
gaggacaaca tcccccagct ggaggacgtg agccagttcc tgcagacctg caccggcttc  720
cgcctgcgcc ccgtggccgg cctgctgagc agccgcgact tcctgggcgg cctggccttc  780
cgcgtgttcc actgcaccca gtacatccgc cacggcagca agcccatgta cacccccgag  840
cccgacatct gccacgagct gctgggccac gtgcccctgt tcagcgaccg cagcttcgcc  900
cagttcagcc aggagatcgg cctggccagc ctgggcgccc ccgacgagta catcgagaag  960
ctggccacca tctactggtt caccgtggag ttcggcctgt gcaagcaggg cgacagcatc  1020
aaggcctacg gcgccggcct gctgagcagc ttcggcgagc tgcagtactg cctgagcgag  1080
aagcccaagc tgctgcccct ggagctggag aagaccgcca tccagaacta caccgtgacc  1140
gagttccagc ccctgtacta cgtggccgag agcttcaacg acgccaagga gaaggtgcgc  1200
aacttcgccg ccaccatccc ccgccccttc agcgtgcgct acgaccccta cacccagcgc  1260
atcgaggtgc tggacaacac ccagcagctg aagatcctgg ccgacagcat caacagcgag  1320
atcggcatcc tgtgcagcgc cctgcagaag atcaagtaa                        1359
```